United States Patent
Plant et al.

(10) Patent No.: US 6,489,490 B1
(45) Date of Patent: Dec. 3, 2002

(54) 2-(2-CHLOROPHENYL)-3,4-DIHYDRO-2H-PYRROL DERIVATIVES

(75) Inventors: Andrew Plant, Leverkusen (DE); Alan Graff, Leverkusen (DE); Udo Kraatz, Leverkusen (DE); Christoph Erdelen, Leichlingen (DE); Andreas Turberg, Haan (DE); Norbert Mencke, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/700,289

(22) PCT Filed: May 5, 1999

(86) PCT No.: PCT/EP99/03063

§ 371 (c)(1),
(2), (4) Date: Nov. 13, 2000

(87) PCT Pub. No.: WO99/59968

PCT Pub. Date: Nov. 25, 1999

(30) Foreign Application Priority Data

May 18, 1998 (DE) .......................... 198 22 247

(51) Int. Cl.$^7$ .................. C07D 207/20; A01N 43/36
(52) U.S. Cl. .................. 548/525; 548/527; 548/565; D22/120
(58) Field of Search ................ 548/525, 527, 548/565

(56) References Cited

FOREIGN PATENT DOCUMENTS

| EP | 0167419 | | 1/1986 |
| FR | 2607361 | | 6/1988 |
| GB | 1098355 | * | 1/1968 |
| WO | 95/04719 | | 2/1995 |
| WO | 98/22438 | | 5/1998 |

OTHER PUBLICATIONS

Katrizky et al, Synthesis (1991), (10), 863–7 CAS Abstract only.*
*Patent Abstracts of Japan, vol. 199, No. 607, Jul. 31, 1996 & JP 08 073446 A (Nippon Soda Co. Ltd), Mar. 19, 1996.

*W. Koller et al, "Ein neues Darstellungsverfahren für 2–Aryl–deltal–pyrroline und 2–Aryl–deltal–piperidine" Chemische Berichte, Bd. 96, 1963, Seiten 93–113, XP002117316, Weinheim De in der Anmeldung erwähnt, Seite 106–Seite 109; Beispiele 37–39.

Bull. Soc. Chimi.Fr., (month unavailable), 1974, pp. 258–262, R. Weil, "N° 53.–Étude des combinaisons du potassium avec quelques hétërocycles aromatiques azotés en solution dans le tëtrahydrofuranne".

Chem. Ber., 116, (month unavailable) 1983, pp. 3931–3946, H. Quast et al "N–Chlorierung und Dehydrochlorierung arylsubstituierter Piperidine, 3–Azabicyclo[3.3.1]nonane und 3,7–Diazabicyclo[3.3.1]nonane. Synthese des ersten 3,7–Diazanoradamantans".

Journal für Praktische Chemic, 4. Reihe, Band 2, (month unavailable), 1955, pp. 53–83, Von F. Seidel et al, "Über die Bildungsweise der 2–Oxynaphthoesäure–(3)".

* cited by examiner

Primary Examiner—T. A. Solola
Assistant Examiner—Kamal Saeed
(74) Attorney, Agent, or Firm—Joseph C. Gil; John E. Mrozinski, Jr.

(57) ABSTRACT

The invention relates to novel 2-(2-chlorophenyl)-3,4-dihydro-2H-pyrrole derivatives of the formula (I)

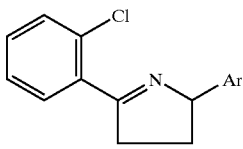

(I)

in which

Ar represents substituted phenyl, to a plurality of processes for their preparation and to their use as pesticides.

10 Claims, No Drawings

2-(2-CHLOROPHENYL)-3,4-DIHYDRO-2H-PYRROL DERIVATIVES

This application is a 371 of PCT/EP99/03063 filed May 5, 1999.

The invention relates to novel 2-(2-chlorophenyl)-3,4-dihydro-2H-pyrrole derivatives, to a plurality of processes for their preparation and to their use as pesticides.

Hitherto, only few substituted cyclic α,α'-diphenylimines are known: three 2,5-diphenyl-1-pyrrolines which are alkoxy-substituted in the 2-phenyl ring [5-(2,5-dimethoxyphenyl)-2-phenyl-3,4-dihydro-2H-pyrrole and 5-(4-methoxyphenyl)-2-phenyl-3,4-dihydro-2H-pyrrole from Chem. Ber. 96, 93 (1963) and the corresponding 4-propoxy compound from J. Prakt. Chem., Series 4, 1, 57 (1955)] and the 2,6-diphenyl-3,4,5,6-tetrahydropyridine, which is not substituted any further [cf., for example, Bull. Soc. Chim. Fr. 1974, 258 and Chem. Ber. 116, 3931 (1983)].

Nothing is known concerning their suitability for use as pesticides.

This invention, accordingly, provides novel 2-(2-chlorophenyl)-3,4-dihydro-2H-pyrrole derivatives of the formula (I)

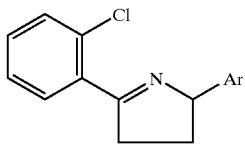

(I)

in which
Ar represents the radical

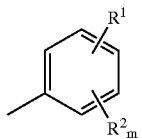

in which
m represents 0, 1, 2, 3 or 4,
$R^1$ represents halogen, cyano, trialkylsilyl, —CO—$NR^4R^5$, tetrahydropyranyl or represents one of the following groupings

 (l)

 (m)

 (n)

$R^2$ represents hydrogen, halogen, cyano, nitro, alkyl, alkoxy, halogenoalkyl, halogenoalkoxy, alkoxyalkoxy or —S(O)$_o$R$^3$,
o represents 0, 1 or 2,
$R^3$ represents alkyl or halogenoalkyl,
$R^4$ and $R^5$ independently of one another each represent hydrogen, alkyl, halogenoalkyl or represent phenyl or phenylalkyl, each of which is optionally mono- or polysubstituted by radicals from the list $W^1$,
X represents a direct bond, oxygen, sulphur, carbonyl, carbonyloxy, oxycarbonyl, alkylene, alkenylene, alkinylene, alkyleneoxy, oxyalkylene, thioalkylene, alkylenedioxy or dialkylsilylene, A represents phenyl, naphthyl or tetrahydronaphthyl, each of which is optionally mono- or poly-substituted by radicals from the list $W^1$, or represents 5- to 10-membered heterocyclyl containing one or two aromatic rings and having one or more heteroatoms from the group consisting of nitrogen, oxygen and sulphur and being in each case optionally mono- or polysubstituted by radicals from the list $W^2$,
B represents p-phenylene which is optionally mono- or disubstituted by radicals from the list $W^1$,
Z represents oxygen or sulphur,
D represents hydrogen, alkyl, alkenyl, alkinyl, halogenoalkyl, halogenoalkenyl, in each case optionally halogen-, alkyl-, alkenyl-, halogenoalkenyl-, phenyl-, styryl-, halogenophenyl- or halogenostyryl-substituted cycloalkyl or cycloalkylalkyl, represents in each case optionally halogen- or alkyl-substituted cycloalkenyl or cycloalkenylalkyl, represents in each case optionally nitro-, halogen-, alkyl-, alkoxy-, halogenoalkyl- or halogenoalkoxy-substituted phenylalkyl, naphthylalkyl, tetrahydronaphthylalkyl or hetarylalkyl having 5 or 6 ring members and one or two heteroatoms from the group consisting of nitrogen, oxygen and sulphur, represents —CO—$R^6$, —CO—$NR^7R^8$ or represents the grouping

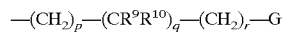

or
Z and D together represent optionally nitro-, halogen-, alkyl-, alkoxy-, halogenoalkyl- or halogenoalkoxy-substituted phenoxyalkyl,
Y represents a direct bond, oxygen, sulphur, carbonyl, carbonyloxy, oxycarbonyl, alkylene, alkenylene, alkinylene, alkyleneoxy, oxyalkylene, thioalkylene, alkylenedioxy or represents p-phenylene which is optionally mono- or disubstituted by radicals from the list $W^1$,
E represents hydrogen, alkyl, alkenyl, alkinyl, halogenoalkyl, halogenoalkenyl, in each case optionally halogen-, alkyl-, alkenyl-, halogenoalkenyl-, phenyl-, styryl-, halogenophenyl- or halogenostyryl-substituted cycloalkyl, represents in each case optionally halogen- or alkyl-substituted cycloalkenyl, represents phenyl which is optionally mono- to tetrasubstituted by radicals from the list $W^1$ or represents 5- or 6-membered hetaryl having one or two heteroatoms from the group consisting of nitrogen, oxygen and sulphur and being in each case optionally mono- to tetrasubstituted by radicals from the list $W^2$ or represents the grouping

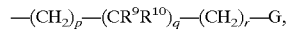

$R^6$ represents alkyl, alkoxy, alkenyl, alkenyloxy, in each case optionally halogen-, alkyl-, alkenyl-, halogenoalkyl- or halogenoalkenyl-substituted cycloalkyl, cycloalkyloxy or cycloalkylalkyloxy or represents in each case optionally nitro-, halogen-, alkyl-, alkoxy-, halogenoalkyl- or halogenoalkoxy-substituted phenyl or naphthyl,
$R^7$ represents hydrogen or alkyl,
$R^8$ represents alkyl, halogenoalkyl, in each case optionally halogen-, alkyl-, alkenyl-, halogenoalkyl- or halogenoalkenyl-substituted cycloalkyl or cycloalkylalkyl or represents in each case optionally halogen-, alkyl-, alkoxy-, halogenoalkyl- or halogenoalkoxy-substituted phenyl or phenylalkyl, p, q and r independently of one another each represent 0, 1, 2 or 3, their sum being smaller than 6, $R^9$ and $R^{10}$ independently of one another each represent hydrogen or alkyl, G represents cyano, represents an optionally halogen-, alkyl- or halogenoalkyl- and, at the point of linkage, optionally $R^{11}$-substituted 5- or 6-membered heterocycle having 1 to 3 identical or different heteroatoms from the group consisting of nitrogen, oxygen and sulphur or one of the following groups

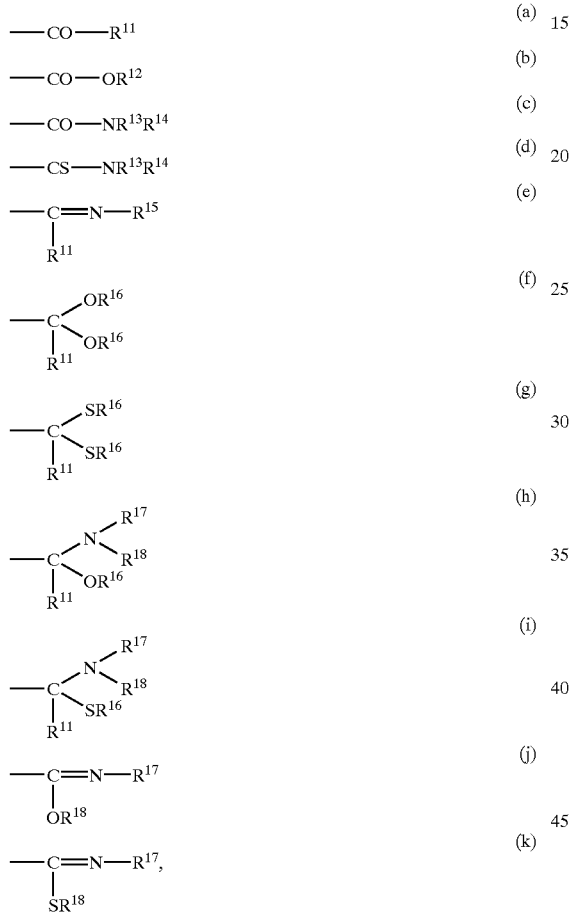

$R^{11}$ represents hydrogen, alkyl, alkenyl, halogenoalkyl, halogenoalkenyl, optionally halogen-, alkyl- or halogenoalkyl-substituted cycloalkyl or represents phenyl which is optionally mono- to pentasubstituted by alkylcarbonylamino, alkylcarbonylalkylamino and/or radicals from the list $W^3$, $R^{12}$ represents hydrogen, alkyl, alkenyl, halogenoalkyl, halogenoalkenyl, in each case optionally halogen-, alkyl- or halogenoalkyl-substituted cycloalkyl- or cycloalkylalkyl or represents arylalkyl which is optionally mono- to penta-substituted by radicals from the list $W^3$, $R^{13}$ and $R^{14}$ independently of one another each represent hydrogen, alkyl, alkenyl, halogenoalkyl, halogenoalkenyl, alkoxy, in each case optionally halogen-, alkyl- or halogenoalkyl-substituted cycloalkyl or cycloalkylalkyl, represents aryl or arylalkyl, each of which is optionally mono- to penta-substituted by radicals from the list $W^3$, represent —$OR^{12}$ or —$NR^{11}R^{12}$ or together represent an alkylene chain having 2 to 6 members in which optionally one methylene group is replaced by oxygen, $R^{15}$ represents —$OR^{12}$, —$NR^{11}R^{12}$ or —$N(R^{11})$—$COOR^{12}$, $R^{16}$, $R^{17}$ and $R^{18}$ independently of one another each represent alkyl, $W^1$ represents hydrogen, halogen, cyano, formyl, nitro, alkyl, trialkylsilyl, alkoxy, halogenoalkyl, halogenoalkoxy, halogenoalkenyloxy, alkylcarbonyl, alkoxycarbonyl, pentafluorothio or —$S(O)_oR^3$, $W^2$ represents halogen, cyano, formyl, nitro, alkyl, trialkylsilyl, alkoxy, halogenoalkyl, halogenoalkoxy, alkylcarbonyl, alkoxycarbonyl, pentafluorothio, —$S(O)_oR^3$ or —$C(R^{11})$=N—$R^{15}$, $W^3$ represents halogen, cyano, nitro, alkyl, alkoxy, halogenoalkyl, halogenoalkoxy, dialkylamino, —$S(O)_o R^3$, —$COOR^{19}$ or —$CONR^{20}R^{21}$, $R^{19}$ represents hydrogen, alkyl, halogenoalkyl, optionally halogen-, alkyl- or halogenoalkyl-substituted cycloalkyl or represents phenyl which is optionally mono- to pentasubstituted by radicals from the list $W^4$, $R^{20}$ and $R^{21}$ independently of one another each represent hydrogen, alkyl, alkenyl, halogenoalkyl, halogenoalkenyl, alkoxy, in each case optionally halogen-, alkyl- or halogenoalkyl-substituted cycloalkyl or cycloalkylalkyl or represent aryl or arylalkyl, each of which is optionally mono- to pentasubstituted by radicals from the list $W^4$, represent —$OR^{16}$ or —$NR^{17}R^{18}$ or together represent an alkylene chain having 2 to 6 members in which optionally one methylene group is replaced by oxygen, and $W^4$ represents halogen, cyano, nitro, alkyl, alkoxy, halogenoalkyl, halogenoalkoxy, dialkylamino, alkoxycarbonyl, dialkylaminocarbonyl or —$S(O)_oR^3$.

Depending, inter alia, on the nature of the substituents, the compounds of the formula (I) may be present as geometric and/or optical isomers or isomer mixtures, of various compositions, which can be separated, if appropriate, in a customary manner. The present invention provides both the pure isomers and the isomer mixtures, their preparation and use and compositions comprising them. However, hereinbelow, for the sake of simplicity, compounds of the formula (I) are always referred to, although this may mean both the pure compounds and, if appropriate, also mixtures having varying proportions of isomeric compounds.

Furthermore, it has been found that the novel compounds of the formula (I) are obtained by one of the processes described below.

A) Cyclic imines of the formula (I)

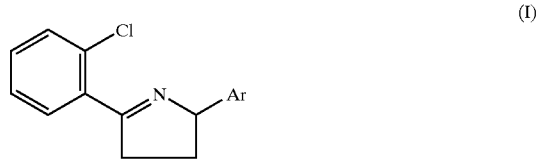

(I)

in which
Ar is as defined above
can be prepared by
a) reacting aminoketone derivatives of the formula (VIII)

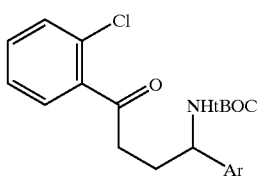

in which

Ar is as defined above with an acid, followed by cyclocondensation, if appropriate in the presence of an acid binder, or b) reducing the nitro group of nitroketones of the formula (XVIII)

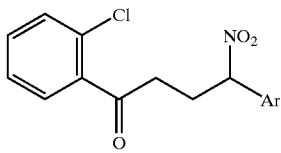

in which

Ar is as defined above, where

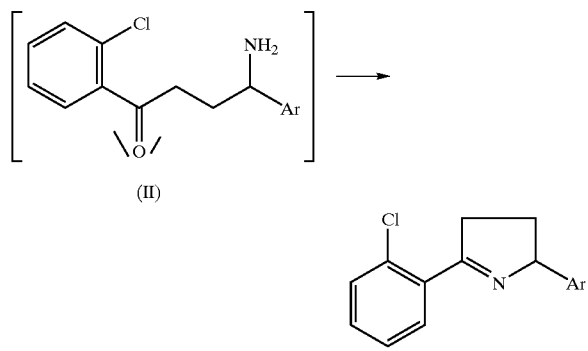

an aminoketone intermediate of the formula (II) is formed which, however, is cyclocondensed in situ to (I), in particular in an acidic medium, or c) hydrolysing imines of the formula (XXVII)

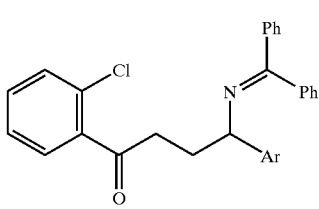

in which Ar is as defined above with aqueous acids

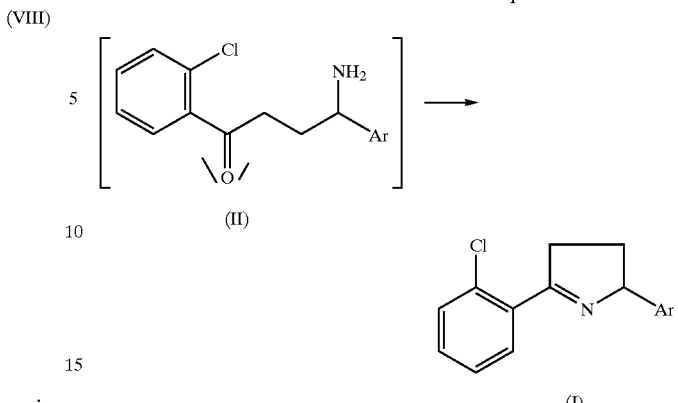

where an aminoketone intermediate of the formula (II) is formed which, however, is cyclocondensed in situ to (I).

B) Cyclic imines of the formula (I) can also be prepared by reacting cyclic O-methylsulphonyl oximes of the formula (III)

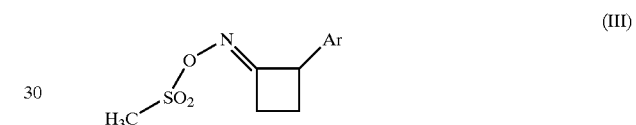

in which

Ar is as defined above with aryl Grignard compounds of the formula (IV)

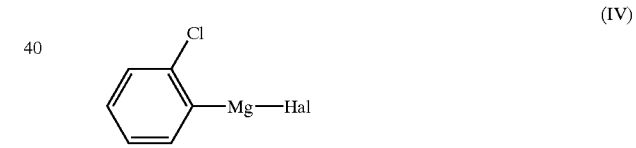

in which

Hal represents bromine or iodine in the presence of a diluent.

C) Cyclic imines of the formula (I-b)

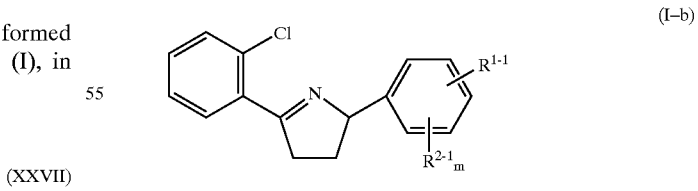

in which m is as defined above, $R^{1-1}$ represents A or one of the groupings below —B—Z—D  (m)

-continued

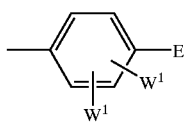
(n-a)

where

A, B, D, E, $W^1$ and Z are each as defined above and $R^{2-1}$ represents hydrogen, fluorine, cyano, nitro, alkyl, alkoxy, halogenoalkyl, halogenoalkoxy, alkoxyalkoxy or —$SR^3$ where $R^3$ is as defined above can be prepared by coupling compounds of the formula (V)

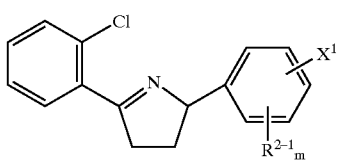
(V)

in which $R^{2-1}$ and m are each as defined above and $X^1$ represents bromine, iodine or —$OSO_2CF_3$ with boronic acids of the formula (VI)

(VI)

in which $R^{1-1}$ is as defined above in the presence of a catalyst and in the presence of an acid binder and in the presence of a solvent.

D) Cyclic imines of the formula (I-c)

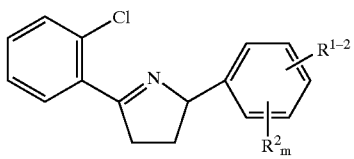
(I-c)

in which $R^2$ and m are each as defined above, $R^{1-2}$ represents one of the groupings below (m-b) —B—Z—$D^1$ (n-b) —$Y^1$—$E^1$ in which B and Z are each as defined above, $Y^1$ represents oxygen or sulphur and $D^1$ and $E^1$ represent the grouping

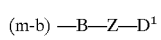

in which $R^9$, $R^{10}$, G, p, q and r are each as defined above can be prepared by condensing cyclic imines of the formula (I-d)

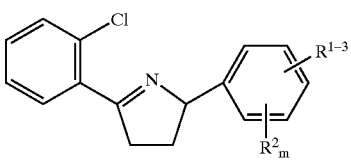
(I-d)

in which $R^2$ and m are each as defined above and $R^{1-3}$ represents one of the groupings below —B—Z—H (m-c)

—$Y^1$—H (n-c)

in which

B, $Y^1$ and Z are each as defined above with compounds of the formula (VII)

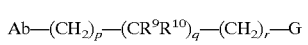
(VII)

in which $R^9$, $R^{10}$, G, p, q and r are each as defined above and

Ab represents a leaving group.

E) Cyclic imines of the formula (I-e)

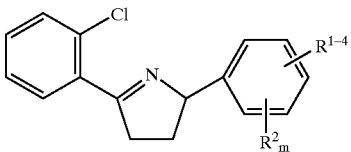
(I-e)

in which $R^2$ and m are each as defined above and $R^{1-4}$ represents a grouping from the description of the compounds of the formula (I) according to the invention which contains the radical G, where G represents one of the abovementioned groupings (e) to (k), can be prepared by generally customary and known derivatizations of the corresponding keto derivatives, carboxylic acid derivatives or nitrites, i.e. compounds of the formula (I) in which G represents cyano or one of the groupings (a) to (d).

F) Cyclic imines of the formula (I-f)

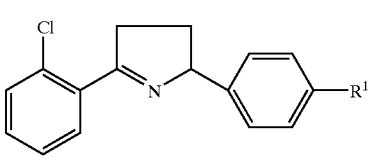
(I-f)

in which R¹ is as defined above can also be prepared by reacting, in a first step, α) o-chloroacetopienone of the formula (F-I)

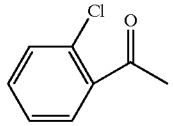
(F-I)

with dimethylmethyleneammonium chloride of the formula (F-II)

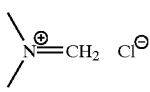
(F-II)

to give the compound of the formula (F-III)

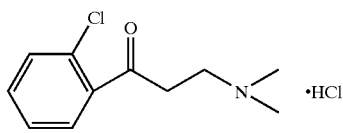
(F-III)

and reacting this, in a second step,

β) with benzyl cyanides of the formula (F-IV)

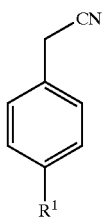
(F-IV)

in which R¹ is as defined above to give compounds of the formula (F-V)

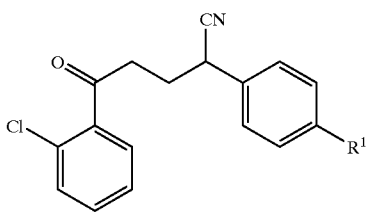
(F-V)

which, in the next step,

δ) are derivatized with aqueous sodium hydroxide solution/H₂O₂ to give compounds of the formula (F-VI)

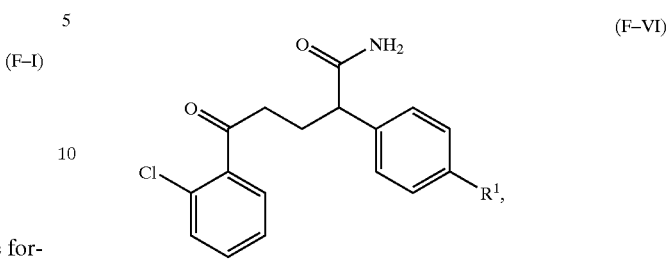
(F-VI)

in which R¹ is as defined above, and cyclizing these, in a final step,

γ) by reaction with PIFA (1,1-bis(trifluoroacetoxy)iodobenzene) of the formula (F-VII)

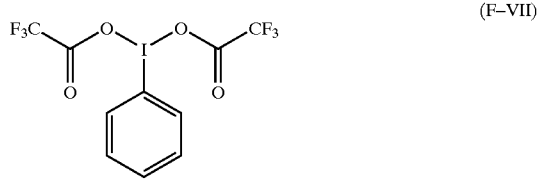
(F-VII)

to cyclic imines of the formula (I-f).

G) Cyclic imines of the formula (I)

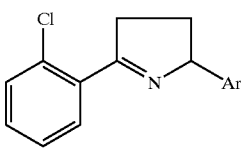
(I)

in which Ar is as defined above can also be prepared by reacting, in a first step, α) arylbutyrolactams of the formula (XI)

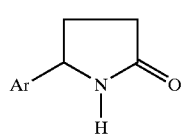
(XI)

with o-chlorobenzoyl chloride

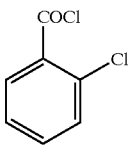

to give compounds of the formula G(I)

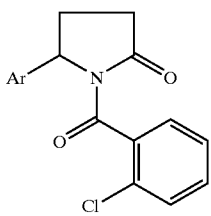
G(I)

and reacting these, in a second step,

β) with methyl o-chlorobenzoate

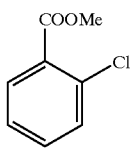

to give compounds of the formula G(II)

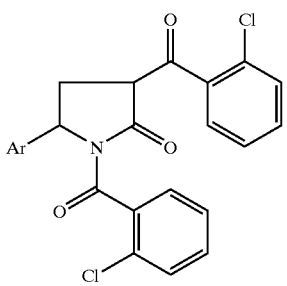
G(II)

which, in a final step, are reacted

δ) with HBr/glacial acetic acid to give compounds of the formula (I)

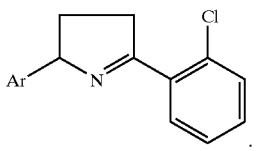

Furthermore, it has been found that the novel compounds of the formula (I) exhibit very good activity as pesticides, in particular against arthropods in agriculture, but also against parasites in the keeping of useful animals and pets, combined with good compatibility with plants.

The formula (I) provides a general definition of the compounds according to the invention. Preferred substituents or ranges of the radicals listed in the formulae mentioned hereinabove and hereinbelow are illustrated below.

Ar preferably represents the radical

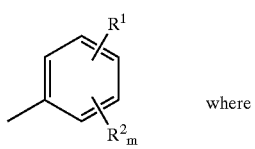

where m preferably represents 0, 1, 2, 3.

$R^1$ preferably represents a substituent in the meta or para position from the group consisting of hydrogen, halogen, cyano, tri-($C_1$–$C_6$-alkyl)-silyl, —CO—$NR^4R^5$, tetrahydropyranyl or one of the following groupings —X—A (l)

—B—Z—D (m)

—Y—E. (n)

$R^2$ preferably represents hydrogen, halogen, cyano, nitro, $C_1$–$C_{16}$-alkyl, $C_1$–$C_{16}$-alkoxy, $C_1$–$C_6$-halogenoalkyl, $C_1$–$C_6$-halogenoalkoxy, $C_1$–$C_8$-alkoxy-$C_1$–$C_8$-alkoxy or —$S(O)_oR^3$.

o preferably represents 0, 1 or 2.

$R^3$ preferably represents optionally fluorine- or chlorine-substituted $C_1$–$C_6$-alkyl.

$R^4$ and $R^5$ independently of one another each preferably represent hydrogen, $C_1$–$C_6$-alkyl, $C_1$–$C_6$-halogenoalkyl or represent phenyl or phenyl-$C_1$–$C_4$-alkyl, each of which is optionally mono- to trisubstituted by radicals from the list $W^1$.

X preferably represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylenedioxy or di-$C_1$–$C_4$-alkylsilylene.

A preferably represents phenyl, naphthyl or tetrahydronaphthyl, each of which is optionally mono- to tetrasubstituted by radicals from the list $W^1$, or represents 5- to 10-membered heterocyclyl containing 1 or 2 aromatic rings and having 1 to 4 heteroatoms, which contains 0 to 4 nitrogen atoms, 0 to 2 oxygen atoms and 0 to 2 sulphur atoms (in particular furyl, benzofuryl, thienyl, benzothienyl, oxazolyl, benzoxazolyl, thiazolyl, benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl), and is in each case optionally mono- to tetrasubstituted by radicals from the list $W^2$.

B preferably represents p-phenylene which is optionally mono- or disubstituted by radicals from the list $W^1$.

Z preferably represents oxygen or sulphur.

D preferably represents hydrogen, $C_1$–$C_{16}$-alkyl, $C_2$–$C_{16}$-alkenyl, $C_2$–$C_6$-alkinyl, $C_1$–$C_{16}$-halogenoalkyl, $C_2$–$C_{16}$-halogenoalkenyl, in each case optionally halogen-, $C_1$–$C_4$-alkyl-, $C_2$–$C_4$-alkenyl-, $C_2$–$C_4$-halogenoalkenyl-, phenyl-, styryl-, halogenophenyl- or halogenostyryl-substituted $C_3$–$C_8$-cycloalkyl or $C_3$–$C_8$-cycloalkyl-$C_1$–$C_6$-alkyl, represents in each case optionally halogen- or $C_1$–$C_4$-alkyl-substituted $C_5$–$C_8$-cycloalkenyl or $C_5$–$C_8$-cycloalkenyl-$C_1$–$C_4$-alkyl, represents in each case optionally nitro-, halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, naphthyl-$C_1$–$C_6$-alkyl, tetrahydronaphthyl-$C_1$–$C_6$-alkyl or hetaryl-$C_1$–$C_6$-alkyl having 5 or 6 ring members and 1 or 2 heteroatoms from the group consisting of nitrogen, oxygen and sulphur (in particular furyl methyl, thienylmethyl, pyrrolylmethyl, oxazolylmethyl, isoxazolylmethyl, thiazolylmethyl or pyridylmethyl), represents —CO—$R^6$, —CO—$NR^7R^8$ or represents the grouping

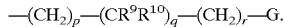

Z and D together also preferably represent in each case optionally nitro-, halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenoxy-$C_1$–$C_4$-alkyl.

Y preferably represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylenedioxy or represents p-phenylene which is optionally mono- or disubstituted by radicals from the list $W^1$.

E preferably represents hydrogen, $C_1$–$C_{16}$-alkyl, $C_2$–$C_{16}$-alkenyl, $C_2$–$C_6$-alkinyl, $C_1$–$C_6$-halogenoalkyl, $C_2$–$C_{16}$-halogenoalkenyl, optionally halogen-, $C_1$–$C_4$-alkyl-, $C_2$–$C_4$-alkenyl-, $C_2$–$C_4$-halogenoalkenyl-, phenyl-, styryl-, halogenophenyl- or halogenostyryl-substituted $C_3$–$C_8$-cycloalkyl, represents optionally halogen- or $C_1$–$C_4$-alkyl-substituted $C_5$–$C_8$-cycloalkenyl, represents phenyl which is optionally mono- to tetrasubstituted by radicals from the list $W^1$ or represents 5- or 6-membered hetaryl having 1 or heteroatoms from the group consisting of nitrogen, oxygen and sulphur (in particular furyl, thienyl, pyrrolyl, oxazolyl, isoxazolyl, thiazolyl or pyridyl) which is in each case optionally mono- to tetrasubstituted by radicals from the list $W^2$ or represents the grouping

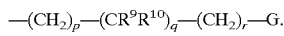

$R^6$ preferably represents $C_1$–$C_{12}$-alkyl, $C_1$–$C_{12}$-alkoxy, $C_2$–$C_{12}$-alkenyl, $C_2$–$C_{12}$-alkenyloxy, in each case optionally halogen-, $C_1$–$C_4$-alkyl-, $C_2$–$C_4$-alkenyl-, $C_1$–$C_4$-halogenoalkyl- or $C_2$–$C_4$-halogenoalkenyl-substituted $C_3$–$C_8$-cycloalkyl, $C_3$–$C_8$-cycloalkyloxy or $C_3$–$C_8$-cycloalkyl-$C_1$–$C_6$-alkyloxy or represents phenyl or naphthyl which is in each case optionally mono- to tetrasubstituted by nitro, halogen, $C_1$–$C_{12}$-alkyl, $C_1$–$C_{12}$-alkoxy, $C_1$–$C_{12}$-halogenoalkyl or $C_1$–$C_{12}$-halogenoalkoxy.

$R^7$ preferably represents hydrogen or $C_1$–$C_{12}$-alkyl.

$R^8$ preferably represents $C_1$–$C_{12}$-alkyl, $C_1$–$C_{12}$-halogenoalkyl, in each case optionally halogen-, $C_1$–$C_4$-alkyl-, $C_2$–$C_4$-alkenyl-, $C_1$–$C_4$-halogenoalkyl- or $C_2$–$C_4$-halogenoalkenyl-substituted $C_3$–$C_8$-cycloalkyl or $C_3$–$C_8$-cycloalkyl-$C_1$–$C_6$-alkyl or represents phenyl or phenyl-$C_1$–$C_6$-alkyl, each of which is optionally mono- to tetrasubstituted by halogen, $C_1$–$C_{12}$-alkyl, $C_1$–$C_{12}$-alkoxy, $C_1$–$C_{12}$-halogenoalkyl or $C_1$–$C_{12}$-halogenoalkoxy.

p, q and r independently of one another each preferably represent 0, 1, 2 or 3, their sum being smaller than 6.

$R^9$ and $R^{10}$ independently of one another each preferably represent hydrogen or $C_1$–$C_4$-alkyl.

G preferably represents cyano, represents a 5- or 6-membered heterocycle having 1 to 3 identical or different heteroatoms from the group consisting of nitrogen, oxygen and sulphur (in particular 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl) and being optionally mono- to trisubstituted by halogen, $C_1$–$C_4$-alkyl or $C_1$–$C_4$-halogenoalkyl and optionally, at the point of linkage, by the radical $R^{11}$, or represents one of the following groupings:

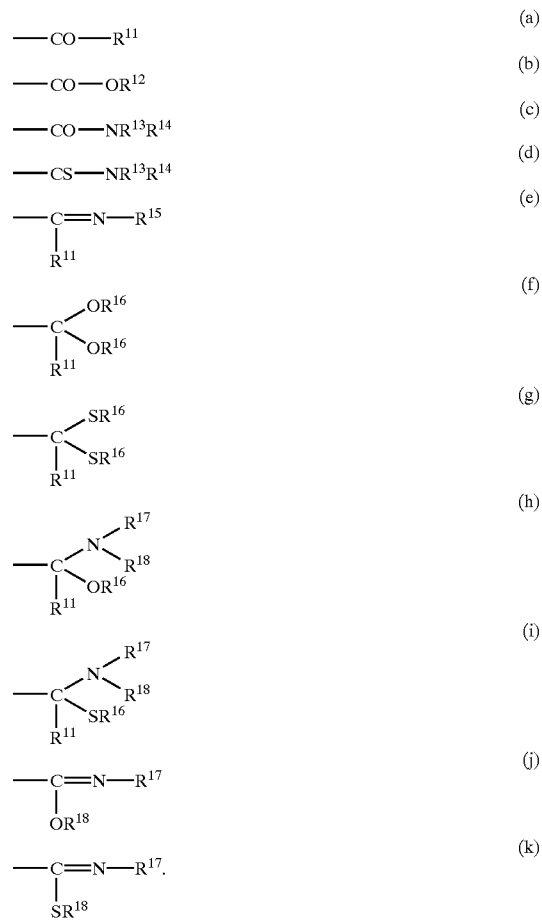

$R^{11}$ preferably represents hydrogen, $C_1$–$C_6$-alkyl, $C_2$–$C_6$-alkenyl, $C_1$–$C_4$-halogenoalkyl, $C_2$–$C_6$-halogenoalkenyl, optionally halogen-, $C_1$–$C_4$-alkyl- or $C_1$–$C_4$-halogenoalkyl-substituted $C_3$–$C_6$-cycloalkyl or represents phenyl which is optionally mono- to pentasubstituted by $C_1$–$C_4$-alkylcarbonylamino, $C_1$–$C_4$-alkylcarbonyl-$C_1$–$C_4$-alkylamino and/or radicals from the list $W^3$.

$R^{12}$ preferably represents hydrogen, $C_1$–$C_4$-alkyl, $C_2$–$C_6$-alkenyl, $C_1$–$C_4$-halogenoalkyl, $C_2$–$C_6$-halogenoalkenyl, in each case optionally halogen-, $C_1$–$C_4$-alkyl- or $C_1$–$C_4$-halogenoalkyl-substituted $C_3$–$C_6$-cycloalkyl or $C_3$–$C_6$-cycloalkyl-$C_1$–$C_4$-alkyl or represents $C_6$–$C_{10}$-aryl-$C_1$–$C_4$-alkyl (in particular phenyl-$C_1$–$C_4$-alkyl or naphthyl-$C_1$–$C_4$-alkyl) which is optionally mono- to tetrasubstituted by radicals from the list $W^3$.

$R^{13}$ and $R^{14}$ independently of one another each preferably represent hydrogen, $C_1$–$C_4$-alkyl, $C_3$–$C_6$-alkenyl, $C_1$–$C_4$-halogenoalkyl, $C_3$–$C_6$-halogenoalkenyl, $C_1$–$C_4$-alkoxy, in each case optionally halogen-, $C_1$–$C_4$-alkyl- or $C_1$–$C_4$-halogenoalkyl-substituted $C_3$–$C_6$-cycloalkyl or $C_3$–$C_6$-cycloalkyl-$C_1$–$C_4$-alkyl, represent phenyl or phenyl-$C_1$–$C_4$-alkyl, each of which is optionally mono- to pentasubstituted by radicals from the list $W^3$, represent —$OR^{12}$ or —$NR^{11}R^{12}$ or together represent an alkylene chain having 4 to 6 members in which optionally one methylene group is replaced by oxygen.

$R^{15}$ preferably represents $-OR^{12}$, $-NR^{11}R^{12}$ or $-N(R^{11})-COOR^{12}$.

$R^{16}$, $R^{17}$ and $R^{18}$ independently of one another each preferably represent $C_1-C_6$-alkyl.

$W^1$ preferably represents hydrogen, halogen, cyano, formyl, nitro, $C_1-C_6$-alkyl, tri-$C_1-C_4$-alkylsilyl, $C_1-C_{16}$-alkoxy, $C_1-C_6$-halogenoalkyl, $C_1-C_6$-halogenoalkoxy, $C_2-C_6$-halogenoalkenyloxy, $C_1-C_6$-alkylcarbonyl, $C_1-C_{16}$-alkoxycarbonyl, pentafluorothio or $-S(O)_oR^3$.

$W^2$ preferably represents halogen, cyano, formyl, nitro, $C_1-C_6$-alkyl, tri-$C_1-C_4$-alkylsilyl, $C_1-C_{16}$-alkoxy, $C_1-C_6$-halogenoalkyl, $C_1-C_6$-halogenoalkoxy, $C_1-C_6$-alkylcarbonyl, $C_1-C_{16}$-alkoxycarbonyl, pentafluorothio, $-S(O)_oR^3$ or $-C(R^{11})=N-R^{15}$.

$W^3$ preferably represents halogen, cyano, nitro, $C_1-C_4$-alkyl, $C_1-C_4$-alkoxy, $C_1-C_4$-halogenoalkyl, $C_1-C_4$-halogenoalkoxy, di-$C_1-C_4$-alkylamino, $-S(O)_oR^3$, $-COOR^{19}$ or $-CONR^{20}R^{21}$.

$R^{19}$ preferably represents hydrogen, $C_1-C_4$-alkyl, $C_1-C_4$-halogenoalkyl, optionally halogen-, $C_1-C_4$-alkyl- or $C_1-C_4$-halogenoalkyl-substituted $C_3-C_7$-cycloalkyl or represents phenyl which is optionally mono- to pentasubstituted by radicals from the list $W^4$.

$R^{20}$ and $R^{21}$ independently of one another each preferably represent hydrogen, $C_1-C_4$-alkyl, $C_3-C_6$-alkenyl, $C_1-C_4$-halogenoalkyl, $C_3-C_6$-halogenoalkenyl, $C_1-C_4$-alkoxy, in each case optionally halogen-, $C_1-C_4$-alkyl- or $C_1-C_4$-halogenoalkyl-substituted $C_3-C_6$-cycloalkyl or $C_3-C_6$-cycloalkyl-$C_1-C_4$-alkyl or represent phenyl or phenyl-$C_1-C_4$-alkyl, each of which is optionally mono- to pentasubstituted by radicals from the list $W^4$, represent $-OR^{16}$ or $-NR^{17}R^{18}$ or together represent an alkylene chain having 4 to 6 members in which optionally one methylene group is replaced by oxygen.

$W^4$ preferably represents halogen, cyano, nitro, $C_1-C_6$-alkyl, $C_1-C_6$-alkoxy, $C_1-C_6$-halogenoalkyl, $C_1-C_6$-halogenoalkoxy, di-$C_1-C_4$-alkylamino, $C_1-C_6$-alkoxycarbonyl, di-$C_1-C_6$-alkylaminocarbonyl or $-S(O)_oR^3$.

Ar particularly preferably represents the radical

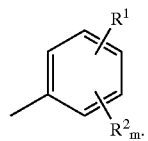

m particularly preferably represents 0, 1 or 2.

$R^1$ particularly preferably represents a substituent in the meta or para position from the group consisting of hydrogen, fluorine, chlorine, bromine, iodine, cyano, tri-($C_1-C_4$-alkyl)-silyl, $-CO-NR^4R^5$, tetrahydropyranyl or one of the following groupings

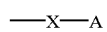 (l)

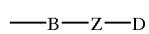 (m)

-continued

—Y—E. (n)

$R^2$ particularly preferably represents hydrogen, fluorine, chlorine, bromine, iodine, cyano, nitro, $C_1-C_{16}$-alkyl, $C_1-C_{16}$-alkoxy, in each case fluorine- or chlorine-substituted $C_1-C_6$-alkyl or $C_1-C_6$-alkoxy, represents $C_1-C_8$-alkoxy-$C_1-C_8$-alkoxy or $-S(O)_oR^3$.

o particularly preferably represents 0, 1 or 2.

$R^3$ particularly preferably represents $C_1-C_4$-alkyl or in each case fluorine- or chlorine-substituted methyl or ethyl.

$R^4$ and $R^5$ independently of one another each particularly preferably represent hydrogen, $C_1-C_6$-alkyl, fluorine- or chlorine-substituted $C_1-C_6$-alkyl or represent phenyl or benzyl, each of which is optionally mono- or disubstituted by radicals from the list $W^1$.

X particularly preferably represents a direct bond, oxygen, sulphur, carbonyl, carbonyloxy, oxycarbonyl, $C_1-C_4$-alkylene, $C_2-C_4$-alkenylene, $C_2-C_4$-alkinylene, $C_1-C_4$-alkylenoxy, $C_1-C_4$-oxyalkylene, $C_1-C_4$-thioalkylene, $C_1-C_4$-alkylenedioxy or di-$C_1-C_4$-alkylsilylene.

A particularly preferably represents phenyl, naphthyl or tetrahydronaphthyl, each of which is optionally mono- to trisubstituted by radicals from the list $W^1$, or represents 5- to 10-membered heterocyclyl containing one or two aromatic rings and having 1 to 4 heteroatoms which contains 0 to 4 nitrogen atoms, 0 to 2 oxygen atoms and 0 to 2 sulphur atoms (in particular furyl, benzofuryl, thienyl, benzothienyl, oxazolyl, benzoxazolyl, thiazolyl, benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl) and is in each case optionally mono- to trisubstituted by radicals from the list $W^2$.

B particularly preferably represents p-phenylene which is optionally mono- or disubstituted by radicals from the list $W^1$.

Z particularly preferably represents oxygen or sulphur.

D particularly preferably represents hydrogen, $C_1-C_16$-alkyl, $C_2-C_{16}$-alkenyl, $C_2-C_6$-alkinyl, in each case fluorine- or chlorine-substitited $C_1-C_4$-alkyl or $C_2-C_4$-alkenyl, represents $C_3-C_6$-cycloalkyl or $C_3-C_6$-cycloalkyl-$C_1-C_4$-alkyl, each of which is optionally substituted by fluorine, chlorine, bromine, $C_1-C_4$-alkyl, $C_2-C_4$-alkenyl, by fluorine- or chlorine-substituted $C_2-C_4$-alkenyl, by phenyl, styryl, in each case fluorine-, chlorine- or bromine-substituted phenyl or styryl, represents in each case optionally fluorine-, chlorine-, bromine- or $C_1-C_4$-alkyl-substituted $C_5-C_6$-cycloalkenyl or $C_5-C_6$-cycloalkenyl-$C_1-C_4$-alkyl, represents phenyl-$C_1-C_4$-alkyl, napthyl-$C_1-C_4$-alkyl, tetrahydronaphthyl-$C_1-C_6$-alkyl or hetaryl-$C_1-C_4$-alkyl having 5 or 6 ring members and one or two heteroatoms from the group consisting of nitrogen, oxygen and sulphur (in particular furylmethyl, thienylmethyl, pyrrolylmethyl, oxazolylmethyl, isoxazolylmethyl, thioazolylmethyl or pyridylmethyl), each of which is optionally substituted by nitro, fluorine, chlorine, bromine, $C_1-C_6$-alkyl, $C_1-C_6$- alkoxy, in each case fluorine- or chlorine-substituted $C_1$–$C_4$-alkyl or $C_1$–$C_4$-alkoxy, represents —CO—$R^6$, —CO—$NR^7R^8$ or the grouping

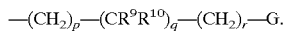

Z and D together also particularly preferably represent substituted phenoxy-$C_1$–$C_3$-alkyl which is optionally substituted by nitro, fluorine, chlorine, bromine, $C_1$–$C_4$-alkyl, $C_1$–$C_4$-alkoxy, in each case fluorine- or chlorine-substituted $C_1$–$C_4$-alkyl or $C_1$–$C_4$-alkoxy.

Y particularly preferably represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylenedioxy or represents p-phenylene which is optionally mono- or disubstituted by radicals from the list $W^1$.

E particularly preferably represents hydrogen, $C_1$–$C_{16}$-alkyl, $C_2$–$C_{16}$-alkenyl, $C_2$–$C_6$-alkinyl, in each case fluorine- or chlorine-substituted $C_1$–$C_4$-alkyl or $C_2$–$C_4$-alkenyl, represents $C_3$–$C_6$-cycloalkyl which is optionally substituted by fluorine, chlorine, bromine, $C_1$–$C_4$-alkyl, $C_2$–$C_4$-alkenyl, by fluorine- or chlorine-substituted $C_2$–$C_4$-alkenyl, by phenyl, styryl or in each case fluorine-, chlorine- or bromine-substituted phenyl or styryl, represents optionally fluorine-, chlorine-, bromine- or $C_1$–$C_4$-alkyl-substituted $C_5$–$C_6$-cycloalkenyl, represents phenyl which is optionally mono- to trisubstituted by radicals from the list $W^1$ or represents 5- or 6-membered hetaryl having 1 or 2 heteroatoms from the group consisting of nitrogen, oxygen and sulphur (in particular furyl, thienyl, pyrrolyl, oxazolyl, isoxazolyl, thiazolyl or pyridyl), each of which is optionally mono- or disubstituted by radicals from the list $W^2$, or represents the grouping

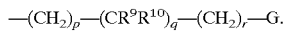

$R^6$ particularly preferably represents $C_1$–$C_6$-alkyl, $C_1$–$C_6$-alkoxy, $C_2$–$C_6$-alkenyl, $C_2$–$C_6$-alkenyloxy, represents $C_3$–$C_6$-cycloalkyl, $C_3$–$C_6$-cycloalkyloxy or $C_3$–$C_6$-cycloalkyl-$C_1$–$C_2$-alkyloxy, each of which is optionally substituted by fluorine, chlorine, $C_1$–$C_3$-alkyl or in each case fluorine- or chlorine-substituted $C_1$–$C_2$-alkyl or $C_2$–$C_3$-alkenyl, or represents phenyl which is optionally mono- or disubstituted by fluorine, chlorine, bromine, iodine, $C_1$–$C_4$-alkyl, $C_1$–$C_4$-alkoxy or by in each case fluorine- or chlorine-substituted $C_1$–$C_3$-alkyl or $C_1$–$C_4$-alkoxy.

$R^7$ particularly preferably represents hydrogen or $C_1$–$C_4$-alkyl.

$R^8$ particularly preferably represents $C_1$–$C_4$-alkyl or represents phenyl or benzyl, each of which is optionally mono- or disubstituted by fluorine, chlorine, bromine, $C_1$–$C_4$-alkyl or by in each case fluorine- or chlorine-substituted $C_1$–$C_4$-alkyl or $C_1$–$C_4$-alkoxy.

p, q and r independently of one another each particularly preferably represent 0, 1, 2 or 3, their sum being smaller than 6.

$R^9$ and $R^{10}$ independently of one another each particularly preferably represent hydrogen or $C_1$–$C_4$-alkyl.

G particularly preferably represents cyano, represents a 5- or 6-membered heterocycle having 1 to 3 identical or different heteroatoms from the group consisting of nitrogen, oxygen and sulphur (in particular 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl) and being optionally mono- to trisubstituted by fluorine, chlorine, bromine, $C_1$–$C_4$-alkyl or by fluorine- or chlorine-substituted $C_1$–$C_4$-alkyl and optionally, at the point of linkage, by the radical $R^{11}$, or represents one of the following groupings:

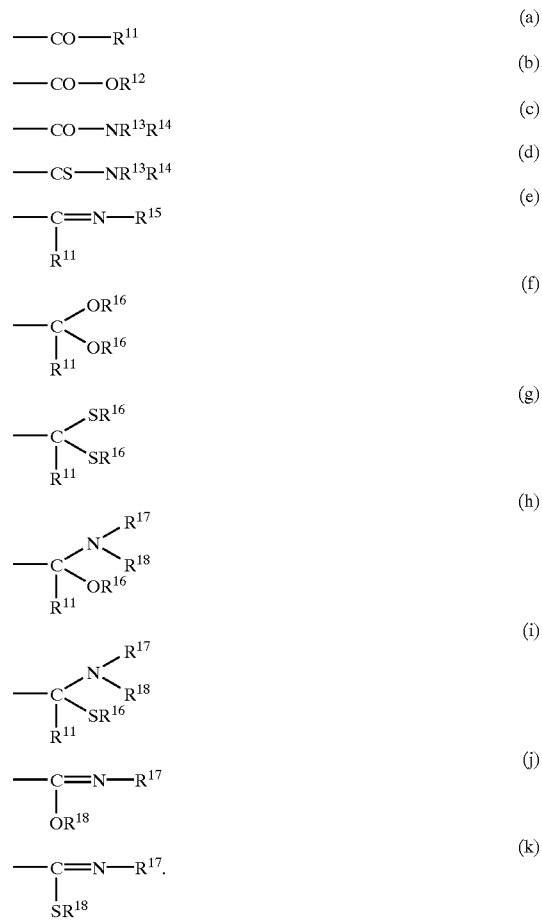

$R^{11}$ particularly preferably represents hydrogen, $C_1$–$C_6$-alkyl, $C_2$–$C_6$-alkenyl, in each case fluorine- or chlorine-substituted $C_1$–$C_4$-alkyl or $C_2$–$C_6$-alkenyl, represents $C_3$–$C_6$-cycloalkyl which is optionally substituted by fluorine, chlorine, $C_1$–$C_4$-alkyl or by fluorine- or chlorine-substituted $C_1$–$C_4$-alkyl, or represents phenyl which is optionally mono- to trisubstituted by $C_1$–$C_4$-alkylcarbonylamino, $C_1$–$C_4$-alkylcarbonyl-$C_1$–$C_4$-alkylamino and/or radicals from the list $W^3$.

$R^{12}$ particularly preferably represents hydrogen, $C_1$–$C_4$-alkyl, $C_3$–$C_6$-alkenyl, in each case fluorine- or chlorine-substituted $C_1$–$C_4$-alkyl or $C_3$–$C_6$-alkenyl, represents $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl or by fluorine- or chlorine-substituted $C_1$–$C_4$-alkyl, or represents phenyl-$C_1$–$C_4$-alkyl or naphthyl-$C_1$–$C_4$-alkyl, each of which is optionally mono- to trisubstituted by radicals from the list $W^3$.

$R^{13}$ and $R^{14}$ independently of one another each particularly preferably represent hydrogen, $C_1$–$C_4$-alkyl, $C_3$–$C_6$-alkenyl, in each case fluorine- or chlorine-substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl or by fluorine- or chlorine-substituted $C_1$–$C_4$-alkyl, represent phenyl or phenyl-$C_1$–$C_4$-alkyl, each of which is optionally mono- to trisubstituted by radicals from the list $W^3$, represent —$OR^{12}$ or –$NR^{11}R^{12}$ or together represent —$(CH_2)_5$—, —$(CH_2)_6$— or —$(CH_2)_2$—O—$(CH_2)_2$—.

$R^{15}$ particularly preferably represents —$OR^{12}$, —$NR^{11}R^{12}$ or —$N(R^{11})$—$COOR^{12}$.

$R^{16}$, $R^{17}$ and $R^{18}$ independently of one another each particularly preferably represent $C_1$–$C_4$-alkyl.

$W^1$ particularly preferably represents hydrogen, fluorine, chlorine, bromine, iodine, cyano, formyl, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, represents $C_1$–$C_4$-alkylcarbonyl, $C_1$–$C_4$-alkoxycarbonyl or —$S(O)_oR^3$.

$W^2$ particularly preferably represents fluorine, chlorine, bromine, cyano, formyl, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, represents $C_1$–$C_4$-alkylcarbonyl, $C_1$–$C_4$-alkoxycarbonyl, —$S(O)_oR^3$ or —$C(R^{11})$=$N$—$R^{15}$.

$W^3$ particularly preferably represents fluorine, chlorine, bromine, cyano, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, represents di-$C_1$–$C_4$-alkylamino, —$S(O)_oR^3$, —$COOR^{19}$ or —$CONR^{20}R^{21}$.

$R^{19}$ particularly preferably represents hydrogen, $C_1$–$C_4$-alkyl, fluorine- or chlorine-substituted $C_1$–$C_4$-alkyl, represents $C_3$–$C_6$-cycloalkyl which is optionally substituted by fluorine, chlorine, $C_1$–$C_4$-alkyl or by fluorine- or chlorine-substituted $C_1$–$C_4$-alkyl, or represents phenyl, which is optionally mono- to trisubstituted by radicals from the list $W^4$.

$R^{20}$ and $R^{21}$ independently of one another each particularly preferably represent hydrogen, $C_1$–$C_4$-alkyl, $C_3$–$C_6$-alkenyl, in each case fluorine- or chlorine-substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl or by fluorine- or chlorine-substituted-$C_1$–$C_4$-alkyl, or represent phenyl or phenyl-$C_1$–$C_4$-alkyl, each of which is optionally mono- to trisubstituted by radicals from the list $W^4$, represent —$OR^{16}$ or —$NR^{17}R^{18}$ or together represent —$(CH_2)_5$—, —$(CH_2)_6$— or —$(CH_2)_2$—O—$(CH_2)_2$—.

$W^4$ particularly preferably represents fluorine, chlorine, bromine, cyano, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, di-$C_1$–$C_4$-alkylamino, $C_1$–$C_4$-alkoxycarbonyl, di-$C_1$–$C_6$-alkylaminocarbonyl or —$S(O)_oR^3$.

Ar very particularly preferably represents the radical

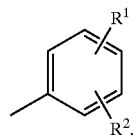

$R^1$ very particularly preferably represents a substituent in the meta or para position from the group consisting of hydrogen, fluorine, chlorine, bromine, iodine, cyano, —CO—$NR^4R^5$, tetrahydropyranyl or one of the groupings below

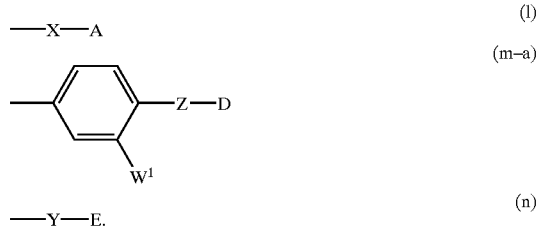

$R^2$ very particularly preferably represents hydrogen, fluorine, chlorine, bromine, methyl, ethyl, methoxy, ethoxy, methylthio, ethylthio, trifluoromethyl, difluoromethoxy, trifluoromethoxy or trifluormethylthio.

o very particularly preferably represents 0 or 2.

$R^3$ very particularly preferably represents methyl, ethyl, n-propyl, isopropyl, difluoromethyl or trifluoromethyl.

$R^4$ and $R^5$ independently of one another each very particularly preferably represent hydrogen, methyl, ethyl, n-propyl, isopropyl, n-butyl, isobutyl, sec-butyl, tert-butyl or represent phenyl or benzyl, each of which is optionally monosubstituted by a radical from the list $W^1$.

X very particularly preferably represents a direct bond, oxygen, sulphur, carbonyl, —$CH_2$—, —$(CH_2)_2$—, —CH=CH— (E or Z), —C≡C—, —$CH_2O$—, —$(CH_2)_2O$—, —$CH(CH_3)O$—, —$OCH_2$—, —$O(CH_2)_2$—, —$SCH_2$—, —$S(CH_2)_2$—, —SCH($CH_3$)—, $C_1$–$C_4$-alkylenedioxy, in particular —$OCH_2O$—, —$O(CH_2)_2O$— or —$OCH(CH_3)O$—.

A very particularly preferably represents phenyl which is optionally mono- or disubstituted by radicals from the list $W^1$ or represents furyl, benzofuryl, thienyl, benzothienyl, oxazolyl, benzoxazolyl, thiazolyl, benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl, each of which is optionally mono- or disubstituted by radicals from the list $W^2$.

Z very particularly preferably represents oxygen or sulphur.

D very particularly preferably represents hydrogen, methyl, ethyl, n-propyl, isopropyl, n-butyl, isobutyl, sec-butyl, tert-butyl, the isomeric pentyls, the isomeric hexyls, n-heptyl, n-octyl, n-isooctyl, n-nonyl, n-decyl, n-undecyl, n-dodecyl, n-tridecyl, n-tetradecyl, n-pentadecyl, n-hexadecyl, 2-propenyl, butenyl, pentenyl, hexenyl, propargyl, butinyl, pentinyl, —$CF_3$, —$CHF_2$, —$CClF_2$, —$CF_2CHFCl$, —$CF_2CH_2F$, —$CF_2CHF_2$, —$CF_2CCl_3$, —$CH_2CF_3$, —$CF_2CHFCF_3$, —$CH_2CF_2CHF_2$, —$CH_2CF_2CF_3$, represents cyclopropyl, cyclobutyl, cyclopentyl, cyclohexyl, cyclopropylmethyl, cyclobutylmethyl, cyclopentylmethyl or cyclohexylmethyl, each of which is optionally mono- to trisubstituted by fluorine, chlorine, bromine, methyl, ethyl, n-propyl, isopropyl, n-butyl, isobutyl, sec-butyl, tert-butyl, ethenyl, 1-propenyl, 2,2-dimethylethenyl, —CH=$CCl_2$, phenyl, styryl, in each case fluorine-, chlorine- or bromine-substituted phenyl or 4-chlorostyryl, represents cyclopentenyl, cyclohexenyl, cyclohexenylmethyl or cyclopentenylmethyl, each of which is optionally substituted by fluorine, chlorine, methyl, ethyl, n-propyl, iso-propyl, n-butyl, isobutyl, sec-butyl or tert-butyl, represents benzyl, phenethyl, naphthylmethyl, tetrahydronaphthylmethyl, furylmethyl, thienylmethyl, pyrrolylmethyl, oxazolylmethyl, isoxazolylmethyl, thiazolylmethyl or pyridylmethyl, each of which is optionally mono- or disubstituted by nitro, fluorine, chlorine, bromine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, trifluoromethyl, trifluoromethoxy, difluoromethoxy or chlorodifluoromethoxy, represents —CO—$R^6$, —CO—$NR^7R^8$ or the grouping —$(CH_2)_p$—$(CR^9R^{10})_q$—$(CH_2)_r$—G.

Z and D together also very particularly preferably represent phenoxymethyl which is optionally mono- or disubstituted by nitro, fluorine, chlorine, bromine, methyl, ethyl, n-propyl, i-propyl, methoxy, ethoxy, n-propoxy, i-propoxy, trifluoromethyl, trifluoromethoxy, difluoromethoxy or chlorodifluoromethoxy.

Y very particularly preferably represents a direct bond, oxygen, sulphur, carbonyl, —$CH_2$—, —$(CH_2)_2$—, —CH=CH— (E or Z), —C/C—, —$CH_2O$—, —$(CH_2)_2O$—, —$CH(CH_3)O$—, —$OCH_2$—, —$O(CH_2)_2$—, —$SCH_2$—, —$S(CH_2)_2$—, —SCH($CH_3$)—, $C_1$-$C_4$-alkylenedioxy, in particular —$OCH_2O$— or —$O(CH_2)_2O$— or represents p-phenylene which is optionally monosubstituted by a radical from the list $W^1$.

E very particularly preferably represents hydrogen, methyl, ethyl, n-propyl, isopropyl, n-butyl, isobutyl, sec-butyl, tert-butyl, the isomeric pentyls, the isomeric hexyls, n-heptyl, n-octyl, n-isooctyl, n-nonyl, n-decyl, n-undecyl, n-dodecyl, n-tridecyl, n-tetradecyl, n-pentadecyl, n-hexadecyl, 2-propenyl, butenyl, pentenyl, hexenyl, propargyl, butinyl, pentinyl, —$CF_3$, —$CHF_2$, —$CClF_2$, —$CF_2CHFCl$, —$CF_2CH_2F$, —$CF_2CHF_2$, —$CF_2CCl_3$, —$CH_2CF_3$, —$CF_2CHFCF_3$, —$CH_2CF_2CHF_2$, —$CH_2CF_2CF_3$, represents cyclopropyl, cyclobutyl, cyclopentyl or cyclohexyl, each of which is optionally mono- to trisubstituted by fluorine, chlorine, bromine, methyl, ethyl, n-propyl, isopropyl, n-butyl, isobutyl, sec-butyl, tert-butyl, ethenyl, 1-propenyl, 2,2-dimethylethenyl, —CH=$CCl_2$, phenyl, styryl, in each case fluorine-, chlorine- or bromine-substituted phenyl or by 4-chlorostyryl, represents cyclopentenyl or cyclohexenyl, each of which is optionally substituted by fluorine, chlorine, methyl, ethyl, n-propyl, isopropyl, n-butyl, isobutyl, sec-butyl or tert-butyl, represents phenyl which is optionally mono- or disubstituted by radicals from the list $W^1$, represents furyl, thienyl, pyrrolyl, oxazolyl, isoxazolyl, thiazolyl or pyridyl, each of which is optionally mono- or disubstituted by radicals from the list $W^2$, or represents the grouping —$(CH_2)_p$—$(CR^9R^{10})_q$—$(CH_2)_r$—G.

$R^6$ very particularly preferably represents methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, cyclopropyl, cyclohexyl, cyclohexyloxy, cyclohexylmethyloxy, phenyl, 2-chlorophenyl, 3-chlorophenyl, 2,6-difluorophenyl, 2,4-dichlorophenyl, 3,4-dichlorophenyl, 2-trifluoromethoxyphenyl or 4-trifluoromethoxyphenyl.

$R^7$ very particularly preferably represents hydrogen.

$R^8$ very particularly preferably represents methyl, ethyl or phenyl which is optionally monosubstituted by chlorine.

p, q and r independently of one another each very particularly preferably represent 0, 1, 2 or 3, their sum being smaller than 4.

$R^9$ and $R^{10}$ independently of one another each very particularly preferably represent hydrogen, methyl, ethyl, n-propyl, isopropyl, n-butyl, isobutyl, sec-butyl, tert-butyl.

G very particularly preferably represents cyano, represents 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl, each of which is optionally mono- to trisubstituted by fluorine, chlorine, bromine, methyl, ethyl, n-propyl, isopropyl or trifluoromethyl and optionally, at the point of linkage, by the radical $R^{11}$, or represents one of the groupings below:

  (a)

  (b)

  (c)

  (d)

  (e)

  (f)

  (g)

  (h)

  (i)

$R^{11}$ very particularly preferably represents hydrogen, methyl, ethyl, n-propyl, isopropyl, n-butyl, isobutyl, sec-butyl, tert-butyl, the isomeric pentyls, the isomeric hexyls, —$CF_3$, —$CHF_2$, —$CClF_2$, —$CF_2CHFCl$, —$CF_2CH_2F$, —$CF_2CHF_2$, —$CF_2CCl_3$, —$CH_2CF_3$, $C_3$-$C_6$-alkenyl, $C_3$-$C_6$-alkenyl which is mono- to trisubstituted by fluorine or chlorine, represents cyclopropyl, cyclopentyl or cyclohexyl, each of which is optionally mono- or disubstituted by fluorine, chlorine, methyl, ethyl, n-propyl, isopropyl, —CF$_3$, —CHF$_2$, —CClF$_2$, —CF$_2$CHFCl, —CF$_2$CH$_2$F, —CF$_2$CHF$_2$, —CF$_2$CCl$_3$ or —CH$_2$CF$_3$, or represents phenyl which is optionally mono- or disubstituted by methylcarbonylamino, ethylcarbonylamino, methylcarbonyl-methylamino and/or radicals from the list W$^3$.

R$^{12}$ very particularly preferably represents hydrogen, methyl, ethyl, n-propyl, isopropyl, n-butyl, isobutyl, sec-butyl, tert-butyl, —CH$_2$CF$_3$, allyl, represents cyclopropyl, cyclopentyl, cyclohexyl, cyclopropylmethyl, cyclopentylmethyl, cyclohexylmethyl, cyclopropylethyl, cyclopentylethyl or cyclohexylethyl, each of which is optionally mono- or disubstituted by fluorine, chlorine, methyl, ethyl, n-propyl, isopropyl, —CF$_3$, —CHF$_2$, —CClF$_2$, —CF$_2$CHFCl, —CF$_2$CH$_2$F, —CF$_2$CHF$_2$, —CF$_2$CCl$_3$ or —CH$_2$CF$_3$, or represents benzyl or phenethyl, each of which is optionally mono- or disubstituted by radicals from the list W$^3$.

R$^{13}$ and R$^{14}$ independently of one another each very particularly preferably represent hydrogen, methyl, ethyl, n-propyl, isopropyl, n-butyl, isobutyl, sec-butyl, tert-butyl, —CH$_2$CF$_3$, methoxy, ethoxy, allyl, represent cyclopropyl, cyclopentyl, cyclohexyl, cyclopropylmethyl, cyclopentylmethyl or cyclohexylmethyl, each of which is optionally mono- or disubstituted by fluorine, chlorine, methyl, ethyl, n-propyl, isopropyl or trifluoromethyl, represent phenyl, benzyl or phenethyl, each of which is optionally mono- or disubstituted by radicals from the list W$^3$, represent —OR$^{12}$ or —NR$^{11}$R$^{12}$.

R$^{15}$ very particularly preferably represents —OR$^{12}$, —NR$^{11}$R$^{12}$ or —N(R$^{11}$)—COOR$^{12}$.

R$^{16}$, R$^{17}$ and R$^{18}$ independently of one another each very particularly preferably represent methyl, ethyl, n-propyl or isopropyl.

W$^1$ very particularly preferably represents hydrogen, fluorine, chlorine, bromine, cyano, formyl, nitro, methyl, ethyl, n-propyl, isopropyl, n-butyl, isobutyl, sec-butyl, tert-butyl, methoxy, ethoxy, n-propoxy, isopropoxy, n-butoxy, iso-butoxy, sec-butoxy, tert-butoxy, —CF$_3$, —CHF$_2$, —CClF$_2$, —CF$_2$CHFCl, —CF$_2$CH$_2$F, —CF$_2$CHF$_2$, —CF$_2$CCl$_3$, —CH$_2$CF$_3$, —CF$_2$CHFCF$_3$, —CH$_2$CF$_2$CHF$_2$, —CH$_2$CF$_2$CF$_3$, trifluoromethoxy, difluoromethoxy, chlorodifluoromethoxy, acetyl, propionyl, butyryl, isobutyryl, methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl or —S(O)$_o$R$^3$.

W$^2$ very particularly preferably represents fluorine, chlorine, bromine, cyano, methyl, ethyl, n-propyl, isopropyl, trifluoromethyl, trifluoromethoxy, difluoromethoxy, chlorodifluoromethoxy, acetyl, trifluoromethylthio, —CH=N—OCH$_3$, —CH=N—OC$_2$H$_5$, —CH=N—OC$_3$H$_7$, —C(CH$_3$)=N—OCH$_3$, —C(CH$_3$)=N—OC$_2$H$_5$, —C(CH$_3$)=N—OC$_3$H$_7$, —C(C$_2$H$_5$)=N—OCH$_3$, —C(C$_2$H$_5$)=N—OC$_2$H$_5$ or —C(C$_2$H$_5$)=N—OC$_3$H$_7$.

W$^3$ very particularly preferably represents fluorine, chlorine, cyano, nitro, methyl, ethyl, methoxy, ethoxy, methylthio, trifluoromethyl, trifluoromethoxy, trifluoromethylthio, dimethylamino, diethylamino, —COOR$^{19}$ or —CONR$^{20}$R$^{21}$.

R$^{19}$ very particularly preferably represents hydrogen, methyl, ethyl, n-propyl, isopropyl, tert-butyl, —CH$_2$CF$_3$, represents cyclopropyl, cyclopentyl or cyclohexyl, each of which is optionally mono- or disubstituted by fluorine, chlorine, methyl, ethyl, n-propyl, isopropyl or —CF$_3$, or represents phenyl which is optionally mono- or disubstituted by radicals from the list W$^4$.

R$^{20}$ and R$^{21}$ independently of one another each very particularly preferably represent hydrogen, methyl, ethyl, n-propyl, isopropyl, n-butyl, isobutyl, sec-butyl, tert-butyl, —CH$_2$CF$_3$, methoxy, ethoxy, allyl, represent cyclopropyl, cyclopentyl, cyclohexyl, cyclopropylmethyl, cyclopentylmethyl or cyclohexylmethyl, each of which is optionally mono- or disubstituted by fluorine or chlorine, represent phenyl, benzyl or phenethyl, each of which is optionally mono- or disubstituted by the radicals from the list W$^4$, represent —OR$^{16}$ or —NR$^{17}$R$^{18}$.

W$^4$ very particularly preferably represents fluorine, chlorine, bromine, cyano, nitro, methyl, ethyl, tert-butyl, methoxy, ethoxy, methylthio, trifluoromethyl, trifluoromethoxy or trifluoromethylthio.

Preference is furthermore given to compounds of the formula (I-a)

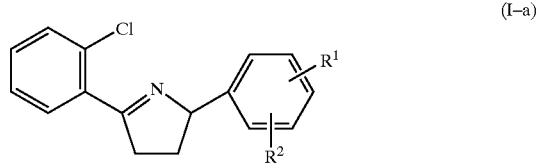

(I-a)

in which
R$^2$ has the general, preferred, particularly preferred or very particularly preferred meanings mentioned above,
R$^1$ represents hydrogen or phenyl which is mono- or disubstituted by radicals from the list W$^1$ or represents one of the groupings below

(m-b)
(I)

B represents p-phenylene which is optionally monosubstituted by a radical from the list W$^1$,
Y represents a direct bond or represents p-phenylene which is optionally mono- or disubstituted by radicals from the list W$^1$ and
D and E each have the very particularly preferred meanings mentioned above, where
G represents cyano or one of the groupings below

(a)
(e)

in which
R$^{11}$ and R$^{15}$ each have the general, preferred, particularly preferred or very particularly preferred meanings mentioned above and
W$^1$ has the general, preferred, particularly preferred or very particularly preferred meaning mentioned above.

Preference is furthermore given to compounds of the formula (I-f)

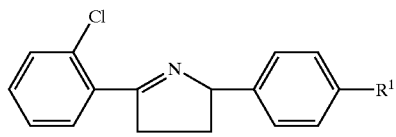

(I-f)

in which
R¹ represents hydrogen or
  a) phenyl which is mono- or disubstituted by radicals from the list W² or
  b) hetaryl (in particular furyl, thienyl, pyrrolyl, oxazolyl, isoxazolyl,
     thiazolyl or pyridyl, specifically thienyl) which is mono- or disubstituted by radicals from the list W².

Preference is furthermore given to compounds of the formula (I-g)

(I-g)

in which
Z represents hydrogen, fluorine, bromine, cyano, methyl, ethyl, n-propyl, isopropyl, trifluoromethyl, trifluoromethoxy, difluoromethoxy, chlorodifluoromethoxy, acetyl, trifluoromethylthio, —CH=N—OCH₃, —CH=N—OC₂H₅, —CH=N—OC₃H₇, —C(CH₃)=N—OCH₃, —C(CH₃)=N—OC₂H₅, —C(CH₃)=N—OCt3H₇, —C(C₂H₅)=N—OC₂H₅ or —C(C₂H₅)=N—OC₃H₇.

Preference is furthermore given to the compounds of the formula (I-f) listed in

TABLE 1

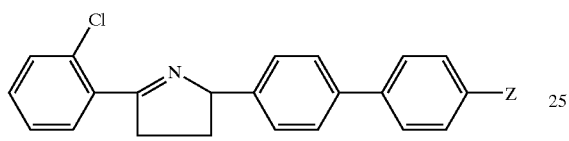

| Example No. | R¹ |
|---|---|
| I-1 | (4-isopropylphenyl) |
| I-2 | (3,5-dichlorophenyl) |
| I-3 | (4-fluorophenyl) |

TABLE 1-continued (I-f)

| Example No. | R¹ |
|---|---|
| I-4 | (4-chlorophenyl) |
| I-5 | (3-thienyl) |
| I-6 | (5-methylthien-2-yl CH=N—OCH₃) |
| I-7 | (4-OCF₃-phenyl) |
| I-8 | —Br |
| I-9 | (difluorobenzodioxol-methyl) |
| I-10 | (3-F, 4-OCF₃-phenyl) |
| I-11 | (3-CF₃-phenyl) |
| I-12 | (4-CF₃-phenyl) |
| I-13 | (2-CHO-phenyl) |
| I-14 | (4-CHO-phenyl) |
| I-15 | (4-COOH-phenyl) |
| I-16 | (2-CH₃, 3-F-phenyl) |

TABLE 1-continued
(I-f)
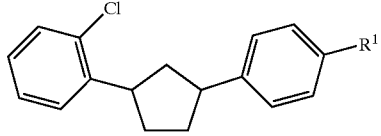
| Example No. | R¹ |
|---|---|
| I-17 | 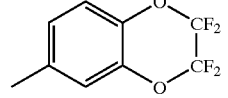 |
| I-18 | 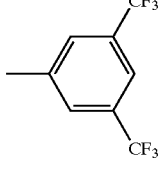 |
| I-19 | 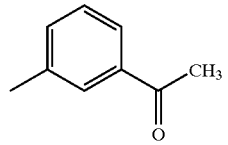 |
| I-20 | H |
| I-21 | 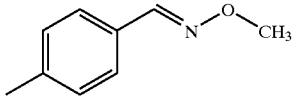 |
| I-22 | 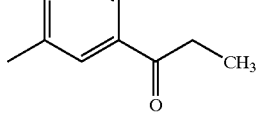 |
| I-23 | 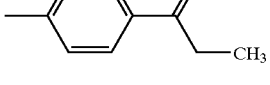 |
| I-24 | 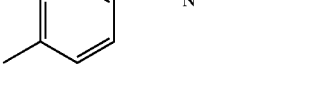 |
| I-25 | 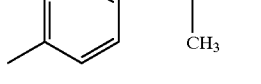 |
| I-26 | 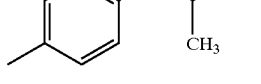 |
| I-27 | 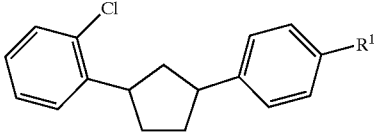 |
| I-28 | 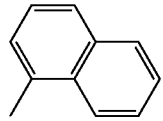 |
| I-29 | 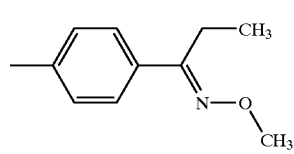 |
| I-30 | 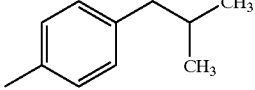 |
| I-31 | 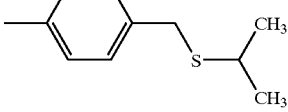 |
| I-32 | 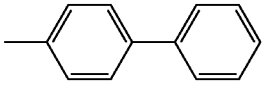 |
| I-33 |  |
| I-34 | 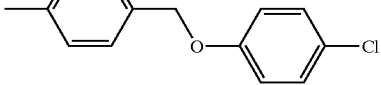 |
| I-35 | 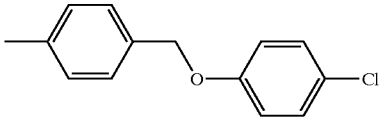 |
| I-36 | 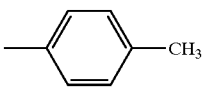 |
| I-37 | 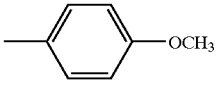 |
| I-38 | |

TABLE 1-continued (I-f)

![structure with Cl-phenyl and R1-phenyl on cyclopentane]

| Example No. | R¹ |
|---|---|
| I-39 | ![4-acetyl-phenyl, CH3] |
| I-40 | —(CH$_2$)$_3$—CH$_3$ |
| I-41 | ![4-bromo-phenyl] |
| I-42 | ![4-SCF3-phenyl] |
| I-43 | ![phenyl-O-CF2-CF2-H] |

The abovementioned general or preferred radical definitions or illustrations can be combined with one another at will, i.e. including combinations between the respective ranges and preferred ranges. They apply both to the end products and also, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Saturated or unsaturated hydrocarbon radicals such as alkyl or alkenyl can in each case be straight-chain or branched as far as this is possible, even in combination with heteroatoms, such as, for example, in alkoxy.

Optionally substituted radicals can be mono- or polysubstituted and, in the case of polysubstitution, the substituents can be identical or different. A plurality of radicals having the same indices, such as, for example, m radicals R² for m>1, can be identical or different.

Using, for example, tBOC-[1-(4-ethyl-2-methyl-phenyl)-3-(2-chlorophenyl-carboxyl)-1-propyl]-amine as starting material, the course of the reaction of the process (A) a) according to the invention can be represented by the following equation:

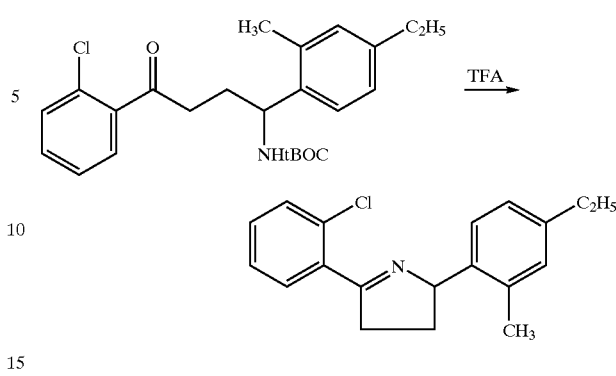

Using, for example, 1-(4-ethyl-2-methyl-phenyl)-1-nitro-3-(2-chlorophenylcarboxyl)-propane as starting material, the course of the reaction of the process (A) b) according to the invention can be represented by the following equation:

![reaction scheme showing nitro compound converting via NH2 intermediate to cyclic imine]

Using, for example, 1-(4-ethyl-2-methyl-phenyl)-1-(diphenylmethyleneimino)-3-(2-chlorophenylcarboxyl)-propane as starting material, the course of the reaction of the process (A) c) according to the invention can be represented by the following equation:

![reaction scheme showing NO2 and NH2 intermediates]

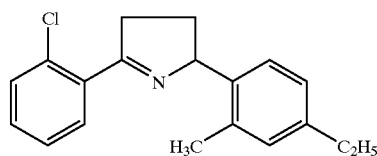
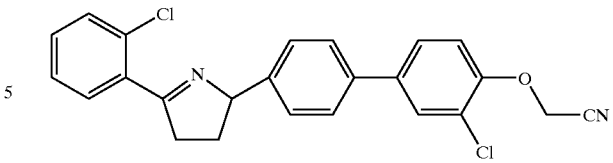

Using, for example, 2-(4-methoxyphenyl)-cyclobutane-O-methanesulfonyloxime and 2-chlorophenylmagnesium bromide as starting materials, the course of the reaction of the process (B) according to the invention can be represented by the following equation:

Using, for example, 2-(2-chloro-phenyl)-5-(3'-chloro-4'-hydroxybiphenyl-4-yl)-3,4-dihydro-2H-pyrrole and methyl α-bromovalerate as starting materials, the course of the reaction of the process (D) according to the invention can be represented by the following equation:

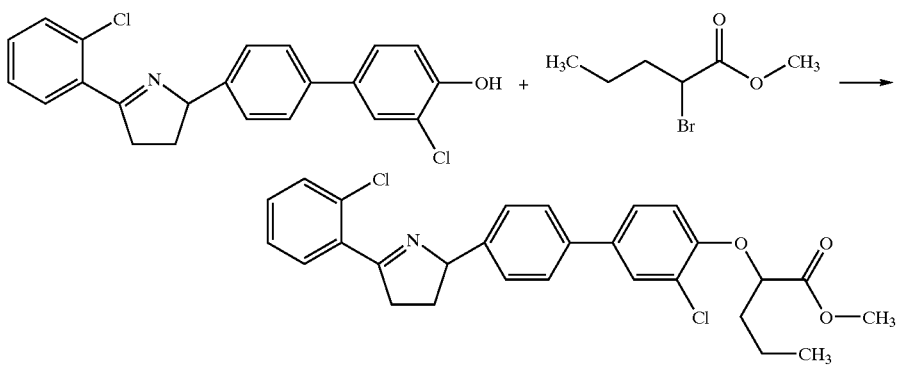

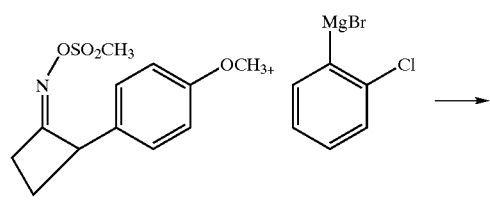

Using, for example, 5-(4'-cyclopropylcarbonylmethoxy-3-trifluoromethoxy-biphenyl-4-yl)-2-(2-chlorophenyl)-3,4-dihydro-2H-pyrrole and O-methylhydroxylamine as starting materials, the course of the reaction of the process (E) according to the invention can be represented by the following equation:

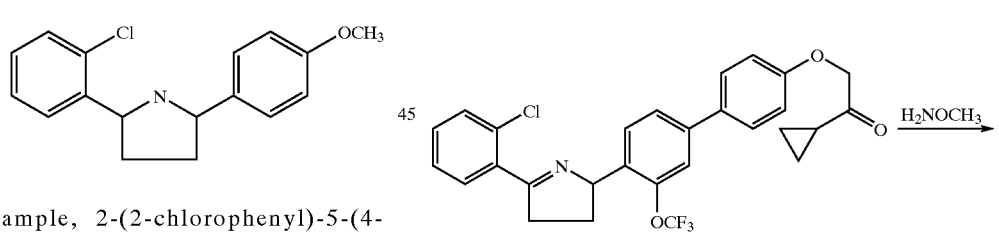

Using, for example, 2-(2-chlorophenyl)-5-(4-iodophenyl)-3,4-dihydro-2H-pyrrole and 4-cyanomethoxyphenyl boronic acid as starting materials, the course of the reaction of the process (C) according to the invention can be represented by the following equation:

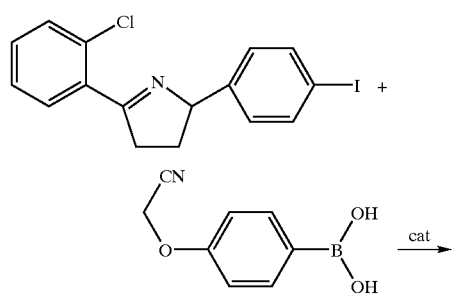
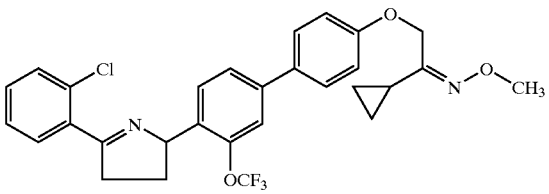

Using, for example, 4-bromobenzylcyanide, the course of the reaction of the process (F) according to the invention can be represented by the following equation:

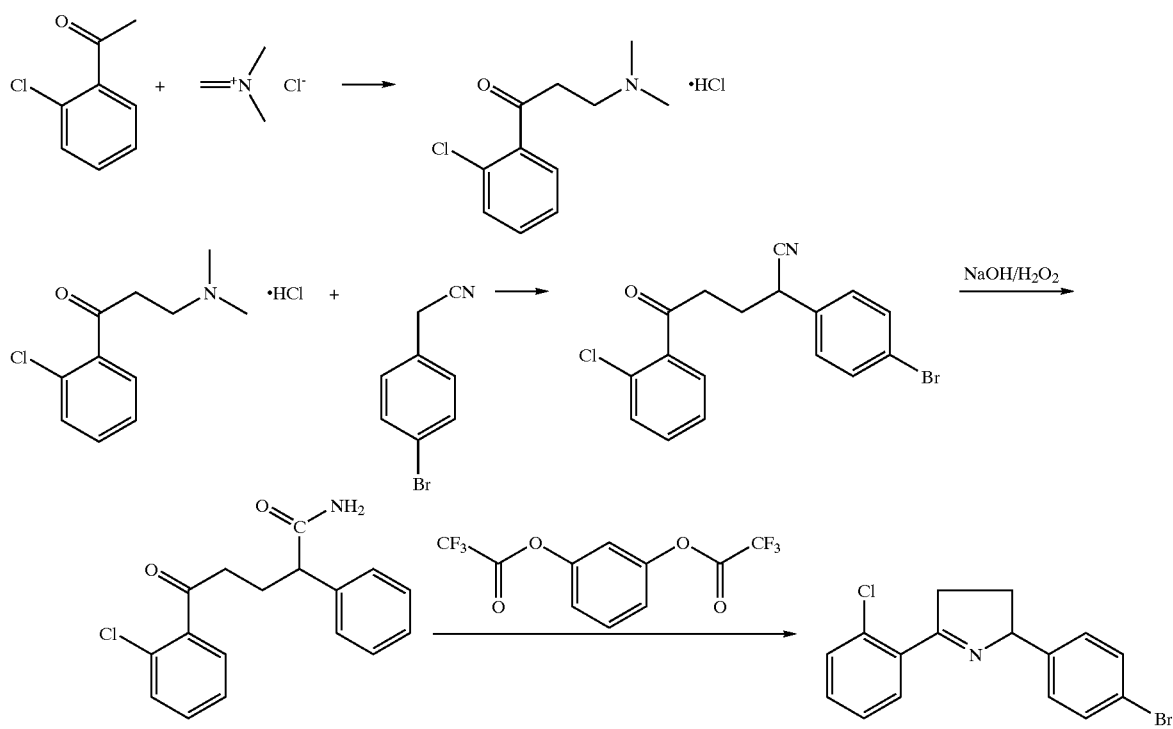

Using, for example, 5-phenylpyrrolidin-2-one, the course of the process (G) according to the invention can be represented by the following equation:

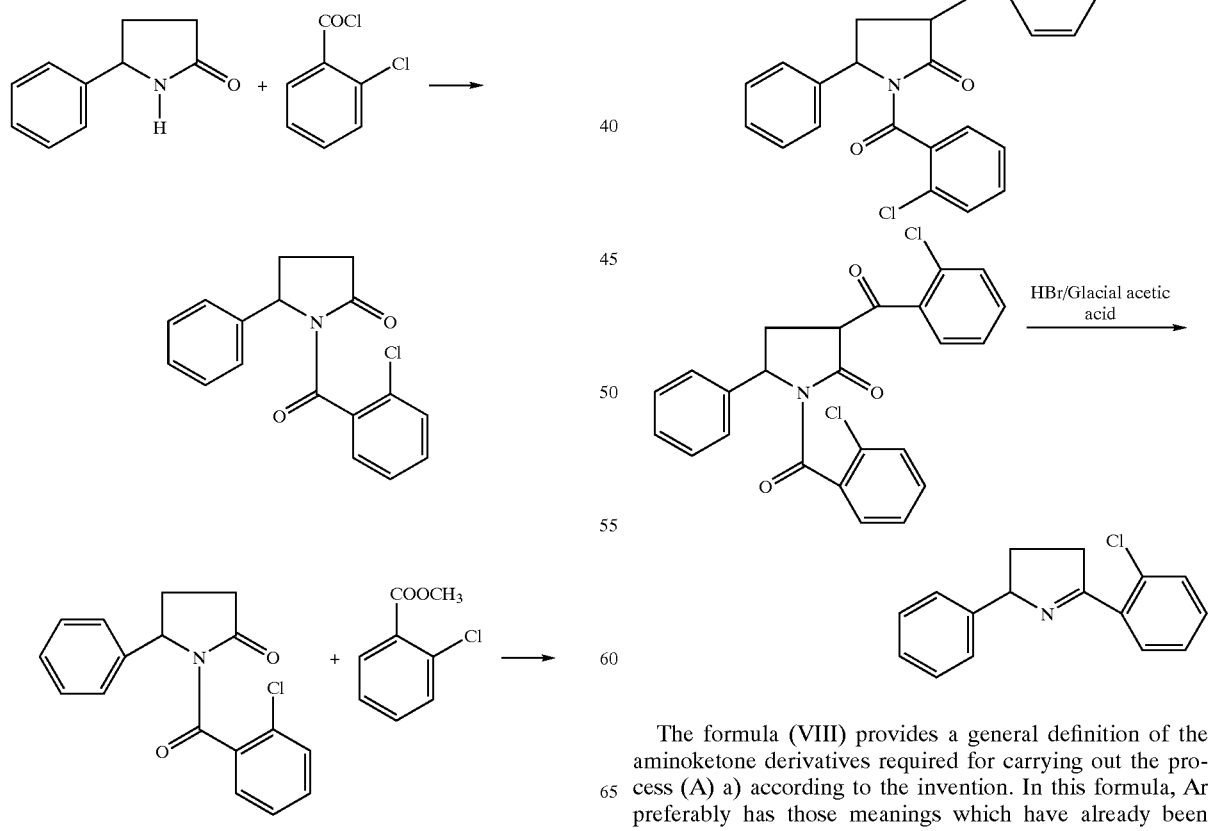

The formula (VIII) provides a general definition of the aminoketone derivatives required for carrying out the process (A) a) according to the invention. In this formula, Ar preferably has those meanings which have already been mentioned in connection with the description of the cyclic imines of the formula (I) as being preferred. The aminoketone derivatives of the formula (VIII) are novel.

Aminoketone derivatives of the formula (VIII) can be prepared, for example, by reacting BOC-protected lactams of the formula (IX) with metal lated aromatics of the formula (X) at temperatures between 0° C. and 80° C., in accordance with the following equation:

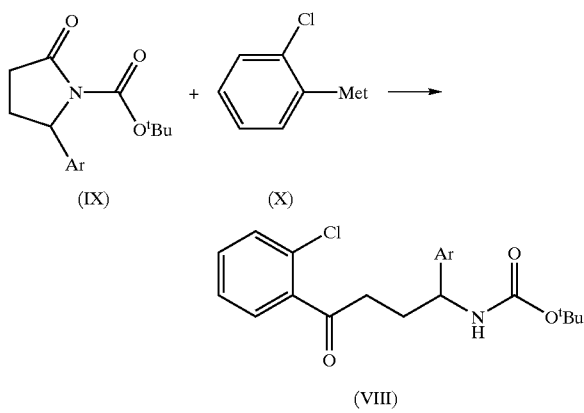

In the formula (X), Met represents a monovalent metal radical such as Li, MgI, MgBr or MgCl.

Some metallated aromatics of the formula (X) are known, or they can be prepared by known methods, such as, for example, lithiation or Grignard reaction, from the corresponding aromatics or halogeno aromatics.

Protected lactams of the formula (IX) are obtained, for example, by BOC-protecting lactams of the formula (XI) using customary methods, such as, for example, metallation with butyl lithium and reaction with di-tert-butyl dicarbonate (cf., for example, T. W. Greene, P. G. M. Wuts, Protective Groups in Organic Synthesis, 2nd Ed., John Wiley & Sons, New York 1991).

Lactams of the formula (XI) can be prepared starting, for example, with ω-alkoxylactams of the formula (XII), by two methods. The ω-alkoxylactams can be reacted with aromatics of the formula (XIII) in the presence of an acidic catalyst, such as, for example, sulphuric acid, acetic acid or aluminium chloride and, if appropriate, in the presence of a diluent, such as, for example, dichloromethane or acetonitrile, in accordance with the following equation:

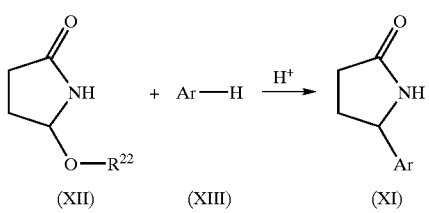

Alternatively, they can be reacted with aryl Grignard compounds of the formula (XIV) in the presence of a diluent, such as, for example, tetrahydrofuran, in accordance with the following equation [cf. Org. Prep. Proced. Int. 25, 255 (1993)]:

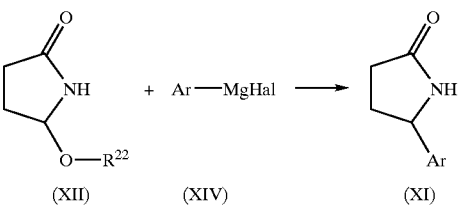

In formula (XII), $R^{22}$ represents methyl or ethyl. In the formula (XIV), Hal represents chlorine, bromine or iodine.

The ω-alkoxylactams of the formula (XII) are known, some of them are commercially available, and they can be prepared, for example, from the corresponding unsubstituted imides by cathodic or sodium borohydrite reduction, or from the unsubstituted lactams by anodic oxidation, in each case in the presence of methanol or ethanol (cf., for example, J. Org. Chem. 56, 1822 (1991); Synthesis 1980, 315).

The aromatics of the formula (XIII) are benzene derivatives which are generally known or which can be prepared using a wide choice of generally known methods of organic chemistry.

The aryl Grignard compounds of the formula (XIV) can be prepared in a customary manner from the corresponding aryl halides and magnesium. Aryl halides are generally known compounds of organic chemistry.

Lactams of the formula (XI) can also be prepared, for example, by cyclizing substituted ω-benzoylcarboxylic acids of the formula (XV) with a reagent prepared from ammonium carbonate and formic acid at boiling point, in accordance with the following reaction scheme [cf. Recl. Trav. Chim. Pays-Bas 81, 788 (1962)]:

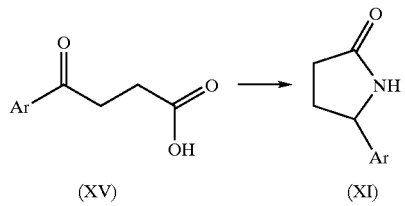

The ω-benzoylcarboxylic acids of the formula (XV) required for this purpose can be prepared, for example, by reacting the dicarboxylic anhydrides of the formula (XVI) with aromatics of the formula (XIII) in the presence of a Lewis acid, such as, for example, aluminium chloride, and, if appropriate, in the presence of a diluent, such as, for example, benzene, in accordance with the following equation [cf. Recl. Trav. Chim. Pays-Bas 81, 788 (1962)]:

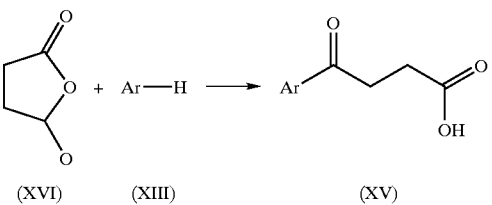

The anhydride (succinic anhydride) required for this purpose is commercially available.

Starting from the lactams of the formula (XI), all process steps up to the preparation of the cyclic imines of the formula (I), including the cyclocondensation according to process A a), can also be carried out as a "one-pot reaction".

If Ar in the active compound of the formula (I) according to the invention as in the formula (I-b) shown above represents an optionally substituted biphenylyl, the corresponding biphenyl lactams of the formula (XI-a) can be prepared in an advantageous variant of the process described here by reacting, similarly to the process (C) described above and below, certain phenyl lactams of the formula (XVII) with boronic acids of the formula (VI) in accordance with the following equation:

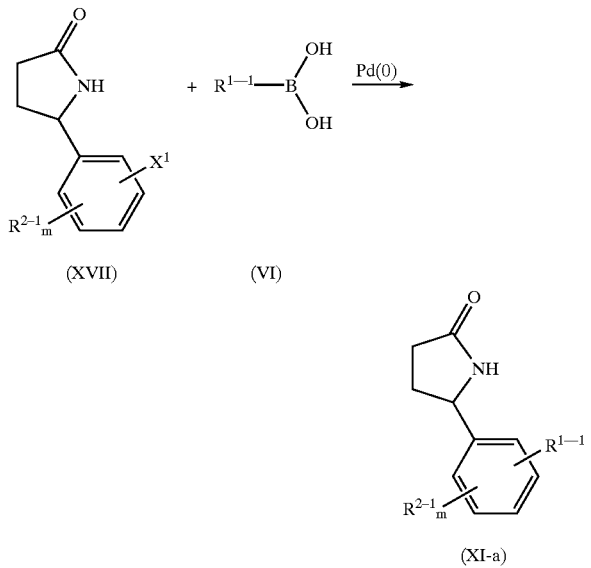

The phenyl lactams of the formula (XVII) in which $X^1$ represents bromine or iodine are a subset of the compounds of the formula (XI) whose preparation is mentioned above. The phenyl lactams of the formula (XVII) in which $X^1$ represents trifluoromethanesulphonyl can be prepared analogously to the route described for process (C) from the corresponding compounds of the formula (XI) in which Ar is substituted by $R^1$=hydroxyl.

The formula (XVIII) provides a general definition of the nitroketones required for carrying out the process A) b). In this formula, Ar preferably has those meanings which have already been mentioned in connection with the description of the cyclic imines of the formula (I) as being preferred. The nitroketones of the formula (XVIII) are novel.

Nitroketones of the formula (XVIII) can be prepared, for example, by condensing the ω-chloroalkyl phenyl ketone of the formula (XXI) in the presence of a diluent, such as, for example, methanol, ethanol, another lower aliphatic alcohol or else tetrahydrofuran, and in the presence of an acid binder, such as, for example, sodium hydride or an alkali metal alkoxide, preferably of the corresponding alcohol which is used as diluent, in accordance with the following equation:

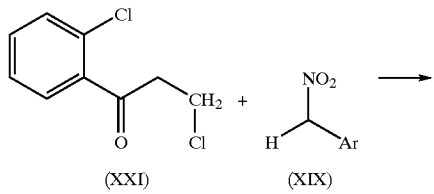

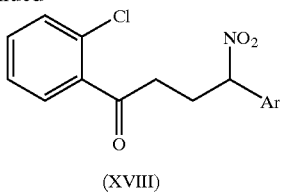

The ω-chloroalkyl phenyl ketone of the formula (XXI) can be prepared in a known manner, such as, for example, by Friedel-Crafts acylation of chlorobenzene of the formula (XXII) (see below) with 3-chloropropionyl chloride.

The nitromethyl benzenes of the formula (XIX) are known or can be prepared in a known manner, such as, for example, by side-chain nitration of corresponding toluenes, or by reacting corresponding benzyl halides with silver nitrite [cf., for example, J. Am. Chem. Soc. 77, 6269 (1955); J. Am. Chem. Soc 86, 2681 (1964); Houben-Weyl, Methoden der Organischen Chemie, Georg Thieme Verlag Stuttgart, volume 10/1, 46–57 (halogen substitution), volume E16, 145–154 (both methods)]. The toluenes or benzyl halides required for this purpose are generally known compounds of organic chemistry.

The nitroketones of the formula (XVIII) can be prepared, for example, by Michael additions of nitromethylbenzenes of the formula (XIX) to phenyl vinyl ketone of the formula (XX) in the presence of a diluent, such as, for example, methanol, ethanol or another lower aliphatic alcohol, and in the presence of an acid binder, such as, for example, preferably an alkali metal alkoxide of the corresponding alcohol which is used as diluent, in accordance with the following equation (cf., for example, J. Prakt. Chem., Series 4, 1, 57 (1955); Houben-Weyl, Methoden der Organischen Chemie, Georg Thieme Verlag Stuttgart, volume 10/1, 199–206):

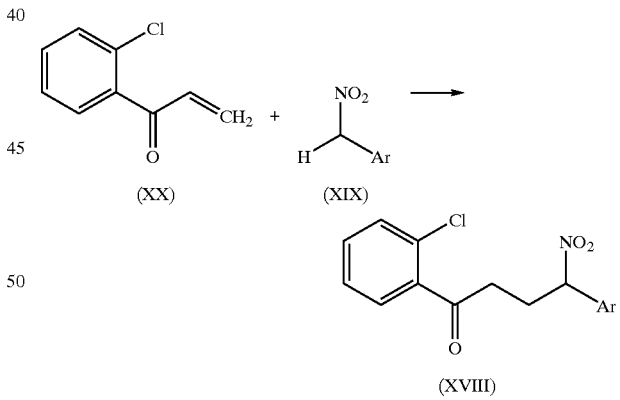

The phenyl vinyl ketone of the formula (XX) can be prepared, for example, by eliminating hydrogen chloride from β-chloropropiophenone of the formula (XXI), which can be obtained, for example, by Friedel-Crafts acylation of chlorobenzene of the formula (XXII) with 3-chloropropionyl chloride, said elimination being carried out in the presence of an acid binder, such as, for example, potassium acetate, and in the presence of a diluent, such as, for example, methanol, in accordance with the following equation [cf., for example, J. Prakt. Chem., Series 4, 1, 57 (1955)]:

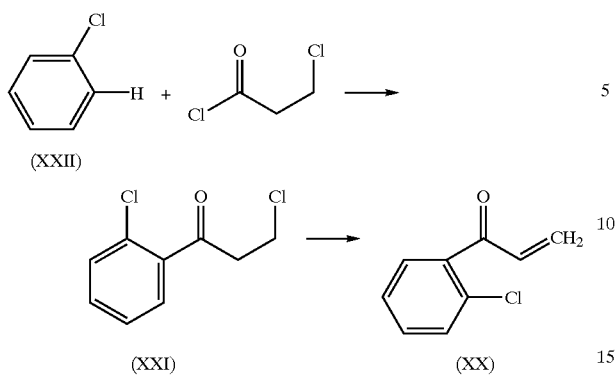

Chlorobenzenes of the formula (XXII) are commercially available.

The phenyl vinyl ketone of the formula (XX) can also be prepared by reacting O-methyl methyl-2-chloro-benzohydroxamate of the formula (XXIII) with vinyl magnesium bromide, in accordance with the following equation:

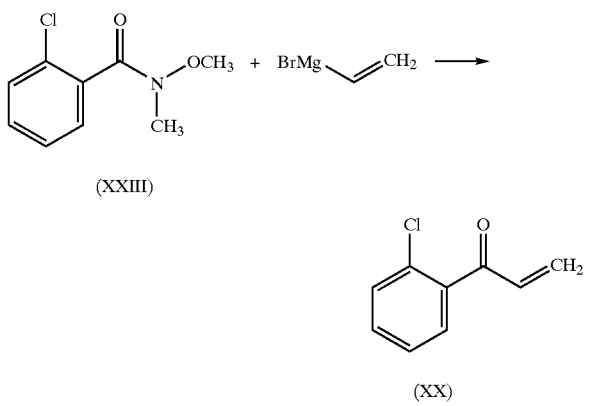

The O-methyl methyl-2-chloro-benzohydroxamate of the formula (XXIII) can be prepared by known methods, for example from the corresponding benzoic acid derivatives [cf., for example, Tetrahedron Lett. 22, 3815 (1981)].

Since the phenyl vinyl ketone of the formula (XX) is sensitive, it is, in a preferred variant for preparing the nitroketones of the formula (XVIII), directly reacted further with nitromethylbenzenes of the formula (XIX).

Nitroketones of the formula (XVIII) can also be prepared by adding, in accordance with the equation below, enamines of methyl phenyl ketones of the formula (XXVI) to α-nitrostyrenes of the formula (XXVII) and subjecting the reaction product to an acidic hydrolysis:

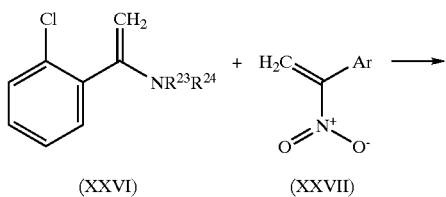

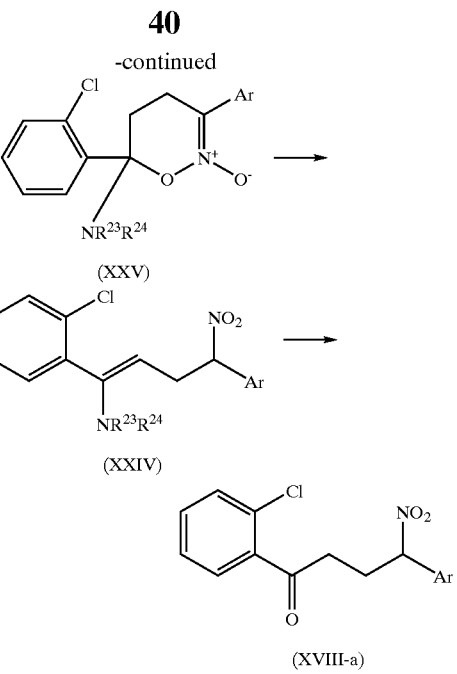

In the formulae (XXIV), (XXV) and (XXVI), $R^{23}$ and $R^{24}$ together with the linking nitrogen atom represent a cyclic amino radical, such as, for example, 1-pyrrolidino, 1-piperidino or 4-morpholino.

In most cases, the addition proceeds in a [4+2]-cycloaddition to give isolatable 1,2-oxazine -N-oxide derivatives of the formula (XXV), and it is, if appropriate, carried out in the presence of a non-polar diluent, such as, for example, diethyl ether, at, for example, from −80° to +20° C. For the hydrolysis, use is made, for example, of aqueous mineral acids, such as hydrochloric acid, if appropriate in the presence of methanol or ethanol [cf. for example, Helv. Chim. Acta 68, 162 (1985); Tetrahedron 45, 2099 (1989)]. In many cases, it is advantageous to open the ring first to give compounds of the formula (XXIV), by simply dissolving the 1,2-oxazine-N-oxide derivative in methanol or ethanol, since otherwise the undesirable Nef reaction, which gives the corresponding diketo compound, occurs as a competing reaction [cf., for example, Tetrahedron 45, 2099 (1989)].

Some of the enamines of the formula (XXVI) are known, or they can be prepared, for example, from the correspondingly substituted acetophenones and the cyclic amines using standard methods (for example Org. Syntheses Vol. 58, 56, John Wiley & Sons, New York). Some of the acetophenones required for this purpose are commercially available or known, or they can be prepared by known methods of the chemistry of aromatics.

Some of the nitrostyrenes of the formula (XXVII) are known, or they can be prepared, for example, by formylation of the nitromethylbenzenes of the formula (XIX) given above (cf., for example, Houben-Weyl, Methoden der Organischen Chemie, Georg Thieme Verlag, Stuttgart, volume E16, 215).

The formula (XXVIII) provides a general definition of the imines required for carrying out the process A) c). In this formula, Ar preferably has those meanings which have already been mentioned in connection with the description of the cyclic imines of the formula (I) as being preferred.

The imines of the formula (XXVIII) can be prepared, for example, by carrying out Michael additions of N-diphenylmethylenebenzylamines of the formula (XXIX)

to the phenyl vinyl ketone of the formula (XX), in accordance with the following equation:

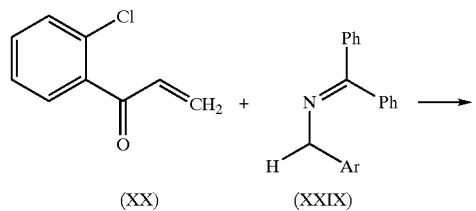

(XX)  (XXIX)

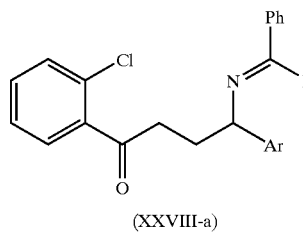

(XXVIII-a)

The addition is carried out in the presence of an acid binder and in the presence of a diluent, such as, for example, acetonitrile or dichloromethane, and, if appropriate, in the presence of a reaction auxiliary, for example at room temperature. A preferred acid binder is aqueous alkali, such as 50% strength aqueous sodium hydroxide solution in the presence of a phase-transfer catalyst, such as, for example, triethylbenzylammonium chloride as reaction auxiliary [cf., for example, Synth. Commun.17, 211 (1987)].

The preparation of the phenyl vinyl ketone of the formula (XX) is described above. The N-diphenylmethylene benzylamines of the formula (XXIX) are obtained, for example, by reacting the corresponding benzylamines with benzophenone (cf. for example, Tetrahedron. Lett. 1978, 2641). The benzylamines required for this purpose are known, or they can be prepared by known methods, such as, for example, aminolysis of the corresponding benzyl halides (see above).

The formula (III) provides a general definition of the cyclic O-methanesulphonyl oximes required for carrying out the process (B) according to the invention. In this formula, Ar preferably has those meanings which have already been mentioned in connection with the description of the cyclic imines of the formula (1) as being preferred. The O-methanesulphonyl oximes of the formula (III) are novel.

The O-methylsulphonyl oximes of the formula (III) can be prepared by, for example according to the equation below, initially converting cyclic α-aryl ketones of the formula (XXXI) by generally known methods into their oximes of the formula (XXX) and subsequently reacting these with methanesulphonyl chloride, similarly to the mesylation of alcohols:

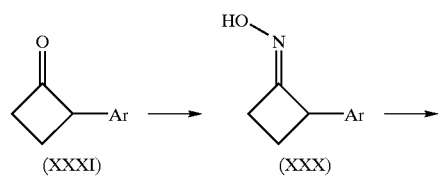

(XXXI)  (XXX)

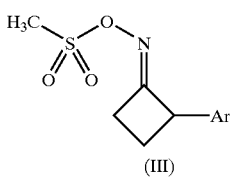

(III)

Cyclic α-aryl ketones of the formula (XXXI) can be prepared, for example, by epoxidizing 1-arylcycloalkenes of the formula (XXXIII) according to the equation below by customary methods, such as, for example, with m-chloroperbenzoic acid, to give oxirans of the formula (XXXII) and subsequently isomerizing these by acidic work-up [cf., for example, Tetrahedron 30, 2027 (1974)]:

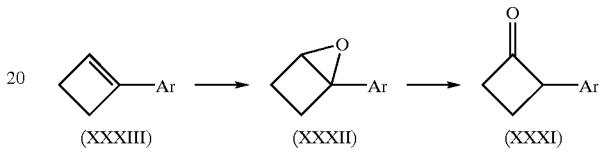

(XXXIII)  (XXXII)  (XXXI)

It is, of course, also possible to isomerize oxirans of the formula (XXXII) obtained by other routes to give cyclic α-aryl ketones of the formula (XXXI), for example by shaking a solution in chloroform with 20% strength sulphuric acid.

1-Arylcycloalkenes of the formula (XXXIII) can be prepared, for example, by reacting according to the equation below the aryl Grignard compounds of the formula (XIV) described above with cyclobutanone of the formula (XXXV) under customary Grignard conditions and dehydrating the cyclic benzyl alcohols of the formula (XXXIV) which have been obtained, for example, in this manner:

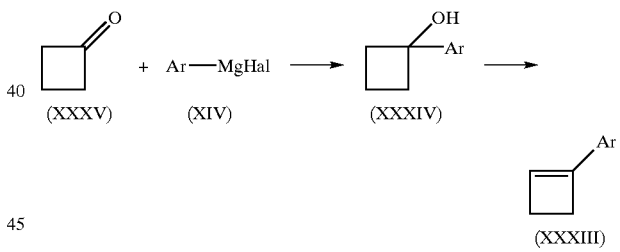

The dehydration can be carried out, for example, by dissolving the alcohol in a solvent of low polarity, such as hexane, and stirring with semi-concentrated sulphuric acid, for example at from 0° C. to 20° C. [cf., for example, Tetrahedron 30, 2027 (1974)].

Cyclobutanone of the formula (XXXV) is commercially available. The formula (IV) provides a definition of the aryl Grignard compounds furthermore required for carrying out the process (B) according to the invention.

Aryl Grignard compounds of the formula (IV) can be prepared from appropriate aryl halides and magnesium by the Grignard reaction. Aryl halides are generally known compounds of organic chemistry.

The cyclic imines of the formula (V) required for carrying out the process (C) according to the invention are, if $X^1$ represents bromine or iodine, a subset of the compounds of the general formula (I) according to the invention, and they can be prepared, for example, by the processes (A) and (B).

If $X^1$ represents trifluoromethanesulphonyl, the compounds of the formula (V-a) can be prepared by reacting hydroxyl compounds of the formula (I-f), which can also be prepared by the processes (A) and (B), with trifluoromethanesulphonyl chloride or trifluoromethanesulphonic anhydride in the presence of an acid binder, such as, for example, pyridine, and, if appropriate, in the presence of a diluent, in accordance with the following equation:

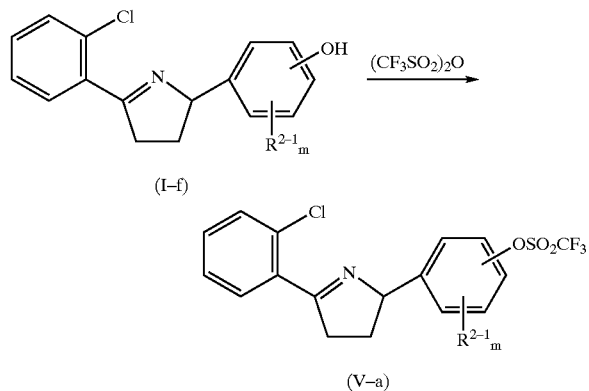

The formula (VI) provides a general definition of the boronic acids likewise required for carrying out the process (C) according to the invention. In this formula, $R^{1-1}$ preferably has those meanings which have already been mentioned in connection with the description of the cyclic imines of the formula (I-b) as being preferred.

Aromatic boronic acids of the formula (VI) are known or can be prepared by known methods [c.f. Chem. Rev. 45, 2457 (1995); Pure Appl. Chem. 66, 213 (1994)].

The cyclic imines of the formula (I-d) required for carrying out the process (D) according to the invention are a subset of the compounds of the general formula (I) according to the invention, and they can be prepared, for example, by processes (A) to (C).

The formula (VII) provides a definition of the compounds furthermore required for carrying out the process (D) according to the invention. In this formula, $R^9$, $R^{10}$, G, p, q and r each preferably have those meanings which have already been mentioned in connection with the description of the cyclic imines of the formula (I) as being preferred. Ab represents a customary leaving group, such as, for example, halogen, in particular chlorine or bromine; alkylsulphonyloxy, in particular methylsulphonyloxy; or optionally substituted arenesulphonyloxy, in particular phenylsulphonyloxy, p-chlorophenylsulphonyloxy or p-tolylsulphonyloxy.

The compounds of the formula (VII) are generally known compounds of organic chemistry.

The compounds of the formulae (F-I), (F-II), (F-IV) and (F-VII) furthermore required for carrying out the process (F) according to the invention are generally known compounds of organic chemistry.

The o-chlorobenzoyl chloride and methyl o-chlorobenzoate required for carrying out the process (G) according to the invention are commercially available.

Suitable acids for carrying out the process A) a) according to the invention are organic or inorganic Bronstedt acids, such as, for example, hydrogen fluoride, hydrogen chloride, sulphuric acid, phosphoric acid, formic acid, acetic acid, benzoic acid, citric acid, trifluoroacetic acid, methanesulphonic acid, trifluoromethanesulphonic acid or toluenesulphonic acid.

Particularly suitable is the acidolysis with trifluoroacetic acid, which is usually employed for cleaving off the tert-butoxycarbonyl amino protecting group (c.f., for example, T. W. Greene, P. G. M. Wuts, Protective Groups in Organic Synthesis, 2nd Ed., John Wiley & Sons, New York 1991).

The process (A) a) according to the invention is, if appropriate, carried out in the presence of a suitable acid acceptor. Suitable acid acceptors are all customary inorganic or organic bases. These preferably include alkaline earth metal or alkali metal hydroxides, amides, alkoxides, acetates, carbonates or bicarbonates, such as, for example, sodium hydroxide, potassium hydroxide or ammonium hydroxide, sodium amide, lithium diisopropylamide, sodium methoxide, sodium ethoxide, potassium tert-butoxide, sodium acetate, potassium acetate, calcium acetate or ammonium acetate, sodium carbonate, potassium carbonate or ammonium carbonate, sodium bicarbonate or potassium bicarbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process (A) a) according to the invention is, if appropriate, carried out in the presence of a diluent. Suitable diluents are water, organic solvents and mixtures of these. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole, ketones, such as acetone, butanone, methyl isobutyl ketone or cyclohexanone; nitriles, such as acetonitrile, propionitrile, n- or i-butyronitrile or benzonitrile; amides, such as fornamide, N,N-dimethylformamide, N,N-dimethylacetamide, N-methylformanilide, N-methylpyrrolidone or hexamethylphosphoric triamide; N-oxides, such as N-methylmorpholine N-oxide; esters, such as methyl acetate, ethyl acetate or butyl acetate; sulphoxides, such as dimethyl sulphoxide; sulphones, such as sulpholane, alcohols, such as methanol, ethanol, n- or i-propanol, N-, iso-, sec- or tert-butanol, ethanediol, propane-1,2-diol, ethoxyethanol, methoxyethanol, diethylene glycol monomethyl ether, diethylene glycol monoethyl ether.

The reaction temperature for the process (A) a) according to the invention can be varied within a relatively wide range. In general, the reaction is carried out at temperatures between −50° C. and +150° C., preferably between −20° C. and +100° C.

When carrying out the process A) a), an excess of acid is generally employed.

The process A) b) according to the invention is carried out as a catalytic hydrogenation or using other generally known methods for reducing nitro groups (cf., for example, Houben-Weyl, Methoden der Organischen Chemie, Georg Thieme Verlag Stuttgart, volume 11/1, 394–409 and volume 4/1c, 490–506).

The process A) c) according to the invention is carried out as a hydrolysis according to generally known methods, for example using aqueous hydrochloric acid.

Suitable diluents for carrying out the processes A) b) and A) c) are the diluents mentioned above for the process A) a).

Suitable diluents for carrying out the process (B) according to the invention are inert organic solvents and mixtures of these. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole.

Preference is given to using a solution of the Grignard compound of the formula (IV) in an ether and a solution of the O-methylsulphonyloxime of the formula (III) in a hydrocarbon.

The reaction temperature for the process (B) according to the invention can be varied within a relatively wide range. In general, the reaction is carried out at temperatures between −100° C. and +50° C., preferably between −80° C. and +30° C.

When carrying out the process (B) according to the invention, the Grignard compounds of the formula (IV) and the O-methylsulphonyl oxime of the formula (III) are employed in a molar ratio of from 1:1 to 3:1, preferably from 1:1 to 2:1.

Suitable catalysts for carrying out the process (C) according to the invention are palladium (0) complexes. Preference is given, for example, to tetrakis(triphenylphosphine) palladium.

Suitable acid acceptors for carrying out the process (C) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example, caesium fluoride, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process (C) according to the invention are water, organic solvents and mixtures of these. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether.

The reaction temperature for the process (C) according to the invention can be varied within a relatively wide range. In general, the reaction is carried out at temperatures between 0° C. and +140° C., preferably between 50° C. and +100° C.

When carrying out the process (C) according to the invention, the boronic acids of the formula (VI) and the compounds of the formula (V) are employed in a molar ratio of from 1:1 to 3:1, preferably from 1:1 to 2:1. The catalyst is generally employed in amounts of from 0.005 to 0.5 mol, preferably 0.01 mol to 0.1 mol, per mole of the compound of the formula (V). In general, an excess of base is employed.

The process (D) according to the invention is preferably carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium hydroxide, potassium hydroxide or ammonium hydroxide, sodium amide, lithium diisopropylamide, sodium methoxide, sodium ethoxide, potassium tert-butoxide, sodium acetate, potassium acetate, calcium acetate or ammonium acetate, sodium carbonate, potassium carbonate or ammonium carbonate, sodium bicarbonate or potassium bicarbonate and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process (D) according to the invention can be carried out in the presence of a suitable phase-transfer catalyst. Examples of such catalysts include: tetrabutylammonium iodide, tetrabutylammonium bromide or tetrabutylammonium chloride, tributylmethylphosphonium bromide, trimethyl-$C_{13}/C_{15}$-alkylammonium chloride or trimethyl-$C_{13}/C_{15}$-alkyl ammonium bromide, dibenzyldimethylammonium methyl sulphate, dimethyl-$C_{12}/C_{14}$-alkylbenzylammonium chloride, 15-crown-5,18-crown-6 or tris-[2-(2-methoxyethoxy)-ethyl]-amine.

The process (D) according to the invention is preferably carried out in the presence of a diluent. Suitable diluents are, for example, all solvents listed for process (A).

The reaction temperature for the process (D) according to the invention can be varied within a relatively wide range. In general, the reaction is carried out at temperatures between −20° C. and +100° C., preferably between 0° C. and 60° C.

When carrying out the process (D) according to the invention, in general approximately equimolar amounts of the starting materials are employed. However, it is also possible to use an excess of the compound of the formula (VII).

The reactions in accordance with the process E) according to the invention are derivatization reactions known to the person skilled in the art, in particular of carboxylic esters and ketones (cf., for example, Houben-Weyl, Methoden der Organischen Chemie, Georg Thieme Verlag, Stuttgart, vol. VII/2b, in particular 1912 ff; vol. VIII about carboxylic esters and their derivatives; vol. E5, in particular p. 812 ff. and the literature quoted therein).

The steps of the process (F) according to the invention are, if appropriate, carried out in the presence of a diluent. Suitable diluents are water (not for F, α), organic solvents and mixtures of these. Examples include: aliphatic, alicyclic or aromatic hydrocarbons, such as, for example, petroleum ether, hexane, heptane, cyclohexane, methylcyclohexane, benzene, toluene, xylene or decalin, halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; ketones, such as acetone, butanone, methyl isobutyl ketone or cyclohexanone; nitriles, such as acetonitrile, propionitrile, n- or i-butyronitrile or benzonitrile; amides, such as formamide, N,N-dimethylformamide, N,N-dimethylacetamide, N-methylformanilide, N-methylpyrrolidone or hexamethylphosphoric triamide; N-oxides, such as N-methylmorpholine N-oxide; esters, such as methyl acetate, ethyl acetate or butyl acetate; sulphoxides, such as dimethyl sulphoxide; sulphones, such as sulpholane; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether; water.

The reaction temperature for the individual steps of the process (F) according to the invention can be varied within a relatively wide range. In general, the reactions are carried out at temperatures between −50° C. and 250° C., preferably between −20° C. and +100° C.

When carrying out the process (F), the chloroacetophenone (F-I) and the iminium salt (F-II) are employed in a molar ratio of from 1:1 to 2:1, preferably 1.1:1.

When carrying out the process (F), the compounds of the formula (F-III) and the benzyl cyanide of the formula (F-IV) are employed in a molar ratio of from 1:1 to 1:2, preferably 1:1.05.

When carrying out the process (F), the compounds of the formula (F-V) to NaOH and $H_2O_2$ are employed in a ratio of from 1:2.5:5 to 1:5:10, preferably 1:2.5:5, based on the equivalents.

When carrying out the process (F), PIFA (F-VII) and the compounds of the formula (F-VI) are employed in a molar ratio of from 1:1 to 3:1, preferably from 1:1 to 2:1.

The steps of the process (G) according to the invention are, if appropriate, carried out in the presence of a diluent. Suitable diluents are water (not for G. α and β), organic solvents and mixtures of these. Examples include: aliphatic, alicyclic or aromatic hydrocarbons, such as, for example, petroleum ether, hexane, heptane, cyclohexane, methylcyclohexane, benzene, toluene, xylene or decal in; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; ketones, such as acetone, butanone, methyl isobutyl ketone or cyclohexanone, nitriles, such as acetonitrile, propionitrile, n- or i-butyronitrile or benzonitrile; amides, such as formamide, N,N-dimethylformamide, N,N-dimethylacetamide, N-methylformanilide, N-methylpyrrolidone or hexamethylphosphoric triamide; N-oxides, such as N-methylmorpholine N-oxide; esters, such as methyl acetate, ethyl acetate or butyl acetate; sulphoxides, such as dimethyl sulphoxide; sulphones, such as sulpholane; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether; water.

The reaction temperature for the individual steps of the process (F) according to the invention can be varied within a relatively wide range. In general, the reactions are carried out at temperatures between −50° C. and 250° C., preferably between −20° C. and +100° C.

The steps α) and β) of the process (F) according to the invention are preferably carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium acetate, potassium acetate, calcium acetate or ammonium acetate, sodium carbonate, potassium carbonate or ammonium carbonate, sodium bicarbonate or potassium bicarbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine. diazabicyclooctane (DABCO), diazabicyclononene (DBN) or diazabicycloundecene (DBU). o-Chlorobenzoyl chloride or methyl ester are employed in excess.

The reactions of the processes according to the invention can be carried out at atmospheric pressure or at elevated pressure; preference is given to working at atmospheric pressure. Work-up is carried out by customary methods of organic chemistry. The end products are preferably purified by crystallization, chromatographic purification or by removing the volatile components, if appropriate under reduced pressure.

The active compounds are suitable for controlling animal pests, in particular insects, arachnids and nematodes, encountered in agriculture, in forestry, in the protection of stored products and of materials, and in the hygiene field, and have good plant tolerance and low toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp.

The phytoparasitic nematodes include Pratylenchus spp., *Radopholus similis, Ditylenchus dipsaci, Tylenchulus semipenetrans*, Heterodera spp., Meloidogyne spp., Aplelenchoides spp., Longidorus spp., Xiphinema spp., Trichodorus spp.

The active compounds of the formula (I) according to the invention in particular have outstanding activity against mustard beetle larvae (*Phaedon cochleariae*), caterpillars of the owlet moth (*Spodoptera frugiperda*), larvae of the green rice leaf hopper (*Nephotettix cincticeps*), green peach aphids (*Myzus persicae*) and all stages of the common spider mite (*Tetranychus urticae*).

The active compounds can be converted to the customary formulations, such as solutions, emulsions, wettable powders, suspensions, powders, dusting agents, pastes, soluble powders, granules, suspension emulsion concentrates, natural and synthetic materials impregnated with active compound and very fine capsules in polymeric substances.

These formulations are produced in a known manner, for example preferably by mixing the active compounds with extenders, that is liquid solvents and/or solid carriers, if appropriate with the use of surface-active agents, that is emulsifying agents and/or dispersing agents and/or foam-forming agents.

If the extender used is water, it is also possible to employ, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysis products; suitable dispersing agents are: for example ligninsulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous mixing components are the following:

Fungicides:
  2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclofos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:
  bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:
  abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cyprothrin, cyfluthrin, cyhalothrin, cyhexatin, cypernethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimfos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonofos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemeton M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozine, pyrachlofos, pyridaphenthion, pyresmethrin, pyrethrum, pyridaben, pyrimidifen, pyriproxyfen, quinalphos,

RH 5992, salithion, sebufos, silafluofen, sulfotep, sulprofos, tebufenozide, tebufenpyrad, tebupirimifos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth-regulators is also possible.

The active compound according to the invention can furthermore be present in its commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms. When used against hygiene pests and pests of stored products, the active compound has an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopyslla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Derrnacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

For example, they have an outstanding activity against all larval stages of the fly *Lucilia cuprina* and all development stages of the tick *Amblyomma variegatum*.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, caged birds, aquarium fish, and so-called experimental animals, such as, for example, hamsters, guinea-pigs, rats and mice. By controlling these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal administration, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of preferred examples but without any limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec., Tryptodendron spec., *Apate monachus, Bostrychus capucins, Heterobostrychus brunneus,* Sinoxylon spec. and *Dinoderus minutus.*

Dermapterans, such as

*Sirex juvencus, Urocerus gigas, Urocerus gigas taignus* and *Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as *Lepisma saccharina.*

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-like solvents having an evaporation number of above 35 and a flashpoint of above 30° C., preferably above 45° C. Substances which are used as such oily and oil-like solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-like solvents of low volatility and having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The artificial resin used as the binder can be employed in the form of an emulsion, dispersion or solution. Up to 10% by weight of bitumen or bituminous substances can also be used as binder. In addition, colorants, pigments, water repellents, odour-masking substances and inhibitors or anti-corrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly incorporated into the present application.

Very particularly preferred components which may be admixed are insecticides, such as chlorpyrifos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The preparation and the use of the active compounds according to the invention can be seen from the examples which follow.

PREPARATION EXAMPLES

Example I-8

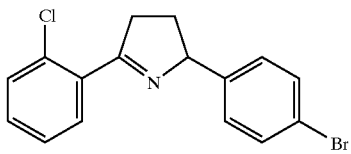

3.22 g (7.5 mmol) of PIFA (1,1-bis-(trifluoroacetoxy) iodobenzene) were initially charged in 25 ml of absolute acetonitrile and 10 ml of deionized water. At room temperature, 1.9 g (5.0 mmol) of F-VI-1 were then added, and the mixture was stirred at room temperature for approximately 4 h. The mixture was then admixed with 100 ml of 1N HCl and heated with stirring to 50° C. for approximately 3 h. The reaction mixture was extracted with methyl t-butyl ether, and the organic phases were combined. The organic phases were extracted with 1N HCl and the combined HCl phases were made alkaline using 20% strength NaOH solution. The resulting solution was again extracted with methyl t-butyl ether, and the organic phases were combined, dried and concentrated.

This gave 0.9 g (54% of theory) of 2-(2-chlorophenyl)-5-(4-bromophenyl)-3,4-dihydro-2H-pyrrole.

$^1$H-NMR (500 MHz, d$_6$-DMSO) [ppm]: 1.7/2.5/3.0–3.1 (m, 4H, 2×CH$_2$); 5.2 (m, 1H,CH); 7.2–7.7 (m, 8H, ArH).

Example I-7

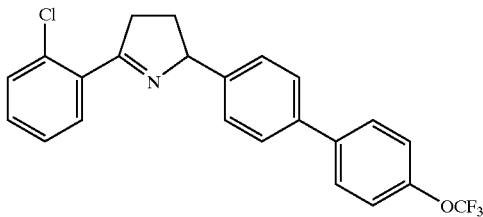

1.0 g (3.0 mmol) of 2-(2-chlorophenyl)-5-(4-bromophenyl)-3,4-dihydro-2H-pyrrole (I-8) was initially charged in 8.0 ml of dimethoxyethane and 6.4 ml of 1 N Na$_2$CO$_3$ solution. 0.93 g (4.5 mmol) of trifluoromethoxyphenylboronic acid was added at room temperature, and argon was subsequently passed through the reaction mixture for approximately 20 min. 105 mg (0.15 mmol; 5 mol %) of Pd (PPh$_3$)$_2$Cl$_2$ were then added, and the mixture was refluxed overnight. After examination by TLC, the reaction mixture, which had been cooled to room temperature, was admixed with approximately 30 ml of H$_2$O and 50 ml of ethyl acetate and filtered. The phases were separated, the aqueous phase was extracted repeatedly with ethyl acetate and the organic phases were combined, dried and concentrated. The crude product was chromatographed over silica gel using cyclohexane/ethyl acetate 10:1. This gave 0.14 g (11.2% of theory) of 2-(2-chlorophenyl)-5-(4-trifluoromethoxy-4,4'-biphenyl-1-yl)-3,4-dihydro-2H-pyrrole.

1H-NMR (500 MHz, CDCl$_3$) [ppm]: 2.0/2.7/3.2/3.3 (m, 4H, 2×CH$_2$); 5.4 (m, 1H,CH); 7.3–7.5 (m, 12H, Ar-H).

Example I-20

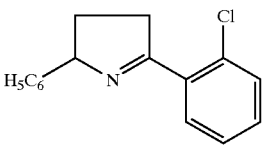

3.7 g (8.4 mmol) of 1,3-(2-chlorobenzoyl)-5-phenyl-pyrrolidin-2-one in 20 ml of HBr/glacial acetic acid (33% strength) were boiled at reflux for 4 hours. The reaction mixture was subsequently poured into water and extracted 3 times with ethyl acetate. The organic phases were combined, washed with sodium bicarbonate solution, dried and concentrated. The dark oil was purified by column chromatography using the system cyclohexane/ethyl acetate (2:1). This gave 0.45 g (yield: 21% of theory) of viscous oily 3,4-dihydro-2-(2-chlorophenyl)-5-phenyl-2H-pyrroline of log P* (pH 7.5)=3.6 l.

log P*=negative logarithm to base 10 of the alkane/water partition coefficient, determined by HPLC analysis on 125×4.0 mm Kromasil 120 C 18 (5 μm), using water/acetonitrile as mobile phase; flow rate: 1.5 ml/min.

Example I-43

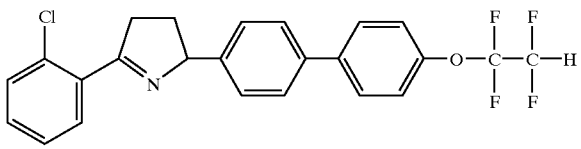

100 mg of the compound (VIII-43) were initially charged in 2 ml of CH$_2$Cl$_2$ and cooled to 0C. Trifluoroacetic acid (0.139 ml, 200 mg) was added, and the reaction mixture was subsequently stirred at room temperature overnight. The trifluoroacetic acid was evaporated off under reduced pressure using a rotary evaporator, and the residue was taken up in ethyl acetate. The pH was adjusted to 11 using 1 N NaOH. The organic phase was washed with water, dried over MgSO$_4$, filtered and concentrated. This gave 30 mg of the compound I-43.

HPLC: log P (pH 2.3)=4.01;
LC-MS: M$^+$+H 448.

PREPARATION OF THE STARTING MATERIALS

γ-Ethoxy-γ-butyrolactam

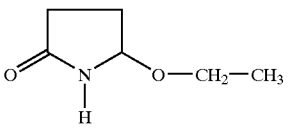

At 0° C., 9.91 g of succinimide were initially charged in 415 ml of ethanol and admixed, a little at a time, with a total of 5.53 g of sodium borohydride. At this temperature, every 15 minutes 2 to 3 drops of 2N ethanolic hydrogen chloride were added dropwise over a period of 4½ hours. The mixture was subsequently acidified to pH 3 using more acid. The mixture was stirred at 0C for one hour and then neutralized with 1% strength ethanolic potassium hydroxide solution, stirred for a further 15 minutes and concentrated. The residue was taken up in water and extracted three times with dichloromethane. Drying over sodium sulphate and concentration gave 7.16 g (55% of theory) of γ-ethoxy-γ-butyrolactam.

Example XI-1

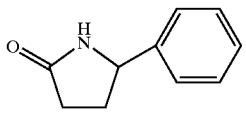

At 0° C., 6.45 g of γ-ethoxy-γ-butyrolactam and 50 ml of conc. sulphuric acid were initially charged, and 18.8 ml of benzene were added. After thawing, the mixture was stirred at room temperature for 4 days. For work-up, the mixture was poured onto ice and extracted three times with ethyl acetate, the combined extracts were washed once each with water and saturated sodium chloride solution, dried and concentrated. This gave 8.1 g (100% of theory) of γ-phenyl-γ-butyrolactam.

1H-NMR (400 MHz, d$_6$-DMSO) [ppm]: 1.75 (m, 1H); 2.23 (t, 2H); 2.45 (m, 1H); 4.67 (t, 1H); 7.26–7.39 (m, 5H); 8.08 (brd, 1H).

Example XI-2

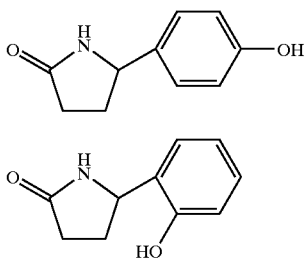

(XI-2a)

(XI-2b)

At 0° C., 12.9 g of γ-ethoxy-γ-butyrolactam, 10 ml of conc. sulphuric acid and 90 ml of glacial acetic acid were initially charged and admixed, a little at a time, with a total of 18.8 g of phenol. After thawing, the mixture was stirred at room temperature for 2 days. For work-up, the mixture was poured onto ice and extracted three times with ethyl acetate, and the combined extracts were washed once each with water and saturated sodium chloride solution, dried and concentrated. After some time, γ-2-hydroxyphenyl-γ-butyrolactam (XI-2b) of melting point 220° C. (6.4 g, 36% of theory) crystallized from the aqueous phase. The residue obtained after concentration was stirred with a 1:1 mixture of cyclohexane/ethyl acetate and gave, after filtration with suction, 4.65 g of γ-4-hydroxyphenyl-γ-butyrolactam (XI-2a) of melting point 183° C. The filtrate was concentrated. A further 3.35 g (total: 45% of theory) of γ-4-hydroxyphenyl-γ-butyrolactam were obtained by recrystallization from dichloromethane/hexane.

Example XVII-2

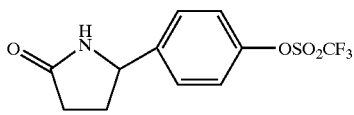

At 0° C., 10 g of trifluoromethanesulphonic anhydride were added dropwise to 5.23 g of γ-4-hydroxyphenyl-γ-butyrolactam (for example from Ex. XI-2) in 60 ml of pyridine. The mixture was stirred at room temperature overnight, then poured onto ice, acidified with 10% strength hydrochloric acid and extracted three times with ethyl acetate. Drying and evaporation of the solvent gave 6.4 g (70% of theory) of γ-4-trifluoromethylsulphonyloxyphenyl-γ-butyrolactam of melting point 127° C.

Example XI-a-2

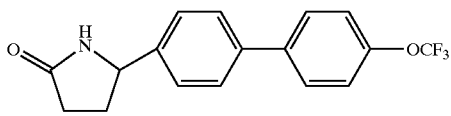

Under argon, 5.4 g of γ-4-trifluoromethylsulphonyloxyphenyl-γ-butyrolactam (for example from Ex. XVII-2) were initially charged in 43 ml of dimethoxyethane. 5.87 g of 4-trifluoromethoxyboronic acid and 1.01 g of tetrakis (triphenylphosphine)palladium were added successively. After 15 minutes, 28 ml of a 2M solution of sodium carbonate were added and the mixture was heated to 80° C. and stirred overnight. After the reaction had ended, the mixture was taken up in water/ethyl acetate, the phases were separated and the aqueous phase was extracted twice with ethyl acetate. The combined organic phases were washed with saturated sodium chloride solution and dried. Concentration gave 5.5 g (98% of theory) of γ-4'-trifluoromethoxybiphenyl-4-yl-γ-butyrolactam of melting point 128° C.

Example XI-3

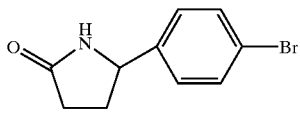

In a 3 l three-necked flask fitted with stirrer and distillation bridge, 199.3 g of ammonium formate were initially charged in 127.9 g of formic acid, and 210 g of 4-bromobenzoylpropionic acid which had been recrystallized from toluene were added. The flask was then immersed in an oil bath which was at 200° C. At 60° C., the content of the flask starts to dissolve with evolution of gas. Over a period of approximately 2 h, the mixture is distilled, at a bottom temperature which increases from 140 to 167° C. After cooling to below 60° C., 1 l of dichloromethane was added carefully, and salt which had precipitated out was separated off by filtration with suction using a nutsch filter. The organic phase was washed with 1 l of water, dried over magnesium sulphate and concentrated under reduced pressure. For purification, the crude product was filtered through 1 kg of silica gel using dichloromethane/ethanol/triethylamine (95:5:3) and subsequently crystallized from methyl tert-butyl ether. This gave 38 g (19% of theory) of γ-4-bromophenyl-γ-butyrolactam of melting point 142° C.

Example XI-43

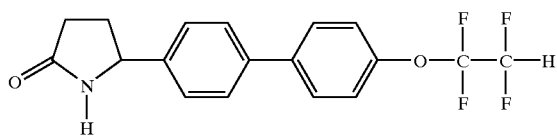

400 ml of HF were condensed into an autoclave. 38.7 g of γ-ethoxy-γ-butyrolactam and 40.6 g of tetrafluoroethoxybiphenyl were then jointly dissolved in 100 ml of CH$_2$Cl$_2$, and the mixture was added to the autoclave. The reaction mixture was stirred at room temperature overnight. The HF was drawn off and the residue was taken up in CH$_2$Cl$_2$ and washed with aqueous sodium bicarbonate solution. The organic phase was dried over MgSO$_4$, filtered and concentrated. The crude product was recrystallized from 500 ml of toluene. This gave 20.9 g of a white solid.

HPLC: log P (pH 2.3)=2.79

Example IX-1

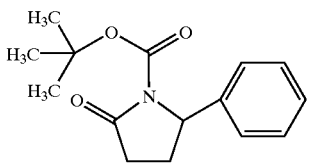

3.4 g of γ-phenyl-γ-butyrolactam (for example from Ex. XI-1) were initially charged in 63 ml of tetrahydrofuran (THF) and, at −78° C., admixed with 9.24 ml of a 2.4N solution of butyllithium in n-hexane. The mixture was stirred at this temperature for half an hour, and a solution of 5.04 g of di-tert-butyl dicarbonate in 20 ml of THF was added dropwise with further cooling and the mixture was stirred at −78° C. for a further three hours and then without cooling overnight. The mixture was then hydrolysed using saturated aqueous ammonium chloride solution, diluted with water and extracted three times with ethyl acetate. The combined organic phases were washed with saturated sodium chloride solution and dried over magnesium sulphate. Concentration gave 1.54 g (28% of theory) of N-t-butoxycarbonyl-γ-phenyl-γ-butyrolactam.

$^1$H-NMR (400 MHz, d$_6$-DMSO) [ppm]: 1.18 (s, 9H); 1.73 (m, 1H); 2.40–2.60 (m, 3H); 5.10 (m, 1H), 7.24 (m, 2H); 7.30 (m, 1H); 7.38 (m, 2H).

Example IX-2

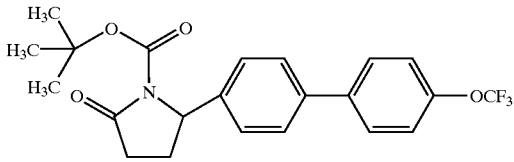

1.7 g of γ-4'-trifluoromethoxybiphenyl-4-yl-γ-butyrolactam (for example from Ex. XI-a-2) were initially charged in 30 ml of tetrahydrofuran (THF) and, at −78° C., admixed with 2.42 ml of a 2.4N solution of butyllithium in n-hexane. The mixture was stirred at this temperature for half an hour, and a solution of 1.27 g of di-tertbutyl dicarbonate in 10 ml of THF was then added dropwise with further cooling. The cooling was then removed and the mixture was stirred at room temperature overnight. The mixture was then hydrolysed using saturated aqueous ammonium chloride solution, acidified with 2N hydrochloric acid and extracted three times with dichloromethane. The extract was dried and concentrated and the product was purified by column chromatography (stationary phase: silica gel; mobile phase: gradient cyclohexane:ethyl acetate=5:1.3 to 1.1:1). This gave 1.14 g (47% of theory) of partially crystalline N-$^t$-butoxycarbonyl-γ-4'-trifluoromethoxybiphenyl-4-yl-γ-butyrolactam.

$^1$H-NMR (400 MHz, CDCl$_3$) [ppm]: 1.22 (s, 9H); 1.79 (m, 1H); 2.48–2.60 (m, 3H); 5.17 (m, 1H); 7.36 (d, 2H); 7.46 (d, 2H); 7.71 (d, 2H); 7.80 (d, 2H).

Example IX-3

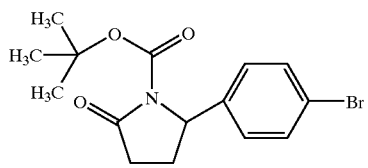

At −78° C., 3.24 ml of diisopropylamine were initially charged in 90 ml of THF and admixed with 9.24 ml of a 2.4 N solution of butyllithium in n-hexane. The mixture was stirred at this temperature for ½ h, and a solution of 5.02 g of γ-4-bromophenyl-γ-butyrolactam (for example from Example XI-3) in 20 ml of THF was then added dropwise. The mixture was stirred at −78° C. for a further ½ h, and 5.04 g of di-tert-butyl dicarbonate in 20 ml of THF were then added dropwise, and the mixture was allowed to thaw and stirred at room temperature overnight. The mixture was then hydrolysed using saturated aqueous ammonium chloride solution, acidified with 2N hydrochloric acid and extracted three times with 150 ml of dichloromethane. The extract was dried over magnesium sulphate and concentrated, and the product was then purified by crystallization from dichloromethane/hexane. This gave a total of 7.61 g (97% of theory) of crystalline N-$^t$butoxycarbonyl-γ-4-bromophenyl-γ-butyrolactam. The crystal fraction of the highest purity (2.34 g) melted at 122–124° C.

Example IX-43

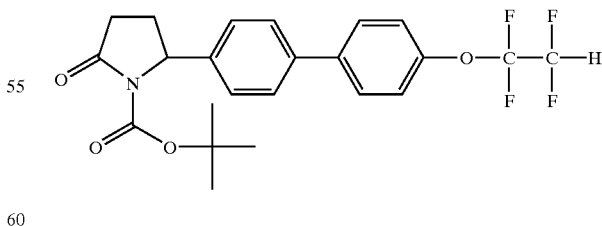

8.8 g of the compound (XI-43) were heated with 8.1 g of tert-butyl pyrocarbonate and 0.2 g of potassium fluoride in 80 ml of toluene at 108° C. for 6 hours, and the mixture was subsequently allowed to stand at room temperature overnight. 6.3 g of a solid precipitate* were filtered off with suction. The toluene solution was washed with water, and the organic phase was dried over MgSO₄, filtered and concentrated using a rotary evaporator. This gave 6.1 g of a white solid.

M.p. 134° C.; log P [pH 2.3]=3.96.

(* The solid precipitate also corresponds to the desired product.)

Example VIII-43

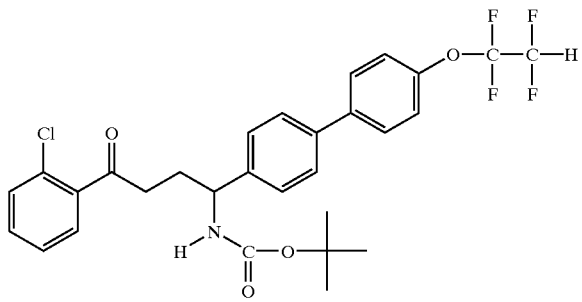

0.36 g of bromochlorobenzene were initially charged in 10 ml [hexane]. At −78° C., 1.19 ml of nBuLi (1.6 M in hexane) were added dropwise. After 15 minutes, 0.6 g of the compound (IX-43) in 2 ml of THF was added dropwise. The cooling bath was removed and the mixture was stirred at room temperature overnight. The reaction mixture was poured into 100 ml of water and extracted twice with ethyl acetate. The organic phase was dried over MgSO₄, filtered and concentrated using a rotary evaporator. The crude product was purified by column chromatography.

| Yield: | 0.12 g |
|---|---|
| HPLC: log P (pH 2.3): | 4.94 |
| M.p.: | 130–131° C. |

Example F-III

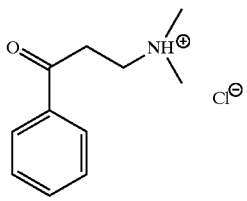

23.4 g (0.25 mol) of dimethylmethyleneammonium chloride were initially charged in 150 ml of absolute acetonitrile. At room temperature, 42.5 g (0.275 mol) of o-chloroacetophenone were subsequently added, and the mixture was finally stirred at room temperature. The dimethyleneammonium chloride gradually dissolved, and the product precipitated out. It was filtered off under exclusion of moisture and dried. This gave 54 g (87% of theory) of the ammonium chloride F-III.

¹H-NMR (400 MHz, CDCl₃) [ppm]: 2.9 (s, 6H, CH₃); 3.5/3.7 (t, 4H, 2×CH₂); 7.4/7.7 (m, 4H, ArH).

Example F-V-1

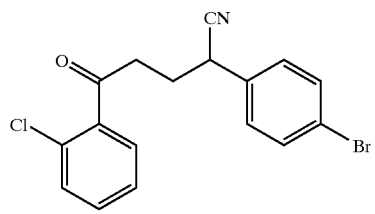

43.5 g (0.175 mol) of F-III were initially charged in 60 ml of ethanol p.a. and, at room temperature, 36.0 g (0.184 mol) of 4-bromobenzyl cyanide dissolved in 50.7 ml of ethanol p.a. were then added. 11.2 g (0.2 mol) of KOH in 40.0 ml of water were then added dropwise, and the solution warmed slightly. The mixture was stirred at room temperature for another 20 min and finally heated at reflux for 16 h. After the reaction mixture had cooled, it was poured into water, and the mixture was extracted with methyl tert-butyl ether. The organic phases were combined, washed with 2N HCl, 2N NaOH solution and H₂O, dried and concentrated. The crude product was purified by silica gel chromatography using methylene chloride/petroleum ether 2:1. This gave 12.8 g (20.2% of theory) of the compound.

¹H-NMR (400 MHz, DMSO-d₆) [ppm]: 2.25 (m, 2H, CHCH₂); 3.1 (t, 2H, COCH₂); 4.4 (t, 1H, CH); 7.9/7.7 (m, 8H, ArH).

Example F-VI-1

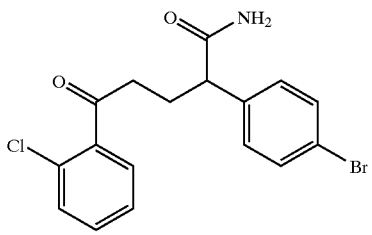

7.5 g (20.7 mmol) of F-V-1 were dissolved in 75 ml of ethanol p.a. and, at room temperature, added dropwise to a mixture of 17.7 ml of 3N NaOH solution and 11.8 ml of 30% H₂O₂ solution, and evolution of gas was observed. The mixture was stirred at room temperature until examination of the reaction by thin layer chromatography indicated the end of the reaction. The mixture was subsequently neutralized with hydrochloric acid, the solution was extracted with methylene chloride and any peroxide that was still present was destroyed using a solution of NaHSO₂. The organic phases were combined, dried and concentrated. The crude product was subsequently purified by silica gel chromatography using cyclohexane/ethyl acetate 4:1→1:1. This gave 3.1 g (39.3% of theory) of the compound F-VI-1 of melting point 105–107° C.

¹H-NMR (400 MHz, DMSO-d₆) [ppm]: 1.9/2.2 (m, 2H, CHCH₂); 2.7 (m, 2H, COCH₂); 3.5 (m, 1H, CH); 6.95 (brd s, 1H, NH); 7.3/7.6 (m, 9H, ArH+NH).

Example G(I)-20

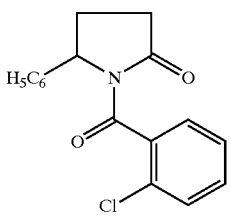

At room temperature, 28.6 g (0.163 mol) of 2-chlorobenzoyl chloride were added dropwise with stirring to a mixture of 25 g (0.155 mol) of 5-phenylpyrrolidin-2-one, 18.3 g (0.23 mol) of pyridine and 0.5 g of 4-dimethylaminopyridine, and the mixture was subsequently heated at reflux for 1.5 hours. After cooling, the mixture was poured into ice-water and the pH was adjusted to ~5 using dilute hydrochloric acid. The reaction mixture was subsequently extracted with dichloromethane. The organic phases were combined, washed with water, dried and concentrated under reduced pressure using a rotary evaporator. The oily residue was stirred with cyclohexane and the crystals were filtered off with suction. This gave 19.5 g (42% of theory) of 1-(2-chlorobenzoyl)-5-phenypyrrolidin-2-one of melting point 81–83° C.

Example G(II)-20

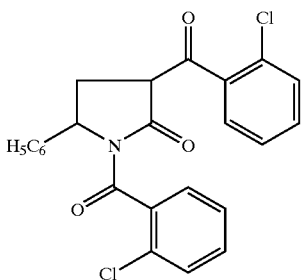

At room temperature, a solution of 11.4 g (67 mmol) of methyl 2-chlorobenzoate and 20 g (67 mmol) of 1-(2-chlorobenzoyl)-5-phenyl-pyrrolidin-2-one in 40 ml of abs. tetrahydrofuran was added dropwise with stirring to a mixture of 3 g (74 mmol) of sodium hydride (60%) in 150 ml of tetrahydrofliran. The mixture was subsequently heated at 50° C. for 3 hours and then cooled, acidified with acetic acid and diluted with water. The organic phase was separated off, dried and concentrated under reduced pressure. The viscous oil was purified by column chromatography using the system cyclohexane/ethyl acetate (2:1). This gave 9.9 g (yield: 33.7% of theory) of 1,3-(2-chlorobenzoyl)-5-phenyl-pyrrolidin-2-one as a glass-like and brittle product of log P (pH 2.5)=3.91.

BIOLOGICAL EXAMPLES

Example A

Heliothis Armigera Test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with emusifier-containing water to the desired concentration.

Soybean shoots (*Glycine max*) are treated by being dipped into the preparation of active compound of the desired concentration and are populated with caterpillars of the cotton bollworm (*Heliothis armigera*) while the leaves are still moist.

After the desired period of time, the kill in % is determined. 100% means that all caterpillars have been killed; 0% means that none of the caterpillars have been killed.

In this test, for example, the compound of Preparation Example I-7 shows, at an exemplary concentration of active compound of 0.004%, a kill of 100% after 6 days.

Example B

Phaedon Larvae Test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with emusifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the compound of Preparation Example I-7 shows, at an exemplary concentration of active compound of 0.004%, a kill of 100% after 6 days.

Example C

Plutella Test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with emusifier-containing water to the desired concentration.

Cabbage leaves (*Brassica oleracea*) are treated by being dipped into the preparation of active compound of the desired concentration and are populated with caterpillars of the diamond-back moth (*Plutella xylostella*) while the leaves are still moist.

After the desired period of time, the kill in % is determined. 100% means that all caterpillars have been killed; 0% means that none of the caterpillars have been killed.

In this test, for example, the compound of Preparation Example I-7 shows, at an exemplary concentration of active compound of 0.004%, a kill of 100% after 6 days.

Example D

*Spodoptera frugiperda* Test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with emusifier-containing water to the desired concentration.

Cabbage leaves (*Brassica oleracea*) are treated by being dipped into the preparation of active compound of the desired concentration and are populated with caterpillars of the army-worm (*Spodoptera frugiperda*) while the leaves are still moist.

After the desired period of time, the kill in % is determined. 100% means that all caterpillars have been killed; 0% means that none of the caterpillars have been killed.

In this test, for example, the compounds of Preparation Examples I-7 and I-8 show, at an exemplary concentration of active compound of at most 0.1%, a kill of 100% after 6 days.

Example E

Tetranychus Test (OP-resistant/dip Treatment)

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of the active compound of the desired concentration.

After the desired period of time, the kill in % is determined. 100% means that all spider mites have been killed; 0% means that none of the spider mites have been killed.

In this test, for example, the compounds of Preparation Examples I-7, I-8 and I-20 show, at an exemplary concentration of active compound of at most 0.1%, a kill of 100% after 6 days.

What is claimed is:

1. A compound of the formula (I)

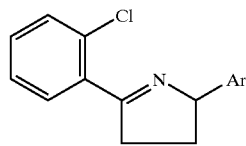

(I)

wherein

Ar represents the radical

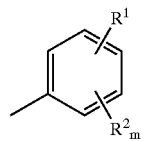

wherein m represents 0, 1, 2, 3 or 4, $R^1$ represents halogen, cyano, trialkylsilyl, —CO—$NR^4R^5$, tetrahydropyranyl or represents one of the following groupings
(l) —X—A
(m) —B—Z—D
(n) —Y—E, $R^2$ represents hydrogen, halogen, cyano, nitro, alkyl, alkoxy, halogenoalkyl, halogenoalkoxy, alkoxyalkoxy or —S(O)$_o$R$^3$, o represents 0, 1 or 2, $R^3$ represents alkyl or halogenoalkyl, $R^4$ and $R^5$ independently represent hydrogen, alkyl, halogenoalkyl or represent phenyl or phenylalkyl, each of which is optionally mono- or polysubstituted by radicals from the definition of $W^1$ given below, X represents a direct bond, oxygen, sulphur, carbonyl, carbonyloxy, oxycarbonyl, alkylene, alkenylene, alkynylene, alkyleneoxy, oxyalkylene, thioalkylene, alkylenedioxy or dialkylsilylene, A represents phenyl, naphthyl or tetrahydronaphthyl, each of which is optionally mono- or polysubstituted by radicals from the definition of $W^1$ given below, or represents 5- to 10-membered heterocyclyl containing one or two aromatic rings and having one or more heteroatoms selected from the group consisting of nitrogen, oxygen and sulphur and optionally mono- or polysubstituted by radicals from the definition of $W^2$ given below, B represents p-phenylene which is optionally mono- or disubstituted by radicals from the definition of $W^1$ given below, Z represents oxygen or sulphur, D represents hydrogen, alkyl, alkenyl, alkynyl, halogenoalkyl, halogenoalkenyl, optionally halogen-, alkyl-, alkenyl-, halogenoalkenyl-, phenyl-, styryl-, halogenophenyl- or halogenostyryl-substituted cycloalkyl or cycloalkylalkyl, represents optionally halogen- or alkyl-substituted cycloalkenyl or cycloalkenylalkyl, represents optionally nitro-, halogen-, alkyl-, alkoxy-, halogenoalkyl- or halogenoalkoxy-substituted phenylalkyl, naphthylalkyl, tetrahydronaphthylalkyl or hetarylalkyl having 5 or 6 ring members and one or two heteroatoms selected from the group consisting of nitrogen, oxygen and sulphur, represents —CO—R$^6$, —CO—NR$^7$R$^8$ or represents the grouping

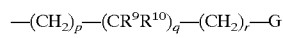

or

Z and D together represent optionally nitro-, halogen-, alkyl-, alkoxy-, halogenoalkyl- or halogenoalkoxy-substituted phenoxyalkyl, Y represents a direct bond, oxygen, sulphur, carbonyl, carbonyloxy, oxycarbonyl, alkylene, alkenylene, alkynylene, alkyleneoxy, oxyalkylene, thioalkylene, alkylenedioxy or represents p-phenylene which is optionally mono- or disubstituted by radicals from the definition of $W^1$ given below, E represents hydrogen, alkyl, alkenyl, alkynyl, halogenoalkyl, halogenoalkenyl, optionally halogen-, alkyl-, alkenyl-, halogenoalkenyl-, phenyl-, styryl-, halogenophenyl- or halogenostyryl-substituted cycloalkyl, represents optionally halogen- or alkyl-substituted cycloalkenyl, represents phenyl which is optionally mono- to tetrasubstituted by radicals from the definition of $W^1$ given below or represents 5- or 6-membered hetaryl having one or two heteroatoms selected from the group consisting of nitrogen, oxygen and sulphur and optionally mono- to tetrasubstituted by radicals from the definition of $W^2$ given below or represents the grouping

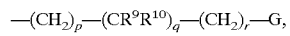

$R^6$ represents alkyl, alkoxy, alkenyl, alkenyloxy, optionally halogen-, alkyl-, alkenyl-, halogenoalkyl- or halogenoalkenyl-substituted cycloalkyl, cycloalkyloxy or cycloalkylalkyloxy or represents optionally nitro-, halogen-, alkyl-, alkoxy-, halogenoalkyl- or halogenoalkoxy-substituted phenyl or naphthyl, $R^7$ represents hydrogen or alkyl, $R^8$ represents alkyl, halogenoalkyl, optionally halogen-, alkyl-, alkenyl-, halogenoalkyl- or halogenoalkenyl-substituted cycloalkyl or cycloalkylalkyl or represents optionally halogen-, alkyl-, alkoxy-, halogenoalkyl- or halogenoalkoxy-substituted phenyl or phenylalkyl, p, q and r independently represent 0, 1, 2 or 3, with the sum of p, q and r being less than 6, $R^9$ and $R^{10}$ independently represent hydrogen or alkyl, G represents cyano, represents an optionally halogen-, alkyl- or halogenoalkyl- and, at the point of linkage, optionally $R^{11}$-substituted 5- or 6-membered heterocycle having 1 to 3 heteroatoms selected from the group consisting of nitrogen, oxygen and sulphur or one of the following groups

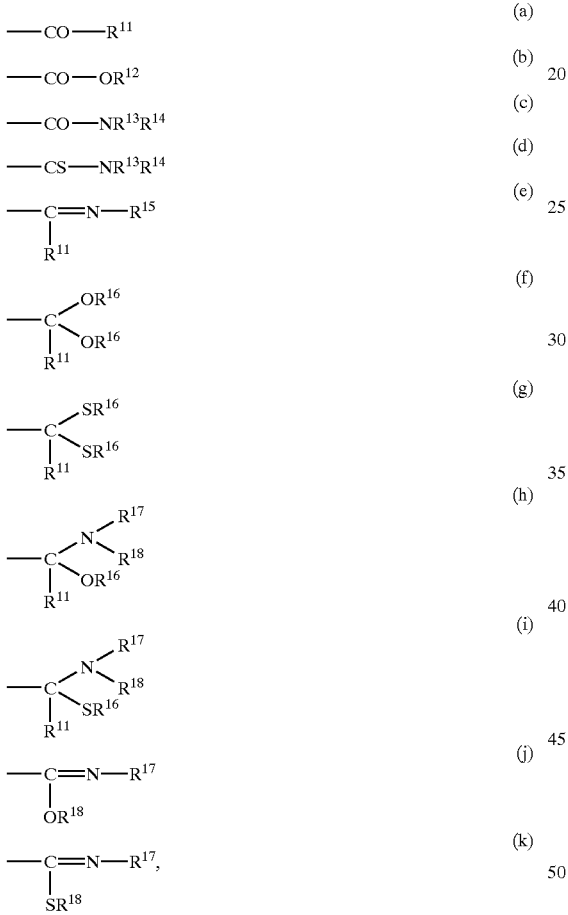

$R^{11}$ represents hydrogen, alkyl, alkenyl, halogenoalkyl, halogenoalkenyl, optionally halogen-, alkyl- or halogenoalkyl-substituted cycloalkyl or represents phenyl which is optionally mono- to pentasubstituted by alkylcarbonylamino, alkylcarbonylalkylamino and/or radicals from the definition of $W^3$ given below, $R^{12}$ represents hydrogen, alkyl, alkenyl, halogenoalkyl, halogenoalkenyl, optionally halogen-, alkyl- or halogenoalkyl-substituted cycloalkyl or cycloalkylalkyl or represents arylalkyl which is optionally mono- to pentasubstituted by radicals from the definition of $W^3$ given below, $R^{13}$ and $R^{14}$ independently represent hydrogen, alkyl, alkenyl, halogenoalkyl, halogenoalkenyl, alkoxy, optionally halogen-, alkyl- or halogenoalkyl-substituted cycloalkyl or cycloalkylalkyl, represents aryl or arylalkyl, each of which is optionally mono- to pentasubstituted by radicals from the definition of $W^3$ given below, represent —$OR^{12}$ or —$NR^{11}R^{12}$ or together represent an alkylene chain having 2 to 6 members in which optionally one methylene group is replaced by oxygen, $R^{15}$ represents —$OR^{12}$, —$NR^{11}R^{12}$ or —$N(R^{11})$—$COOR^{12}$, $R^{16}$, $R^{17}$ and $R^{18}$ independently represent alkyl, $W^1$ represents hydrogen, halogen, cyano, formyl, nitro, alkyl, trialkylsilyl, alkoxy, halogenoalkyl, halogenoalkoxy, halogenoalkenyloxy, alkylcarbonyl, alkoxycarbonyl, pentafluorothio or —$S(O)_oR^3$, $W^2$ represents halogen, cyano, formyl, nitro, alkyl, trialkylsilyl, alkoxy, halogenoalkyl, halogenoalkoxy, alkylcarbonyl, alkoxycarbonyl, pentafluorothio, —$S(O)_oR^3$ or —$C(R^{11})$=$N$—$R^{15}$, $W^3$ represents halogen, cyano, nitro, alkyl, alkoxy, halogenoalkyl, halogenoalkoxy, dialkylamino, —$S(O)_o R^3$, —$COOR^{19}$ or —$CONR^{20}R^{21}$, $R^{19}$ represents hydrogen, alkyl, halogenoalkyl, optionally halogen-, alkyl- or halogenoalkyl-substituted cycloalkyl or represents phenyl which is optionally mono- to pentasubstituted by radicals from the definition of $W^4$ given below, $R^{20}$ and $R^{21}$ independently represent hydrogen, alkyl, alkenyl, halogenoalkyl, halogenoalkenyl, alkoxy, optionally halogen-, alkyl- or halogenoalkyl-substituted cycloalkyl or cycloalkylalkyl or represent aryl or arylalkyl, each of which is optionally mono- to pentasubstituted by radicals from the definition of $W^4$ given below, represent —$OR^{16}$ or —$NR^{17}R^{18}$ or together represent an alkylene chain having 2 to 6 members in which optionally one methylene group is replaced by oxygen, and $W^4$ represents halogen, cyano, nitro, alkyl, alkoxy, halogenoalkyl, halogenoalkoxy, dialkylamino, alkoxycarbonyl, dialkylaminocarbonyl or —$S(O)_oR^3$.

2. The compound of claim 1, wherein
Ar represents the radical

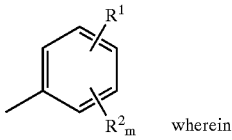 wherein m represents 0, 1, 2, 3, $R^1$ represents a substituent in the meta or para position from the group consisting of hydrogen, halogen, cyano, tri-($C_1$–$C_6$-alkyl)-silyl, —CO—$NR^4R^5$, tetrahydropyranyl or one of the following groupings —X—A (l)

—B—Z—D (m)

—Y—E, (n)

$R^2$ represents hydrogen, halogen, cyano, nitro, $C_1$–$C_{16}$-alkyl, $C_1$–$C_{16}$-alkoxy, $C_1$–$C_6$-halogenoalkyl, $C_1$–$C_6$-halogenoalkoxy, $C_1$–$C_8$-alkoxy-$C_1$–$C_8$-alkoxy or —$S(O)_oR^3$, o represents 0, 1 or 2, $R^3$ represents optionally fluorine- or chlorine-substituted $C_1$–$C_6$-alkyl, $R^4$ and $R^5$ independently represent hydrogen, $C_1$–$C_6$-alkyl, $C_1$–$C_6$-halogenoalkyl or represent phenyl or phenyl-$C_1$–$C_4$-alkyl, each of which is optionally mono- to trisubstituted by radicals from the definition of $W^1$ given below, X represents a direct bond, oxygen, sulphur, carbonyl, carbonyloxy, oxycarbonyl, $CC_1$–$C_4$-alkylene, $C_2$–$C_4$-alkenylene, $C_2$–$C_4$-alkynylene, $C_1$–$C_4$-alkyleneoxy, $C_1$–$C_4$-oxyalkylene, $C_1$–$C_4$-thioalkylene, $C_1$–$C_4$-alkylenedioxy or di-$C_1$–$C_4$-alkylsilylene, A represents phenyl, naphthyl or tetrahydronaphthyl, each of which is optionally mono- to tetrasubstituted by radicals from the definition of $W^1$ given below, or represents 5- to 10-membered heterocyclyl containing 1 or 2 aromatic rings and having 1 to 4 heteroatoms, which contains 0 to 4 nitrogen atoms, 0 to 2 oxygen atoms and 0 to 2 sulphur atoms (including furyl, benzofuryl, thienyl, benzothienyl, oxazolyl, benzoxazolyl, thiazolyl, benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl), and optionally mono- to tetrasubstituted by radicals from the definition of $W^2$ given below, B represents p-phenylene which is optionally mono- or disubstituted by radicals from the definition of $W^1$ given below, Z represents oxygen or sulphur, D represents hydrogen, $C_1$–$C_{16}$-alkyl, $C_2$–$C_{16}$-alkenyl, $C_2$–$C_6$-alkynyl, $C_1$–$C_{16}$-halogenoalkyl, $C_2$–$C_{16}$-halogenoalkenyl, optionally halogen-, $C_1$–$C_4$-alkyl-, $C_2$–$C_4$-alkenyl-, $C_2$–$C_4$-halogenoalkenyl-, phenyl-, styryl-, halogenophenyl- or halogenostyryl-substituted $C_3$–$C_8$-cycloalkyl or $C_3$–$C_8$-cycloalkyl-$C_1$–$C_6$-alkyl, represents optionally halogen- or $C_1$–$C_4$-alkyl-substituted $C_5$–$C_8$-cycloalkenyl or $C_5$–$C_8$-cycloalkenyl-$C_1$–$C_4$-alkyl, represents optionally nitro-, halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, naphthyl-$C_1$–$C_6$-alkyl, tetrahydronaphthyl-$C_1$–$C_6$-alkyl or hetaryl-$C_1$–$C_6$-alkyl having 5 or 6 ring members and 1 or 2 heteroatoms selected from the group consisting of nitrogen, oxygen and sulphur (including furyl methyl, thienylmethyl, pyrrolylmethyl, oxazolylmethyl, isoxazolylmethyl, thiazolylmethyl or pyridylmethyl), represents —CO—$R^6$, —CO—$NR^7R^8$ or represents the grouping —($CH_2$)$_p$—($CR^9R^{10}$)$_q$—($CH_2$)$_r$—G, Z and D together may also represent optionally nitro-, halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenoxy-$C_1$–$C_4$-alkyl, Y represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkynylene, $C_1$–$C_4$-alkyleneoxy, $C_1$–$C_4$-oxyalkylene, $C_1$–$C_4$-thioalkylene, $C_1$–$C_4$-alkylenedioxy or represents p-phenylene which is optionally mono- or disubstituted by radicals from the definition of $W^1$ given below, E represents hydrogen, $C_1$–$C_{16}$-alkyl, $C_2$–$C_{16}$-alkenyl, $C_2$–$C_6$-alkynyl, $C_1$–$C_{16}$-halogenoalkyl, $C_2$–$C_{16}$-halogenoalkenyl, optionally halogen-, $C_1$–$C_4$-alkyl-, $C_2$–$C_4$-alkenyl-, $C_2$–$C_4$-halogenoalkenyl, phenyl-, styryl-, halogenophenyl- or halogenostyryl-substituted $C_3$–$C_8$-cycloalkyl, represents optionally halogen- or $C_1$–$C_4$-alkyl-substituted $C_5$–$C_8$-cycloalkenyl, represents phenyl which is optionally mono- to tetrasubstituted by radicals from the definition of $W^1$ given below or represents 5- or 6-membered hetaryl having 1 or 2 heteroatoms selected from the group consisting of nitrogen, oxygen and sulphur (including furyl, thienyl, pyrrolyl, oxazolyl, isoxazolyl, thiazolyl or pyridyl) which is optionally mono- to tetrasubstituted by radicals from the definition of $W^2$ given below or represents the grouping —($CH_2$)$_p$—($CR^9R^{10}$)$_q$—($CH_2$)$_r$—G, $R^6$ represents $C_1$–$C_{12}$-alkyl, $C_1$–$C_{12}$-alkoxy, $C_2$–$C_{12}$-alkenyl, $C_2$–$C_{12}$-alkenyloxy, optionally halogen-, $C_1$–$C_4$-alkyl-, $C_2$–$C_4$-alkenyl-, $C_1$–$C_4$-halogenoalkyl- or $C_2$–$C_4$-halogenoalkenyl-substituted $C_3$–$C_8$-cycloalkyl, $C_3$–$C_8$-cycloalkyloxy or $C_3$–$C_8$-cycloalkyl-$C_1$–$C_6$-alkyloxy or represents phenyl or naphthyl each of which is optionally mono- to tetrasubstituted by nitro, halogen, $C_1$–$C_{12}$-alkyl, $C_1$–$C_{12}$-alkoxy, $C_1$–$C_{12}$-halogenoalkyl or $C_1$–$C_{12}$-halogenoalkoxy, $R^7$ represents hydrogen or $C_1$–$C_{12}$-alkyl, $R^8$ represents $C_1$–$C_{12}$-alkyl, $C_1$–$C_{12}$-halogenoalkyl, optionally halogen-, $C_1$–$C_4$-alkyl-, $C_2$–$C_4$-alkenyl-, $C_1$–$C_4$-halogenoalkyl- or $C_2$–$C_4$-halogenoalkenyl-substituted $C_3$–$C_8$-cycloalkyl or $C_3$–$C_8$-cycloalkyl-$C_1$–$C_6$-alkyl or represents phenyl or phenyl-$C_1$–$C_6$-alkyl, each of which is optionally mono- to tetrasubstituted by halogen, $C_1$–$C_{12}$-alkyl, $C_1$–$C_{12}$-alkoxy, $C_1$–$C_{12}$-halogenoalkyl or $C_1$–$C_{12}$-halogenoalkoxy, p, q and r independently represent 0, 1, 2 or 3, with the sum of p, q and r being less than 6, $R^9$ and $R^{10}$ independently represent hydrogen or $C_1$–$C_4$-alkyl, G represents cyano, represents a 5- or 6-membered heterocycle having 1 to 3 heteroatoms selected from the group consisting of nitrogen, oxygen and sulphur (including 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl) and optionally mono- to trisubstituted by halogen, $C_1$–$C_4$-alkyl or $C_1$–$C_4$-halogenoalkyl and optionally, at the point of linkage, by the radical $R^{11}$, or represents one of the following groupings:

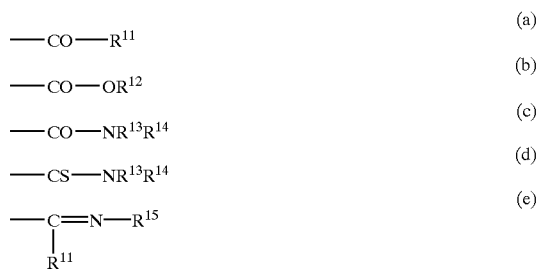

-continued

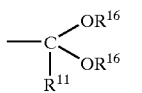 (f)

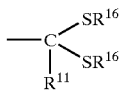 (g)

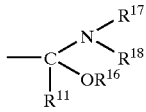 (h)

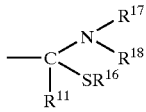 (i)

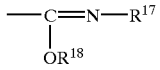 (j)

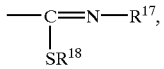 (k)

$R^{11}$ represents hydrogen, $C_1$–$C_6$-alkyl, $C_2$–$C_6$-alkenyl, $C_1$–$C_4$-halogenoalkyl, $C_2$–$C_6$-halogenoalkenyl, optionally halogen-, $C_1$–$C_4$-alkyl- or $C_1$–$C_4$-halogenoalkyl-substituted $C_3$–$C_6$-cycloalkyl or represents phenyl which is optionally mono- to pentasubstituted by $C_1$–$C_4$-alkylcarbonylamino, $C_1$–$C_4$-alkylcarbonyl-$C_1$–$C_4$-alkylamino and/or radicals from the definition of $W^3$ given below, $R^{12}$ represents hydrogen, $C_1$–$C_4$-alkyl, $C_2$–$C_6$-alkenyl, $C_1$–$C_4$-halogenoalkyl, $C_2$–$C_6$-halogenoalkenyl, optionally halogen-, $C_1$–$C_4$-alkyl- or $C_1$–$C_4$-halogenoalkyl-substituted $C_3$–$C_6$-cycloalkyl or $C_3$–$C_6$-cycloalkyl-$C_1$–$C_4$-alkyl or represents $C_6$–$C_{10}$-aryl-$C_1$–$C_4$-alkyl which is optionally mono- to tetrasubstituted by radicals from the definition of $W^3$ given below, $R^{13}$ and $R^{14}$ independently represent hydrogen, $C_1$–$C_4$-alkyl, $C_3$–$C_6$-alkenyl, $C_1$–$C_4$-halogenoalkyl, $C_3$–$C_6$-halogenoalkenyl, $C_1$–$C_4$-alkoxy, optionally halogen-, $C_1$–$C_4$-alkyl- or $C_1$–$C_4$-halogenoalkyl-substituted $C_3$–$C_6$-cycloalkyl or $C_3$–$C_6$-cycloalkyl-$C_1$–$C_4$-alkyl, represent phenyl or phenyl-$C_1$–$C_4$-alkyl, each of which is optionally mono- to pentasubstituted by radicals from the definition of $W^3$ given below, represent —$OR^{12}$ or —$NR^{11}R^{12}$ or together represent an alkylene chain having 4 to 6 members in which optionally one methylene group is replaced by oxygen, $R^{15}$ represents —$OR^{12}$, —$NR^{11}R^{12}$ or —$N(R^{11})$—$COOR^{12}$, $R^{16}$, $R^{17}$ and $R^{18}$ independently represent $C_1$–$C_6$-alkyl, $W^1$ represents hydrogen, halogen, cyano, formyl, nitro, $C_1$–$C_6$-alkyl, tri-$C_1$–$C_4$-alkylsilyl, $C_1$–$C_{16}$-alkoxy, $C_1$–$C_6$-halogenoalkyl, $C_1$–$C_6$-halogenoalkoxy, $C_2$–$C_6$-halogenoalkenyloxy, $C_1$–$C_6$-alkylcarbonyl, $C_1$–$C_{16}$-alkoxycarbonyl, pentafluorothio or —$S(O)_oR^3$, $W^2$ represents halogen, cyano, formyl, nitro, $C_1$–$C_6$-alkyl, tri-$C_1$–$C_4$-alkylsilyl, $C_1$–$C_{16}$-alkoxy, $C_1$–$C_6$-halogenoalkyl, $C_1$–$C_6$-halogenoalkoxy, $C_1$–$C_6$-alkylcarbonyl, $C_1$–$C_{16}$-alkoxycarbonyl, pentafluorothio, —$S(O)_oR^3$ or —$C(R^{11})$=N—$R^{15}$, $W^3$ represents halogen, cyano, nitro, $C_1$–$C_4$-alkyl, $C_1$–$C_4$-alkoxy, $C_1$–$C_4$-halogenoalkyl, $C_1$–$C_4$-halogenoalkoxy, di-$C_1$–$C_4$-alkylamino, —$S(O)_oR^3$, —$COOR^{19}$ or —$CONR^{20}R^{21}$, $R^{19}$ represents hydrogen, $C_1$–$C_4$-alkyl, $C_1$–$C_4$-halogenoalkyl, optionally halogen-, $C_1$–$C_4$-alkyl- or $C_1$–$C_4$-halogenoalkyl-substituted $C_3$–$C_7$-cycloalkyl or represents phenyl which is optionally mono- to pentasubstituted by radicals from the definition of $W^4$ given below, $R^{20}$ and $R^{21}$ independently represent hydrogen, $C_1$–$C_4$-alkyl, $C_3$–$C_6$-alkenyl, $C_1$–$C_4$-halogenoalkyl, $C_3$–$C_6$-halogenoalkenyl, $C_1$–$C_4$-alkoxy, optionally halogen-, $C_1$–$C_4$-alkyl- or $C_1$–$C_4$-halogenoalkyl-substituted $C_3$–$C_6$-cycloalkyl or $C_3$–$C_6$-cycloalkyl-$C_1$–$C_4$-alkyl or represent phenyl or phenyl-$C_1$–$C_4$-alkyl, each of which is optionally mono- to pentasubstituted by radicals from the definition of $W^4$ given below, represent —$OR^{16}$ or —$NR^{17}R^{18}$ or together represent an alkylene chain having 4 to 6 members in which optionally one methylene group is replaced by oxygen, and $W^4$ represents halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, di-$C_1$–$C_4$-alkylamino, $C_1$–$C_6$-alkoxycarbonyl, di-$C_1$–$C_6$-alkylaminocarbonyl or —$S(O)_oR^3$.

3. The compound of claim 1, wherein
Ar represents the radical

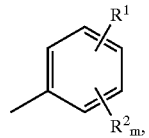

m represents 0, 1 or 2, $R^1$ represents a substituent in the meta or para position from the group consisting of hydrogen, fluorine, chlorine, bromine, iodine, cyano, tri-($C_1$–$C_4$-alkyl)-silyl, —CO—$NR^4R^5$, tetrahydropyranyl or one of the following groupings

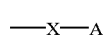 (l)

 (m)

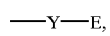 (n)

$R^2$ represents hydrogen, fluorine, chlorine, bromine, iodine, cyano, nitro, $C_1$–$C_{16}$-alkyl, $C_1$–$C_{16}$-alkoxy, fluorine- or chlorine-substituted $C_1$–$C_6$-alkyl or $C_1$–$C_6$-alkoxy, represents $C_1$–$C_8$-alkoxy-$C_1$–$C_8$-alkoxy or —$S(O)_oR^3$, o represents 0, 1 or 2, $R^3$ represents $C_1$–$C_4$-alkyl or fluorine- or chlorine-substituted methyl or ethyl, $R^4$ and $R^5$ independently represent hydrogen, $C_1$–$C_6$-alkyl, fluorine- or chlorine-substituted $C_1$–$C_6$-alkyl or represent phenyl or benzyl, each of which is optionally mono- or disubstituted by radicals from the definition of $W^1$ given below, X represents a direct bond, oxygen, sulphur, carbonyl, carbonyloxy, oxycarbonyl, $C_1$–$C_4$-alkylene $C_2$–$C_4$-alkenylene $C_2$–$C_4$-alkynylene $C_1$–$C_4$-alkylenoxy, $C_1$–$C_4$-oxyalkylene, $C_1$–$C_4$-thioalkylene, $C_1$–$C_4$-alkylenedioxy or di-$C_1$–$C_4$-alkylsilylene, A represents phenyl, naphthyl or tetrahydronaphthyl, each of which is optionally mono- to trisubstituted by radicals from the definition of $W^1$, given below, or represents 5- to 10-membered heterocyclyl containing one or two aromatic rings and having 1 to 4 heteroatoms which contains 0 to 4 nitrogen atoms, 0 to 2 oxygen atoms and 0 to 2 sulphur atoms (including furyl, benzofuryl, thienyl, benzothienyl, oxazolyl, benzoxazolyl, thiazolyl, benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl) and optionally mono- to trisubstituted by radicals from the definition of $W^2$ given below, B represents p-phenylene which is optionally mono- or disubstituted by radicals from the definition of $W^1$ given below, Z represents oxygen or sulphur, D represents hydrogen, $C_1$–$C_{16}$-alkyl, $C_2$–$C_{16}$-alkenyl, $C_2$–$C_6$-alkynyl, fluorine- or chlorine-substituted $C_1$–$C_4$-alkyl or $C_2$–$C_4$-alkenyl, represents $C_3$–$C_6$-cycloalkyl or $C_3$–$C_6$-cycloalkyl-$C_1$–$C_4$-alkyl, each of which is optionally substituted by fluorine, chlorine, bromine, $C_1$–$C_4$-alkyl, $C_2$–$C_4$-alkenyl, by fluorine- or chlorine-substituted $C_2$–$C_4$-alkenyl, by phenyl, styryl, fluorine-, chlorine- or bromine-substituted phenyl or styryl, represents optionally fluorine-, chlorine-, bromine- or $C_1$–$C_4$-alkyl-substituted $C_5$–$C_6$-cycloalkenyl or $C_5$–$C_6$-cycloalkenyl-$C_1$–$C_4$-alkyl, represents phenyl-$C_1$–$C_4$-alkyl, napthyl-$C_1$–$C_4$-alkyl, tetrahydronaphthyl-$C_1$–$C_6$-alkyl or hetaryl-$C_1$–$C_4$-alkyl having 5 or 6 ring members and one or two heteroatoms selected from the group consisting of nitrogen, oxygen and sulphur (including furylmethyl, thienylmethyl, pyrrolylmethyl, oxazolylmethyl, isoxazolylmethyl, thioazolylmethyl or pyridylmethyl), each of which is optionally substituted by nitro, fluorine, chlorine, bromine, $C_1$–$C_6$-alkyl, $C_1$–$C_6$-alkoxy, fluorine- or chlorine-substituted $C_1$–$C_4$-alkyl or $C_1$–$C_4$-alkoxy, represents —CO—$R^6$, —CO—$NR^7R^8$ or the grouping

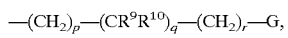

Z and D together may also represent substituted phenoxy-$C_1$–$C_3$-alkyl which is optionally substituted by nitro, fluorine, chlorine, bromine, $C_1$–$C_4$-alkyl, $C_1$–$C_4$-alkoxy, fluorine-, or chlorine-substituted $C_1$–$C_4$-alkyl or $C_1$–$C_4$-alkoxy, Y represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkynylene, $C_1$–$C_4$-alkyleneoxy, $C_1$–$C_4$-oxyalkylene, $C_1$–$C_4$-thioalkylene, $C_1$–$C_4$-alkylenedioxy or represents p-phenylene which is optionally mono- or disubstituted by radicals from the definition of $W^1$ given below, E represents hydrogen, $C_1$–$C_{16}$-alkyl, $C_2$–$C_{16}$-alkenyl, $C_2$–$C_6$-alkynyl, fluorine- or chlorine-substituted $C_1$–$C_4$-alkyl or $C_2$–$C_4$-alkenyl, represents $C_3$–$C_6$-cycloalkyl which is optionally substituted by fluorine, chlorine, bromine, $C_1$–$C_4$-alkyl, $C_2$–$C_4$-alkenyl, by fluorine- or chlorine-substituted $C_2$–$C_4$-alkenyl, by phenyl, styryl or fluorine-, chlorine- or bromine-substituted phenyl or styryl, represents optionally fluorine-, chlorine-, bromine- or $C_1$–$C_4$-alkyl-substituted $C_5$–$C_6$-cycloalkenyl, represents phenyl which is optionally mono- to trisubstituted by radicals from the definition of $W^1$ given below or represents 5- or 6-membered hetaryl having 1 or 2 heteroatoms selected from the group consisting of nitrogen, oxygen and sulphur (including furyl, thienyl, pyrrolyl, oxazolyl, isoxazolyl, thiazolyl or pyridyl), each of which is optionally mono- or disubstituted by radicals from the definition of $W^2$ given below, or represents the grouping

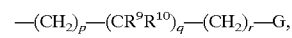

$R^6$ represents $C_1$–$C_6$-alkyl, $C_1$–$C_6$-alkoxy, $C_2$–$C_6$-alkenyl, $C_2$–$C_6$-alkenyloxy, represents $C_3$–$C_6$-cycloalkyl, $C_3$–$C_6$-cycloalkyloxy or $C_3$–$C_6$-cycloalkyl-$C_1$–$C_2$-alkyloxy, each of which is optionally substituted by fluorine, chlorine, $C_1$–$C_3$-alkyl or fluorine- or chlorine-substituted $C_1$–$C_2$-alkyl or $C_2$–$C_3$-alkenyl, or represents phenyl which is optionally mono- or disubstituted by fluorine, chlorine, bromine, iodine, $C_1$–$C_4$-alkyl, $C_1$–$C_4$-alkoxy or by fluorine- or chlorine-substituted $C_1$–$C_3$-alkyl or $C_1$–$C_4$-alkoxy, $R^7$ represents hydrogen or $C_1$–$C_4$-alkyl, $R^8$ represents $C_1$–$C_4$-alkyl or represents phenyl or benzyl, each of which is optionally mono- or disubstituted by fluorine, chlorine, bromine, $C_1$–$C_4$-alkyl or by fluorine-, or chlorine-substituted $C_1$–$C_4$-alkyl or $C_1$–$C_4$-alkoxy, p, q and r independently represent 0, 1, 2 or 3, with the sum of p, q and r being less than 6, $R^9$ and $R^{10}$ independently represent hydrogen or $C_1$–$C_4$-alkyl, G represents cyano, represents a 5- or 6-membered heterocycle having 1 to 3 heteroatoms selected from the group consisting of nitrogen, oxygen and sulphur (including 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl) and optionally mono- to trisubstituted by fluorine, chlorine, bromine, $C_1$–$C_4$-alkyl or by fluorine- or chlorine-substituted $C_1$–$C_4$-alkyl and optionally, at the point of linkage, by the radical $R^{11}$, or represents one of the following groupings:

 (a)

 (b)

 (c)

 (d)

 (e)

 (f)

 (g)

-continued

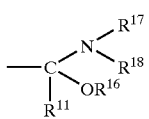
(h)

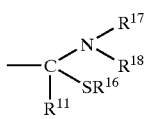
(i)

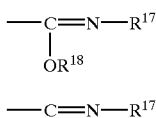
(j)

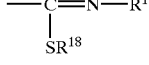
(k)

$R^{11}$ represents hydrogen, $C_1$–$C_6$-alkyl, $C_2$–$C_6$-alkenyl, fluorine- or chlorine-substituted $C_1$–$C_4$-alkyl or $C_1$–$C_6$-alkenyl, represents $C_3$–$C_6$-cycloalkyl which is optionally substituted by fluorine, chlorine, $C_1$–$C_4$-alkyl or by fluorine- or chlorine-substituted $C_1$–$C_4$-alkyl, or represents phenyl which is optionally mono- to trisubstituted by $C_1$–$C_4$-alkylcarbonylamino, $C_1$–$C_4$-alkylcarbonyl-$C_1$–$C4$-alkylamino and/or radicals from the definition of $W^3$ given below, $R^{12}$ represents hydrogen, $C_1$–$C_4$-alkyl, $C_3$–$C_6$-alkenyl, fluorine- or chlorine-substituted $C_1$–$C_4$-alkyl or $C_3$–$C_6$-alkenyl, represents $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl or by fluorine- or chlorine-substituted $C_1$–$C_4$-alkyl, or represents phenyl-$C_1$–$C_4$-alkyl or naphthyl-$C_1$–$C_4$-alkyl, each of which is optionally mono- to trisubstituted by radicals from the definition of $W^3$ given below, $R^{13}$ and $R^{14}$ independently represent hydrogen, $C_1$–$C_4$-alkyl, $C_3$–$C_6$-alkenyl, fluorine- or chlorine-substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl or by fluorine- or chlorine-substituted $C_1$–$C_4$-alkyl, represent phenyl or phenyl-$C_1$–$C_4$-alkyl, each of which is optionally mono- to trisubstituted by radicals from the definition of $W^3$ given below, represent —$OR^{12}$ or —$NR^{11}R^{12}$ or together represent —$(CH_2)_5$—, —$(CH_2)_6$— or —$(CH_2)_2$—O—$(CH_2)_2$—, $R^{15}$ represents —$OR^{12}$, —$NR^{11}R^{12}$ or —$N(R^{11})$—$COOR^{12}$, $R^{16}$, $R^{17}$ and $R^{18}$ independently represent $C_1$–$C_4$-alkyl, $W^1$ represents hydrogen, fluorine, chlorine, bromine, iodine, cyano, formyl, nitro, $C_1$–$C_4$-alkyl, $C_1$–$C_4$-alkoxy, fluorine- or chlorine-substituted $C_1$–$C_4$-alkyl or $C_1$–$C_4$-alkoxy, represents $C_1$–$C_4$-alkylcarbonyl, $C_1$–$C_4$-alkoxycarbonyl or —$S(O)_oR^3$, $W^2$ represents fluorine, chlorine, bromine, cyano, formyl, nitro, $C_1$–$C_4$-alkyl, $C_1$–$C_4$-alkoxy, fluorine- or chlorine-substituted $C_1$–$C_4$-alkyl or $C_1$–$C_4$-alkoxy, represents $C_1$–$C_4$-alkylcarbonyl, $C_1$–$C_4$-alkoxycarbonyl, —$S(O)_oR^3$ or —$C(R^{11})$=N—$R^{15}$, $W^3$ represents fluorine, chlorine, bromine, cyano, nitro, $C_1$–$C_4$-alkyl, $C_1$–$C_4$-alkoxy, fluorine- or chlorine-substituted $C_1$–$C_4$-alkyl or $C_1$–$C_4$-alkoxy, represents di-$C_1$–$C_4$-alkylamino, —$S(O)_oR^3$, —$COOR^{19}$ or —$CONR^{20}R^{21}$, $R^{19}$ represents hydrogen, $C_1$–$C_4$-alkyl, fluorine- or chlorine-substituted $C_1$–$C_4$-alkyl, represents $C_3$–$C_6$-cycloalkyl which is optionally substituted by fluorine, chlorine, $C_1$–$C_4$-alkyl or by fluorine- or chlorine-substituted $C_1$–$C_4$-alkyl, or represents phenyl, which is optionally mono- to trisubstituted by radicals from the definition of $W^4$ given below, $R^{20}$ and $R^{21}$ independently represent hydrogen, $C_1$–$C_4$-alkyl, $C_3$–$C_6$-alkenyl, fluorine- or chlorine-substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl or by fluorine- or chlorine-substituted-$C_1$–$C_4$-alkyl, or represent phenyl or phenyl-$C_1$–$C_4$-alkyl, each of which is optionally mono- to trisubstituted by radicals from the definition of $W^4$ given below, represent —$OR^{16}$ or —$NR^{17}R^{18}$ or together represent —$(CH_2)_5$—, —$(CH_2)_6$— or —$(CH_2)_2$—O—$(CH_2)_2$—, and $W^4$ represents fluorine, chlorine, bromine, cyano, nitro, $C_1$–$C_4$-alkyl, $C_1$–$C_4$-alkoxy, fluorine- or chlorine-substituted $C_1$–$C_4$-alkyl or $C_1$–$C_4$-alkoxy, di-$C_1$–$C_4$-alkylamino, $C_1$–$C_4$-alkoxycarbonyl, di-$C_1$–$C_6$-alkylaminocarbonyl or —$S(O)_oR^3$.

4. The compound of claim 1, wherein

Ar represents the radical

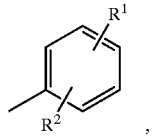

$R^1$ represents a substituent in the meta or para position from the group consisting of hydrogen, fluorine, chlorine, bromine, iodine, cyano, —CO—$NR^4R^5$, tetrahydropyranyl or one of the groupings below —X—A (l)

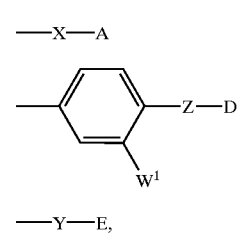
(m-a)

—Y—E, (n)

$R^2$ represents hydrogen, fluorine, chlorine, bromine, methyl, ethyl, methoxy, ethoxy, methylthio, ethylthio, trifluoromethyl, difluoromethoxy, trifluoromethoxy or trifluormethylthio, o represents 0 or 2, $R^3$ represents methyl, ethyl, n-propyl, isopropyl, difluoromethyl or trifluoromethyl, $R^4$ and $R^5$ independently represent hydrogen, methyl, ethyl, n-propyl, isopropyl, n-butyl, isobutyl, sec-butyl, tert-butyl or represent phenyl or benzyl, each of which is optionally monosubstituted by a radical from the definition of $W^1$ given below, X represents a direct bond, oxygen, sulphur, carbonyl, —$CH_2$—, —$(CH_2)_2$—, —CH=CH— (E or Z), —C≡C—, —$CH_2O$—, —$(CH_2)_2O$—, —$CH(CH_3)$O—, —$OCH_2$—, —$O(CH_2)_2$—, —$SCH_2$—, —$S(CH_2)_2$—, —$SCH(CH_3)$—, —$OCH_2O$—, —$O(CH_2)_2O$— or —$OCH(CH_3)O$—, A represents phenyl which is optionally mono- or disubstituted by radicals from the definition of $W^1$ given below or represents furyl, benzofuryl, thienyl, benzothienyl, oxazolyl, benzoxazolyl, thiazolyl, benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl, each of which is optionally mono- or disubstituted by radicals from the definition of $W^2$ given below, Z represents oxygen or sulphur, D represents hydrogen, methyl, ethyl, n-propyl, isopropyl, n-butyl, isobutyl, sec-butyl, tert-butyl, the isomeric pentyls, the isomeric hexyls, n-heptyl, n-octyl, n-isooctyl, n-nonyl, n-decyl, n-undecyl, n-dodecyl, n-tridecyl, n-tetradecyl, n-pentadecyl, n-hexadecyl, 2-propenyl, butenyl, pentenyl, hexenyl, propargyl, butynyl, pentynyl, —CF$_3$, —CHF$_2$, —CClF$_2$, —CF$_2$CHFCl, —CF$_2$CH$_2$F, —CF$_2$CHF$_2$, —CF$_2$CCl$_3$, —CH$_2$CF$_3$, —CF$_2$CHFCF$_3$, —CH$_2$CF$_2$CHF$_2$, —CH$_2$CF$_2$CF$_3$, represents cyclopropyl, cyclobutyl, cyclopentyl, cyclohexyl, cyclopropylmethyl, cyclobutylmethyl, cyclopentylmethyl or cyclohexylmethyl, each of which is optionally mono- to trisubstituted by fluorine, chlorine, bromine, methyl, ethyl, n-propyl, isopropyl, n-butyl, isobutyl, sec-butyl, tert-butyl, ethenyl, 1-propenyl, 2,2-dimethylethenyl, —CH=CCl$_2$, phenyl, styryl, fluorine-, chlorine- or bromine-substituted phenyl or 4-chlorostyryl, represents cyclopentenyl, cyclohexenyl, cyclohexenylmethyl or cyclopentenylmethyl, each of which is optionally substituted by fluorine, chlorine, methyl, ethyl, n-propyl, isopropyl, n-butyl, isobutyl, sec-butyl or tert-butyl, represents benzyl, phenethyl, naphthylmethyl, tetrahydronaphthylmethyl, furylmethyl, thienylmethyl, pyrrolylmethyl, oxazolylmethyl, isoxazolylmethyl, thiazolylmethyl or pyridylmethyl, each of which is optionally mono- or disubstituted by nitro, fluorine, chlorine, bromine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, trifluoromethyl, trifluoromethoxy, difluoromethoxy or chlorodifluoromethoxy, represents —CO—R$^6$, —CO—NR$^7$R$^8$ or the grouping —(CH$_2$)$_p$—(CR$^9$R$^{10}$)$_q$—(CH$_2$)$_r$—G, Z and D together may also represent phenoxymethyl which is optionally mono- or disubstituted by nitro, fluorine, chlorine, bromine, methyl, ethyl, n-propyl, i-propyl, methoxy, ethoxy, n-propoxy, i-propoxy, trifluoromethyl, trifluoromethoxy, difluoromethoxy or chlorodifluoromethoxy, Y represents a direct bond, oxygen, sulphur, carbonyl, —CH$_2$—, —(CH$_2$)$_2$—, —CH=CH— (E or Z), —C/C—, —CH$_2$O—, —(CH$_2$)$_2$O—, —CH(CH$_3$)O—, —OCH$_2$—, —O(CH$_2$)$_2$—, —SCH$_2$—, —S(CH$_2$)$_2$—, —SCH(CH$_3$)—, —OCH$_2$O— or —O(CH$_2$)$_2$O— or represents p-phenylene which is optionally monosubstituted by a radical from the definition of $W^1$ given below, E represents hydrogen, methyl, ethyl, n-propyl, isopropyl, n-butyl, isobutyl, sec-butyl, tert-butyl, the isomeric pentyls, the isomeric hexyls, n-heptyl, n-octyl, n-isooctyl, n-nonyl, n-decyl, n-undecyl, n-dodecyl, n-tridecyl, n-tetradecyl, n-pentadecyl, n-hexadecyl, 2-propenyl, butenyl, pentenyl, hexenyl, propargyl, butynyl, pentynyl, —CF$_3$, —CHF$_2$, —CClF$_2$, —CF$_2$CHFCl, —CF$_2$CH$_2$F, —CF$_2$CHF$_2$, —CF$_2$CCl$_3$, —CH$_2$CF$_3$, —CF$_2$CHFCF$_3$, —CH$_2$CF$_2$CHF$_2$, —CH$_2$CF$_2$CF$_3$, represents cyclopropyl, cyclobutyl, cyclopentyl or cyclohexyl, each of which is optionally mono- to trisubstituted by fluorine, chlorine, bromine, methyl, ethyl, n-propyl, isopropyl, n-butyl, isobutyl, sec-butyl, tert-butyl, ethenyl, 1-propenyl, 2,2-dimethylethenyl, —CH=CCl$_2$, phenyl, styryl, fluorine-, chlorine- or bromine-substituted phenyl or by 4-chlorostyryl, represents cyclopentenyl or cyclohexenyl, each of which is optionally substituted by fluorine, chlorine, methyl, ethyl, n-propyl, isopropyl, n-butyl, isobutyl, sec-butyl or tert-butyl, represents phenyl which is optionally mono- or disubstituted by radicals from the definition of $W^1$ given below, represents furyl, thienyl, pyrrolyl, oxazolyl, isoxazolyl, thiazolyl or pyridyl, each of which is optionally mono- or disubstituted by radicals from the definition of $W^2$ given below, or represents the grouping —(CH$_2$)$_p$—(CR$^9$R$^{10}$)$_q$—(CH$_2$)$_r$—G, $R^6$ represents methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, cyclopropyl, cyclohexyl, cyclohexyloxy, cyclohexylmethyloxy, phenyl, 2-chlorophenyl, 3-chlorophenyl, 2,6-difluorophenyl, 2,4-dichlorophenyl, 3,4-dichlorophenyl, 2-trifluoromethoxyphenyl or 4-trifluoromethoxyphenyl, $R^7$ represents hydrogen, $R^8$ represents methyl, ethyl or phenyl, which is optionally monosubstituted by chlorine, p, q and r independently represent 0, 1, 2 or 3, with the sum of p, q and r being less than 4, $R^9$ and $R^{10}$ independently represent hydrogen, methyl, ethyl, n-propyl, isopropyl, n-butyl, isobutyl, sec-butyl, tert-butyl, G represents cyano, represents 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl, each of which is optionally mono- to trisubstituted by fluorine, chlorine, bromine, methyl, ethyl, n-propyl, isopropyl or trifluoromethyl and optionally, at the point of linkage, by the radical $R^{11}$, or represents one of the groupings below:

(a) —CO—R$^{11}$ (b) —CO—OR$^{12}$ (c) —CO—NR$^{13}$R$^{14}$ (d) —CS—NR$^{13}$R$^{14}$ (e) —C(R$^{11}$)=N—R$^{15}$ (f) —C(R$^{11}$)(OR$^{16}$)(OR$^{16}$)

-continued

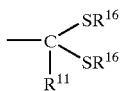
(g)

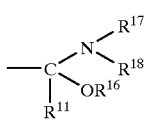
(h)

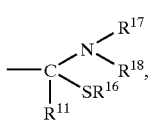
(i)

$R^{11}$ represents hydrogen, methyl, ethyl, n-propyl, isopropyl, n-butyl, isobutyl, sec-butyl, tert-butyl, the isomeric pentyls, the isomeric hexyls, —CF$_3$, —CHF$_2$, —CClF$_2$, —CF$_2$CHFCl, —CF$_2$CH$_2$F, —CF$_2$CHF$_2$, —CF$_2$CCl$_3$, —CH$_2$CF$_3$, C$_3$–C$_6$-alkenyl, C$_3$–C$_6$-alkenyl which is mono- to trisubstituted by fluorine or chlorine, represents cyclopropyl, cyclopentyl or cyclohexyl, each of which is optionally mono- or disubstituted by fluorine, chlorine, methyl, ethyl, n-propyl, isopropyl, —CF$_3$, —CHF$_2$, —CClF$_2$, —CF$_2$CHFCl, —CF$_2$CH$_2$F, —CF$_2$CHF$_2$, —CF$_2$CCl$_3$ or —CH$_2$CF$_3$, or represents phenyl which is optionally mono- or disubstituted by methylcarbonylamino, ethylcarbonylamino, methylcarbonyl-methylamino and/or radicals from the definition of W$^3$ given below, $R^{12}$ represents hydrogen, methyl, ethyl, n-propyl, isopropyl, n-butyl, isobutyl, sec-butyl, tert-butyl, —CH$_2$CF$_3$, allyl, represents cyclopropyl, cyclopentyl, cyclohexyl, cyclopropylmethyl, cyclopentylmethyl, cyclohexylmethyl, cyclopropylethyl, cyclopentylethyl or cyclohexylethyl, each of which is optionally mono- or disubstituted by fluorine, chlorine, methyl, ethyl, n-propyl, isopropyl, —CF$_3$, —CHF$_2$, —CClF$_2$, —CF$_2$CHFCl, —CF$_2$CH$_2$F, —CF$_2$CHF$_2$, —CF$_2$CCl$_3$ or —CH$_2$CF$_3$, or represents benzyl or phenethyl, each of which is optionally mono- or disubstituted by radicals from the definition of W$^3$ given below, $R^{13}$ and $R^{14}$ independently represent hydrogen, methyl, ethyl, n-propyl, isopropyl, n-butyl, isobutyl, sec-butyl, tert-butyl, —CH$_2$CF$_3$, methoxy, ethoxy, allyl, represent cyclopropyl, cyclopentyl, cyclohexyl, cyclopropylmethyl, cyclopentylmethyl or cyclohexylmethyl, each of which is optionally mono- or disubstituted by fluorine, chlorine, methyl, ethyl, n-propyl, isopropyl or trifluoromethyl, represent phenyl, benzyl or phenethyl, each of which is optionally mono- or disubstituted by radicals from the definition of W$^3$ given below, represent —OR$^{12}$ or —NR$^{11}$R$^{12}$, $R^{15}$ represents —OR$^{12}$, —NR$^{11}$R$^{12}$ or —N(R$^{11}$)—COOR$^{12}$, $R^{16}$, $R^{17}$ and $R^{18}$ independently represent methyl, ethyl, n-propyl or isopropyl, $W^1$ represents hydrogen, fluorine, chlorine, bromine, cyano, formyl, nitro, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, —CF$_3$, —CHF$_2$, —CClF$_2$, —CF$_2$CHFCl, —CF$_2$CH$_2$F, —CF$_2$CHF$_2$, —CF$_2$CCl$_3$, —CH$_2$CF$_3$, —CF$_2$CHFCF$_3$, —CH$_2$CF$_2$CHF$_2$, —CH$_2$CF$_2$CF$_3$, trifluoromethoxy, difluoromethoxy, chlorodifluoromethoxy, acetyl, propionyl, butyryl, isobutyryl, methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl or —S(O)$_a$R$^3$, $W^2$ represents fluorine, chlorine, bromine, cyano, methyl, ethyl, n-propyl, isopropyl, trifluoromethyl, trifluoromethoxy, difluoromethoxy, chlorodifluoromethoxy, acetyl, trifluoromethylthio, —CH=N—OCH$_3$, —CH=N—OC$_2$H$_5$, —CH=N—OC$_3$H$_7$, —C(CH$_3$)=N—OCH$_3$, —C(CH$_3$)=N—OC$_2$H$_5$, —C(CH$_3$)=N—OC$_3$H$_7$, —C(C$_2$H$_5$)=N—OCH$_3$, —C(C$_2$H$_5$)=N—OC$_2$H$_5$ or —C(C$_2$H$_5$)=N—OC$_3$H$_7$, $W^3$ represents fluorine, chlorine, cyano, nitro, methyl, ethyl, methoxy, ethoxy, methylthio, trifluoromethyl, trifluoromethoxy, trifluoromethylthio, dimethylamino, diethylamino, —COOR$^{19}$ or —CONR$^{20}$R$^{21}$, $R^{19}$ represents hydrogen, methyl, ethyl, n-propyl, isopropyl, tert-butyl, —CH$_2$CF$_3$, represents cyclopropyl, cyclopentyl or cyclohexyl, each of which is optionally mono- or disubstituted by fluorine, chlorine, methyl, ethyl, n-propyl, isopropyl or —CF$_3$, or represents phenyl which is optionally mono- or disubstituted by radicals from the definition of W$^4$ given below, $R^{20}$ and $R^{21}$ independently represent hydrogen, methyl, ethyl, n-propyl, isopropyl, n-butyl, isobutyl, sec-butyl, tert-butyl, —CH$_2$CF$_3$, methoxy, ethoxy, allyl, represent cyclopropyl, cyclopentyl, cyclohexyl, cyclopropylmethyl, cyclopentylmethyl or cyclohexylmethyl, each of which is optionally mono- or disubstituted by fluorine or chlorine, represent phenyl, benzyl or phenethyl, each of which is optionally mono- or disubstituted by the radicals from the definition of W$^4$ given below, represent —OR$^{16}$ or —NR$^{17}$R$^{18}$, $W^4$ represents fluorine, chlorine, bromine, cyano, nitro, methyl, ethyl, tert-butyl, methoxy, ethoxy, methylthio, trifluoromethyl, trifluoromethoxy or trifluoromethylthio.

5. A process for preparing a compound of claim 1, wherein a compound of the formula (I)

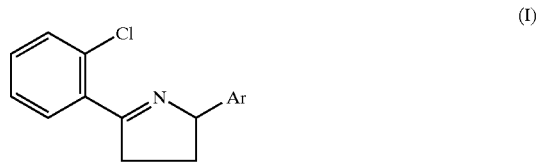
(I)

wherein

Ar is as defined in claim 1 is obtained by

A) reacting an aminoketone of the formula (VIII)

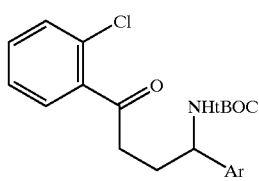

(VIII)

wherein

Ar is as defined in claim 1 with an acid, followed by cyclocondensation, optionally in the presence of an acid binder, or reducing the nitro group of a nitroketone of the formula (XVIII),

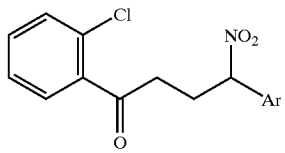

(XVIII)

wherein

Ar is as defined in claim 1, in which

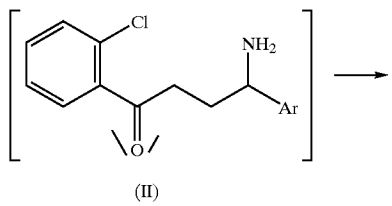

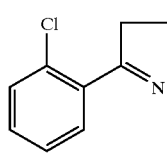

(I)

an aminoketone intermediate of the formula (II) is formed which undergoes cyclocondensation in situ to (I) in an acidic medium, or hydrolysing an imine of the formula (XXVII)

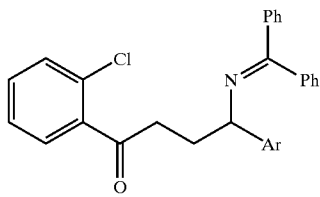

(XXVII)

wherein Ar is as defined in claim 1 with at least one aqueous acid

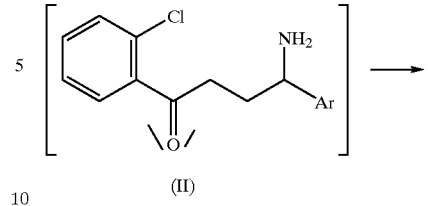

(II)

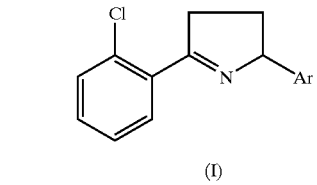

(I)

wherein an aminoketone intermediate of the formula (II) is formed which undergoes cyclocondensation in situ to (I), B) reacting a compound of the formula (III)

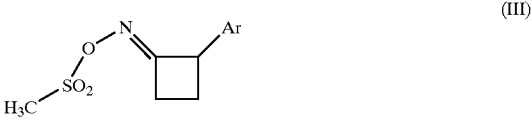

(III)

wherein

Ar is as defined in claim 1 with an aryl Grignard compound of the formula (IV)

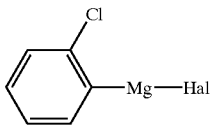

(IV)

wherein

Hal represents bromine or iodine in the presence of a solvent,

C) a compound of the formula (I-b)

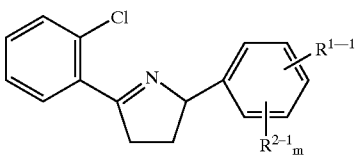

(I-b)

wherein m is as defined in claim 1

$R^{1-1}$ represents A or one of the groupings below

(m)

-continued

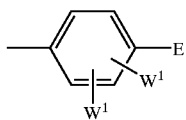
(n-a)

wherein

A, B, D, E, W$^1$ and Z are as defined in claim 1 and

R$^{2-1}$ represents hydrogen, fluorine, cyano, nitro, alkyl, alkoxy, halogenoalkyl, halogenoalkoxy, alkoxyalkoxy or —SR$^3$ wherein R$^3$ is as defined in claim 1 is obtained by coupling a compound of the formula (V)

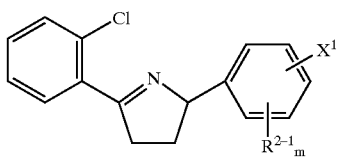
(V)

wherein m is as defined in claim 1,

R$^{2-1}$ is as defined above, and

X$^1$ represents bromine, iodine or —OSO$_2$CF$_3$ with a boronic acid of the formula (VI)

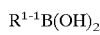 (VI)

wherein

R$^{1-1}$ is as defined above in the presence of a catalyst and in the presence of an acid binder and in the presence of a solvent, D) a compound of the formula (I-c)

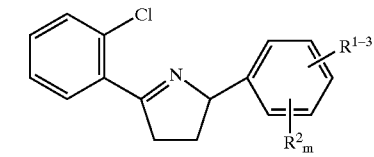
(I-c)

wherein

R$^2$ and m are as defined in claim 1,

R$^{1-2}$ represents one of the groupings below
(m-b) —B—Z—D$^1$
(n-b) —Y$^1$—E$^1$ wherein B and Z are as defined in claim 1, Y$^1$ represents oxygen or sulphur and D$^1$ and E$^1$ represent the grouping —(CH$_2$)$_p$—(CR$^9$R$^{10}$)$_q$—(CH$_2$)$_r$—G wherein R$^9$, R$^{10}$, G, p, q and r are as defined in claim 1 is obtained by condensing a cyclic imine of the formula (I-d)

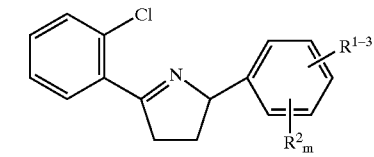
(I-d)

wherein

R$^2$ and m are as defined in claim 1 and

R$^{1-3}$ represents one of the groupings below
(m-c) —B—Z—H
(n-c) —Y$^1$—H wherein B and Z are as defined in claim 1, and Y$^1$ is as defined above, with a compound of the formula (VII)

Ab—(CH$_2$)$_p$—(CR$^9$R$^{10}$)$_q$—(CH$_2$)$_r$—G (VII)

wherein

R$^9$, R$^{10}$, G, p, q and r are as defined in claim 1 and

Ab represents a leaving group,

E) a compound of the formula (I-e)

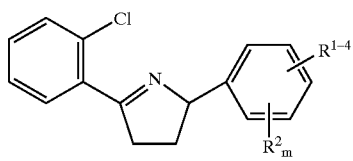
(I-e)

wherein

R$^2$ and m are as defined in claim 1 and

R$^{1-4}$ represents a grouping which contains the radical G, wherein

G represents one of the groupings (e) to (k) as defined in claim 1, is obtained by derivatizating a compound of the formula (I) in which G represents cyano or one of the groupings (a) to (d) as defined in claim 1, F) a compound of the formula (I-f)

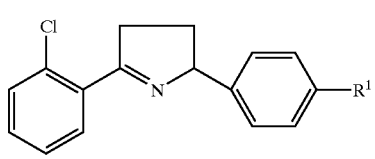
(I-f)

wherein R$^1$ is as defined in claim 1 may be obtained by reacting o-chloroacetophenone of the formula (F-I)

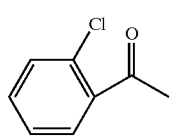
(F-I)

with dimethylmethyleneammonium chloride of the formula (F-II)

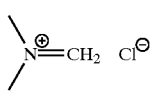 (F-II)

to yield the compound of the formula (F-III)

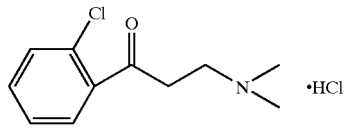 (F-III)

which is reacted a benzyl cyanide of the formula (F-IV)

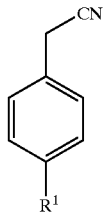 (F-IV)

wherein R¹ is as defined in claim 1 to yield a compound of the formula (F-V)

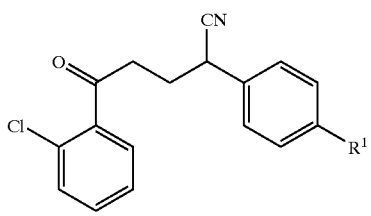 (F-V)

which is reacted with aqueous sodium hydroxide solution/ H₂O₂ to yield a compound of the formula (F-VI)

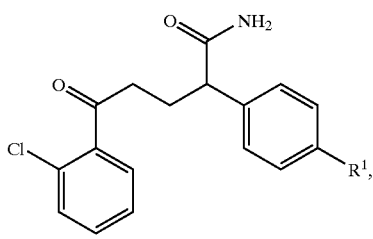 (F-VI)

wherein R¹ is as defined in claim 1, and cyclizing by reaction with PIFA (1,1-bis(trifluoroacetoxy)iodobenzene) of the formula (F-VII)

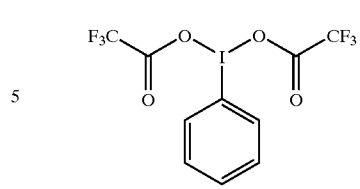 (F-VII)

to yield a cyclic imine of the formula (I-f),

G) a compound of the formula (I)

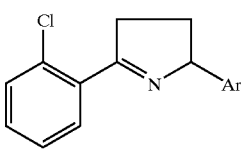 (I)

wherein Ar is as defined in claim 1 may be obtained by reacting an arylbutyrolactam of the formula (XI)

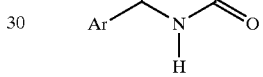 (XI)

with o-chlorobenzoyl chloride

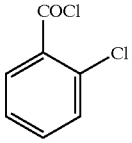

to yield a compound of the formula G(I)

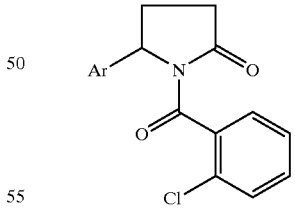 G(I)

which is reacted with methyl o-chlorobenzoate

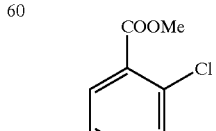

to yield a compound of the formula G(II)

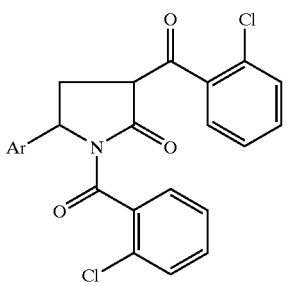

G(II)

which is reacted with HBr/glacial acetic acid to give a compound of the formula (I)

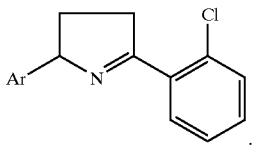

6. The compound of the formula (VIII)

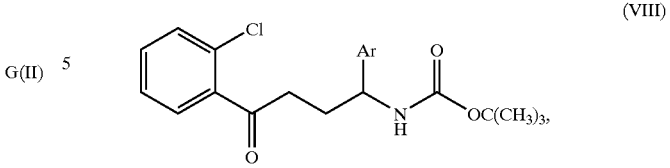

(VIII)

wherein
Ar is as defined in claim 1.

7. The compound of the formula (XVIII)

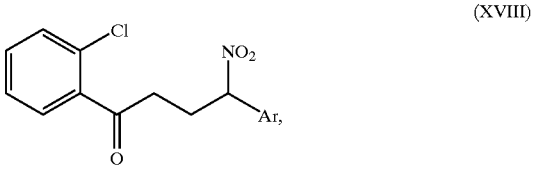

(XVIII)

wherein
Ar is as defined in claim 1.

8. A pesticide comprising at least one compound of claim 1 and at least one of extenders and surfactants.

9. A method of controlling at least one pest comprising applying at least one compound of claim 1 to said pest and/or its habitat.

10. A process for preparing a pesticide comprising mixing at least one compound of claim 1 with at least one of extenders and surfactants.

* * * * *